US011639513B2

(12) United States Patent
Tsuji et al.

(10) Patent No.: US 11,639,513 B2
(45) Date of Patent: May 2, 2023

(54) METHOD FOR PRODUCING HEPAROSAN COMPOUND HAVING ISOMERIZED HEXURONIC ACID RESIDUE

(71) Applicant: AJINOMOTO CO., INC., Tokyo (JP)

(72) Inventors: Chihiro Tsuji, Kanagawa (JP); Yasuhiro Mihara, Kanagawa (JP); Shogo Nakano, Shizuoka (JP); Tomoharu Motoyama, Shizuoka (JP); Souhei Ito, Shizuoka (JP)

(73) Assignee: AJINOMOTO CO., INC., Tokyo (JP)

( * ) Notice: Subject to any disclaimer, the term of this patent is extended or adjusted under 35 U.S.C. 154(b) by 627 days.

(21) Appl. No.: 16/515,415

(22) Filed: Jul. 18, 2019

(65) Prior Publication Data

US 2019/0338330 A1 Nov. 7, 2019

Related U.S. Application Data

(63) Continuation of application No. PCT/JP2017/030998, filed on Aug. 29, 2017.

(30) Foreign Application Priority Data

Jan. 19, 2017 (JP) ............................ JP2017-007900

(51) Int. Cl.
*C12P 19/26* (2006.01)
*C12N 9/90* (2006.01)

(52) U.S. Cl.
CPC ................ *C12P 19/26* (2013.01); *C12N 9/90* (2013.01); *C12Y 501/03017* (2013.01)

(58) Field of Classification Search
None
See application file for complete search history.

(56) References Cited

U.S. PATENT DOCUMENTS

| | | | |
|---|---|---|---|
| 8,227,449 | B2 | 7/2012 | Oreste et al. |
| 2012/0322114 | A1 | 12/2012 | Liu et al. |
| 2016/0115511 | A1 | 4/2016 | Mochizuki et al. |
| 2016/0201103 | A1 | 7/2016 | Yamazaki et al. |

FOREIGN PATENT DOCUMENTS

| | | | |
|---|---|---|---|
| WO | WO02/46379 | A2 | 6/2002 |
| WO | WO2004/017910 | A2 | 3/2004 |
| WO | WO2014/200045 | A1 | 12/2014 |
| WO | WO2015/050184 | A1 | 4/2015 |
| WO | WO2017/115674 | A1 | 7/2017 |

OTHER PUBLICATIONS

Extended European Search Report for European Patent App. No. 17892786.9 (dated Sep. 28, 2020).

Qin, Y., et al., "Structural and Functional Study of D-Glucuronyl C5-epimerase," J. Biol. Chem. 2015;290 (8):4620-4630.

Zhang, J., et al., "High Cell Density Cultivation of Recombinant *Escherichia coli* Strains Expressing 2-O-Sulfotransferase and C5-Epimerase for the Production of Bioengineered Heparin," Appl. Biochem. Biotechnol. 2015;175:2986-2995.

Lindahl, U., et al., "Generation of "Neoheparin" from *E. coli* K5 Capsular Polysaccharide," J. Med. Chem. 2005;48:349-352.

Zhang, Z., et al., "Solution Structures of Chemoenzymatically Synthesized Heparin and Its Precursors," J. Am. Chem. Soc. 2008;130:12998-13007.

Chen, J., et al., "Enzymatic Redesigning of Biologically Active Heparan Sulfate," J. Biol. Chem. 2005;280 (52):42817-42825.

Raedts, J., et al., "A Novel Bacterial Enzyme with D-Glucuronyl C5-epimerase Activity," J. Biol. Chem. 2013;288 (34):24332-24339.

Ghiselli, G., et al., "D-glucuronyl C5-epimerase acts in dorso-ventral axis formation in zebrafish," BMC Developmental Biology 2005;5:19,doi:10.1186/1471-213X-5-19, 13 pp.

International Search Report and Written Opinion for PCT Patent App. No. PCT/JP2017/030998 (dated Nov. 28, 2017) with English language translation of the ISR.

Notice of Presentation of Publications or the Like from Japanese Patent App. No. 2018-562866 dated Nov. 24, 2021 with an English language translation thereof.

Crawford, B. E., et al., "Cloning, Golgi Localization, and Enzyme Activity of the Full-length Heparin/Heparan Sulfate-Glucuronic Acid C5-epimerase," J. Biol. Chem. 2001;276(24):21538-21543.

Query: unnamed protein product Query ID: Icl/Query_50023 Length: 516, 1 pg.

Notice of Reasons for Refusal from Japanese Patent App. No. 2018-562866 (dated Dec. 28, 2021) with English language translation thereof.

(Continued)

*Primary Examiner* — Robert J Yamasaki
*Assistant Examiner* — Charles Zoltan Constantine
(74) *Attorney, Agent, or Firm* — Cermak Nakajima & McGowan LLP

(57) ABSTRACT

The present invention provides a method for producing a heparosan compound having an isomerized hexuronic acid residue and a method for producing a heparan sulfate with improved C5-epimerization efficiency. Specifically, the present invention provides a method for producing a heparosan compound having an isomerized hexuronic acid residue, said method comprising producing the heparosan compound having the isomerized hexuronic acid residue from a heparosan compound in the presence of a protein selected from the group of consisting of the following (A) to (F): (A) a protein comprising the amino acid sequence of SEQ ID No:2; (B) a protein which comprises an amino acid sequence having 90% or more homology to the amino acid sequence of SEQ ID No:2 and has a D-glucuronyl C5-epimerase substituted, added or inserted amino acid residues in the amino acid sequence of SEQ ID No:2 and has a D-glucuronyl C5-epimerase activity; (D) a protein comprising the amino acid sequence of SEQ ID NO:5; (E) a protein which comprises an amino acid sequence having 90% or more homology to the amino acid sequence of SEQ ID No:5 and has a D-glucuronyl C5-epimerase activity; and (F) a protein which comprises an amino acid sequence having one or several deleted, substituted, added or inserted amino acid residues in the amino acid sequence of SEQ ID No:5 and has a D-glucuronyl C5-epimerase activity.

14 Claims, 2 Drawing Sheets

Specification includes a Sequence Listing.

(56) References Cited

OTHER PUBLICATIONS

Notice of Presentation of Publications from Japanese Patent App. No. 2018-562866 dated Nov. 24, 2021 with an English language translation thereof.
Query: unnamed protein product Query ID: Icl/Query_50023 Length: 516, 1 pg., Nov. 24, 2021.
Communication Pursuant to Rule 114(2) EPC for European Patent App. No. 17892786.9 (dated Apr. 13, 2022).
Third Party Observations to Application No. EP17892786.9, Exhibit A: Sequence alignment between SEQ ID No. 5 and residues Gly 101 to Asn618 of AAG42004 (Sbjct), 1 pg , Apr. 13, 2022.
Third Party Observations to Application No. EP17892786.9, Exhibit B: Sequence alignment between SEQ ID No. 56 (Query) and residues Gly101 to Asn618 of AAG42002 (Sbjct), 1 pg , Apr. 13, 2022.
Third Party Observations to Application No. EP17892786.9, Exhibit C: Sequence alignment between alignment SEQ ID No. 59 (Query) and residues Gly101 to Asn618 of AAG42002 (Sbjct), 1 pg., Apr. 13, 2022.
Third Party Observations to Application No. EP17892786.9, Exhibit D: Sequence alignment between catalytically active sites of the C5-epimerase protein derived from four different species as indicated below, 1 pg., Apr. 13, 2022.

FIG. 1

```
atgcgttgtc tggcagccgg tgttcactac aagaccctga tagtgatctg tgctcttctg
tctctgctca cggttcttct ttggaacaag tgcacgagtg agaaagcact gcgcttcctg
ccccagcacc ctcaacctcc tcccagccct aaaatagaca gccatcctca gcagccccag
cccccggaac ctccacctgt agttggcgga gtgcgatatg aagagataga ctgcctgatc
aatgacgatg ccaccattaa aggtcgtcgg gaaggcagtg aggtttacat gcctttcagc
tggatggaga agtactttga ggtgtacggc aaggtggtgc agtatgatgg ttatgatcgt
tttgagtttt cacatagtta ctccaaagta tacgcccaga gagagcagta ccaccccaat
ggagtcttca tgtcctttga ggggtataac gtggaggtgc gtgacagagt caagtgcatc
agtggagtgg aaggagtacc gttgtccacc cagtggggcc ctcaagggta tttctatgct
atccagatag ctcagtatgg cctgagtcat tacagtaaga acctgacaga gcggccacct
catgtggagg tgtatgacac ggcggaggag agagacagca ggtccagcgc atggactgtc
cctaagggct gctcactcac cagagtatat gacaagacca gagccacatc tgtacgggag
ttcagtgctc cagaaaactc agagggtgtc tcacttcctc ttggcaacac taaagatttc
atcatctcct ttgacctgaa gtttacatct aatggtagcg tctctgtaat cttggagacc
acagagaaag ggccgccatt tgttatccat tacgtcacca ccacccagct catttgctc
aaggatcgtg acatcaccta tggtatcggc cctcggacca catggaccac cgtcacccgt
gaccttctca ctgacctacg caaaggcatt ggcctctcca acaccaaagc ggtcaaagct
accaaaacca tgccaaggcg tgttgtaaag ttagtggtgc acggcaccgg gacaatagac
aatatcacaa tctccaccac gtcacatatg gcggcttttt atgccgctag tgactggttg
gtgcgcaacc aggacgagcg tggtggctgg ccgatcatgg tcactcgtaa actcggggag
ggtttccgtg cactggagcc aggttggtat tcggccatgg cacaaggaca agccatgtcc
actttagtgc gtgcctatct aatgacaaaa gatgacaggt acctaaaggc tgccctgcga
gccaccggac cttttaaact gccctcagaa cagcacggtg tcaaagcagt gttcatgaac
aagtatgact ggtatgagga gtaccccaca atccccagct ccttcgtttt gaatggattc
atctattccc tcataggtct gtttgacctg gcgcaaactg cgggtgagaa actcgggcgg
gatgcgggac agctgtacag caagggaatg gagtccttga aagttatgct tcccctgtat
gacacagggt caggcactat ctatgacctg cgccacttta ttttgggcac ggcgcccaat
ttggcccgtt gggactacca cacaacgcac atcaaccagc tccagctgct gggtactatt
gacaactcgc ccatcttcag ggactccgtc aagcgctgga aaagctacct gaaaggaggg
agggctaagc acaattaa
```

(Full length = SEQ ID NO:1, The area surrounded by the framework = SEQ ID NO:3)

FIG. 2

MRCLAAGVHY KTLIVICALL SLLTVLLWNK CTSEKALRFL PQHPQPPPSP KIDSHPQQPQ
PPEPPPVVGG VRYEEIDCLI NDDATIKGRR EGSEVYMPFS WMEKYFEVYG KVVQYDGYDR
FEFSHSYSKV YAQREQYHPN GVFMSFEGYN VEVRDRVKCI SGVEGVPLST QWGPQGYFYA
IQIAQYGLSH YSKNLTERPP HVEVYDTAEE RDSRSSAWTV PKGCSLTRVY DKTRATSVRE
FSAPENSEGV SLPLGNTKDF IISFDLKFTS NGSVSVILET TEKGPPFVIH YVTTTQLILL
KDRDITYGIG PRTTWTTVTR DLLTDLRKGI GLSNTKAVKA TKTMPRRVVK LVVHGTGTID
NITISTTSHM AAFYAASDWL VRNQDERGGW PIMVTRKLGE GFRALEPGWY SAMAQGQAMS
TLVRAYLMTK DDRYLKAALR ATGPFKLPSE QHGVKAVFMN KYDWYEEYPT IPSSFVLNGF
IYSLIGLFDL AQTAGEKLGR DAGQLYSKGM ESLKVMLPLY DTGSGTIYDL RHFILGTAPN
LARWDYHTTH INQLQLLGTI DNSPIFRDSV KRWKSYLKGG RAKHN (Full length = SEQ ID NO:2, The area surrounded by the framework (Gly70-Asn585) = SEQ ID NO:5)

FIG. 3

GGCGTTCGGTATGAAGAAATCGACTGCTTGATTAACGACGATGCAACCATCAAAGGGCGCCGCGAAGG
CTCTGAGGTGTACATGCCGTTTAGCTGGATGGAAAAGTATTTCGAAGTGTACGGCAAAGTTGTGCAAT
ACGATGGCTATGATCGCTTTGAATTCTCTCATTCATACAGCAAAGTGTATGCGCAGCGCGAGCAGTAT
CATCCGAATGGTGTCTTTATGAGCTTTGAGGGGTATAACGTAGAAGTGCGCGATCGTGTCAAATGTAT
CTCCGGTGTTGAAGGTGTTCCGCTTAGCACCCAGTGGGGTCCACAGGGCTACTTTTATGCGATTCAGA
TTGCCCAGTACGGTCTGTCGCACTATTCGAAGAACTTAACCGAACGTCCGCCGCATGTGGAGGTGTAT
GATACGGCGGAAGAACGCGACAGTCGTAGTTCTGCCTGGACCGTTCCAAAAGGATGCTCACTGACCCG
CGTTTACGACAAAACCCGCGCGACAAGCGTCCGCGAATTTAGCGCTCCGGAAAATAGCGAAGGAGTTA
GCTTACCACTTGGTAACACCAAAGATTTCATTATCTCCTTTGACCTGAAATTCACAAGTAATGGGTCA
GTCTCTGTGATTTTGGAGACTACTGAAAAGGGACCGCCGTTTGTGATCCACTATGTCACCACGACGCA
GTTGATCCTTCTGAAAGATCGTGACATTACCTACGGGATTGGTCCACGCACGACCTGGACAACTGTAA
CCCGGGATCTGCTGACGGACTTACGCAAAGGTATCGGCCTTAGCAACACGAAGGCAGTAAAAGCAACC
AAAACCATGCCGCGCCGTGTGGTAAAACTGGTCGTACATGGCACGGGTACCATTGACAACATCACCAT
TAGCACCACGTCCCATATGGCCGCCTTTTATGCCGCGTCTGATTGGTTGGTGCGCAATCAGGATGAAC
GTGGTGGCTGGCCGATTATGGTCACCCGCAAATTAGGCGAGGGCTTCCGTGCCTTGGAACCGGGCTGG
TATTCCGCGATGGCGCAGGGCCAAGCGATGTCCACTCTGGTGCGTGCCTATCTCATGACGAAAGACGA
TCGTTATCTGAAAGCGGCGCTGCGTGCAACTGGCCCTTTTAAGCTGCCGTCAGAACAGCACGGAGTGA
AAGCGGTGTTTATGAACAAATACGATTGGTACGAAGAGTATCCGACAATCCCTAGTTCCTTTGTCCTG
AACGGTTTCATCTATTCACTTATTGGCCTGTTTGATCTGGCACAGACTGCTGGCGAGAAACTGGGCCG
TGATGCGGGTCAGCTCTACAGCAAGGGGATGGAGTCTCTGAAAGTTATGTTACCGCTCTACGATACAG
GGTCGGGGACCATCTATGATCTCCGCCACTTCATTCTGGGAACAGCTCCCAATCTGGCACGTTGGGAT
TACCACACCACGCATATTAATCAGCTGCAACTGCTGGGTACTATCGATAATAGTCCGATTTTCCGCGA
CTCGGTCAAACGCTGGAAATCGTACCTGAAAGGCGGTCGCGCAAAGCATAATtaa
(SEQ ID NO:4)

SEQUENCE LISTING

```
<160> NUMBER OF SEQ ID NOS: 72

<210> SEQ ID NO 1
<211> LENGTH: 1758
<212> TYPE: DNA
<213> ORGANISM: Danio rerio

<400> SEQUENCE: 1

atgcgttgtc tggcagccgg tgttcactac aagaccctga tagtgatctg tgctcttctg      60

tctctgctca cggttcttct ttggaacaag tgcacgagtg agaaagcact gcgcttcctg     120

ccccagcacc ctcaacctcc tcccagccct aaaatagaca gccatcctca gcagccccag     180

cccccggaac ctccacctgt agttggcgga gtgcgatatg aagagataga ctgcctgatc     240

aatgacgatg ccaccattaa aggtcgtcgg gaaggcagtg aggtttacat gcctttcagc     300

tggatggaga agtactttga ggtgtacggc aaggtggtgc agtatgatgg ttatgatcgt     360

tttgagtttt cacatagtta ctccaaagta tacgcccaga gagagcagta ccaccccaat     420

ggagtcttca tgtcctttga ggggtataac gtggaggtgc gtgacagagt caagtgcatc     480

agtggagtgg aaggagtacc gttgtccacc cagtggggcc ctcaagggta tttctatgct     540

atccagatag ctcagtatgg cctgagtcat tacagtaaga acctgacaga gcggccacct     600

catgtggagg tgtatgacac ggcggaggag agagacagca ggtccagcgc atggactgtc     660
```

```
cctaagggct gctcactcac cagagtatat gacaagacca gagccacatc tgtacgggag     720

ttcagtgctc cagaaaactc agagggtgtc tcacttcctc ttggcaacac taaagatttc     780

atcatctcct ttgacctgaa gtttacatct aatggtagcg tctctgtaat cttggagacc     840

acagagaaag ggccgccatt tgttatccat tacgtcacca ccacccagct cattttgctc     900

aaggatcgtg acatcaccta tggtatcggc cctcggacca catggaccac cgtcacccgt     960

gaccttctca ctgacctacg caaaggcatt ggcctctcca acaccaaagc ggtcaaagct    1020

accaaaacca tgccaaggcg tgttgtaaag ttagtggtgc acggcaccgg gacaatagac    1080

aatatcacaa tctccaccac gtcacatatg gcggcttttt atgccgctag tgactggttg    1140

gtgcgcaacc aggacgagcg tggtggctgg ccgatcatgg tcactcgtaa actcggggag    1200

ggtttccgtg cactggagcc aggttggtat tcggccatgg cacaaggaca agccatgtcc    1260

actttagtgc gtgcctatct aatgacaaaa gatgacaggt acctaaaggc tgccctgcga    1320

gccaccggac cttttaaact gccctcagaa cagcacggtg tcaaagcagt gttcatgaac    1380

aagtatgact ggtatgagga gtaccccaca atccccagct ccttcgtttt gaatggattc    1440

atctattccc tcataggtct gtttgacctg gcgcaaactg cgggtgagaa actcgggcgg    1500

gatgcgggac agctgtacag caagggaatg gagtccttga aagttatgct tcccctgtat    1560

gacacagggt caggcactat ctatgacctg cgccacttta ttttgggcac ggcgcccaat    1620

ttggcccgtt gggactacca cacaacgcac atcaaccagc tccagctgct gggtactatt    1680

gacaactcgc ccatcttcag ggactccgtc aagcgctgga aaagctacct gaaaggaggg    1740

agggctaagc acaattaa                                                  1758


<210> SEQ ID NO 2
<211> LENGTH: 585
<212> TYPE: PRT
<213> ORGANISM: Danio rerio

<400> SEQUENCE: 2

Met Arg Cys Leu Ala Ala Gly Val His Tyr Lys Thr Leu Ile Val Ile
1               5                   10                  15

Cys Ala Leu Leu Ser Leu Leu Thr Val Leu Leu Trp Asn Lys Cys Thr
            20                  25                  30

Ser Glu Lys Ala Leu Arg Phe Leu Pro Gln His Pro Gln Pro Pro Pro
        35                  40                  45

Ser Pro Lys Ile Asp Ser His Pro Gln Gln Pro Gln Pro Pro Glu Pro
    50                  55                  60

Pro Pro Val Val Gly Gly Val Arg Tyr Glu Glu Ile Asp Cys Leu Ile
65                  70                  75                  80

Asn Asp Asp Ala Thr Ile Lys Gly Arg Arg Glu Gly Ser Glu Val Tyr
                85                  90                  95

Met Pro Phe Ser Trp Met Glu Lys Tyr Phe Glu Val Tyr Gly Lys Val
            100                 105                 110

Val Gln Tyr Asp Gly Tyr Asp Arg Phe Glu Phe Ser His Ser Tyr Ser
        115                 120                 125

Lys Val Tyr Ala Gln Arg Glu Gln Tyr His Pro Asn Gly Val Phe Met
    130                 135                 140

Ser Phe Glu Gly Tyr Asn Val Glu Val Arg Asp Arg Val Lys Cys Ile
145                 150                 155                 160

Ser Gly Val Glu Gly Val Pro Leu Ser Thr Gln Trp Gly Pro Gln Gly
                165                 170                 175
```

-continued

```
Tyr Phe Tyr Ala Ile Gln Ile Ala Gln Tyr Gly Leu Ser His Tyr Ser
            180                 185                 190

Lys Asn Leu Thr Glu Arg Pro Pro His Val Glu Val Tyr Asp Thr Ala
        195                 200                 205

Glu Glu Arg Asp Ser Arg Ser Ser Ala Trp Thr Val Pro Lys Gly Cys
    210                 215                 220

Ser Leu Thr Arg Val Tyr Asp Lys Thr Arg Ala Thr Ser Val Arg Glu
225                 230                 235                 240

Phe Ser Ala Pro Glu Asn Ser Glu Gly Val Ser Leu Pro Leu Gly Asn
                245                 250                 255

Thr Lys Asp Phe Ile Ile Ser Phe Asp Leu Lys Phe Thr Ser Asn Gly
            260                 265                 270

Ser Val Ser Val Ile Leu Glu Thr Thr Glu Lys Gly Pro Pro Phe Val
        275                 280                 285

Ile His Tyr Val Thr Thr Thr Gln Leu Ile Leu Leu Lys Asp Arg Asp
    290                 295                 300

Ile Thr Tyr Gly Ile Gly Pro Arg Thr Thr Trp Thr Thr Val Thr Arg
305                 310                 315                 320

Asp Leu Leu Thr Asp Leu Arg Lys Gly Ile Gly Leu Ser Asn Thr Lys
                325                 330                 335

Ala Val Lys Ala Thr Lys Thr Met Pro Arg Arg Val Val Lys Leu Val
            340                 345                 350

Val His Gly Thr Gly Thr Ile Asp Asn Ile Thr Ile Ser Thr Thr Ser
        355                 360                 365

His Met Ala Ala Phe Tyr Ala Ala Ser Asp Trp Leu Val Arg Asn Gln
    370                 375                 380

Asp Glu Arg Gly Gly Trp Pro Ile Met Val Thr Arg Lys Leu Gly Glu
385                 390                 395                 400

Gly Phe Arg Ala Leu Glu Pro Gly Trp Tyr Ser Ala Met Ala Gln Gly
                405                 410                 415

Gln Ala Met Ser Thr Leu Val Arg Ala Tyr Leu Met Thr Lys Asp Asp
            420                 425                 430

Arg Tyr Leu Lys Ala Ala Leu Arg Ala Thr Gly Pro Phe Lys Leu Pro
        435                 440                 445

Ser Glu Gln His Gly Val Lys Ala Val Phe Met Asn Lys Tyr Asp Trp
    450                 455                 460

Tyr Glu Glu Tyr Pro Thr Ile Pro Ser Ser Phe Val Leu Asn Gly Phe
465                 470                 475                 480

Ile Tyr Ser Leu Ile Gly Leu Phe Asp Leu Ala Gln Thr Ala Gly Glu
                485                 490                 495

Lys Leu Gly Arg Asp Ala Gly Gln Leu Tyr Ser Lys Gly Met Glu Ser
            500                 505                 510

Leu Lys Val Met Leu Pro Leu Tyr Asp Thr Gly Ser Gly Thr Ile Tyr
        515                 520                 525

Asp Leu Arg His Phe Ile Leu Gly Thr Ala Pro Asn Leu Ala Arg Trp
    530                 535                 540

Asp Tyr His Thr Thr His Ile Asn Gln Leu Gln Leu Leu Gly Thr Ile
545                 550                 555                 560

Asp Asn Ser Pro Ile Phe Arg Asp Ser Val Lys Arg Trp Lys Ser Tyr
                565                 570                 575

Leu Lys Gly Gly Arg Ala Lys His Asn
            580                 585
```

-continued

<210> SEQ ID NO 3
<211> LENGTH: 1551
<212> TYPE: DNA
<213> ORGANISM: Danio rerio

<400> SEQUENCE: 3

```
ggagtgcgat atgaagagat agactgcctg atcaatgacg atgccaccat taaaggtcgt     60
cgggaaggca gtgaggttta catgcctttc agctggatgg agaagtactt tgaggtgtac    120
ggcaaggtgg tgcagtatga tggttatgat cgttttgagt tttcacatag ttactccaaa    180
gtatacgccc agagagagca gtaccacccc aatggagtct tcatgtcctt tgaggggtat    240
aacgtggagg tgcgtgacag agtcaagtgc atcagtggag tggaaggagt accgttgtcc    300
acccagtggg gccctcaagg gtatttctat gctatccaga tagctcagta tggcctgagt    360
cattacagta agaacctgac agagcggcca cctcatgtgg aggtgtatga cacggcggag    420
gagagagaca gcaggtccag cgcatggact gtccctaagg gctgctcact caccagagta    480
tatgacaaga ccagagccac atctgtacgg gagttcagtg ctccagaaaa ctcagagggt    540
gtctcacttc ctcttggcaa cactaaagat ttcatcatct cctttgacct gaagtttaca    600
tctaatggta gcgtctctgt aatcttggag accacagaga aagggccgcc atttgttatc    660
cattacgtca ccaccaccca gctcattttg ctcaaggatc gtgacatcac ctatggtatc    720
ggccctcgga ccacatggac caccgtcacc cgtgaccttc tcactgacct acgcaaaggc    780
attggcctct ccaacaccaa agcggtcaaa gctaccaaaa ccatgccaag gcgtgttgta    840
aagttagtgg tgcacggcac cgggacaata gacaatatca caatctccac cacgtcacat    900
atggcggctt tttatgccgc tagtgactgg ttggtgcgca accaggacga gcgtggtggc    960
tggccgatca tggtcactcg taaactcggg gagggtttcc gtgcactgga gccaggttgg   1020
tattcggcca tggcacaagg acaagccatg tccactttag tgcgtgccta tctaatgaca   1080
aaagatgaca ggtacctaaa ggctgccctg cgagccaccg gaccttttaa actgccctca   1140
gaacagcacg gtgtcaaagc agtgttcatg aacaagtatg actggtatga ggagtacccc   1200
acaatcccca gctccttcgt tttgaatgga ttcatctatt ccctcatagg tctgtttgac   1260
ctggcgcaaa ctgcgggtga gaaactcggg cgggatgcgg gacagctgta cagcaaggga   1320
atggagtcct tgaaagttat gcttcccctg tatgacacag ggtcaggcac tatctatgac   1380
ctgcgccact ttattttggg cacggcgccc aatttggccc gttgggacta ccacacaacg   1440
cacatcaacc agctccagct gctgggtact attgacaact cgcccatctt cagggactcc   1500
gtcaagcgct ggaaaagcta cctgaaagga gggagggcta agcacaatta a            1551
```

<210> SEQ ID NO 4
<211> LENGTH: 1551
<212> TYPE: DNA
<213> ORGANISM: Danio rerio

<400> SEQUENCE: 4

```
ggcgttcggt atgaagaaat cgactgcttg attaacgacg atgcaaccat caaagggcgc     60
cgcgaaggct ctgaggtgta catgccgttt agctggatgg aaaagtattt cgaagtgtac    120
ggcaaagttg tgcaatacga tggctatgat cgctttgaat tctctcattc atacagcaaa    180
gtgtatgcgc agcgcgagca gtatcatccg aatggtgtct ttatgagctt tgaggggtat    240
aacgtagaag tgcgcgatcg tgtcaaatgt atctccggtg ttgaaggtgt tccgcttagc    300
acccagtggg gtccacaggg ctacttttat gcgattcaga ttgcccagta cggtctgtcg    360
```

-continued

```
cactattcga agaacttaac cgaacgtccg ccgcatgtgg aggtgtatga tacggcggaa    420

gaacgcgaca gtcgtagttc tgcctggacc gttccaaaag gatgctcact gacccgcgtt    480

tacgacaaaa cccgcgcgac aagcgtccgc gaatttagcg ctccggaaaa tagcgaagga    540

gttagcttac cacttggtaa caccaaagat ttcattatct cctttgacct gaaattcaca    600

agtaatgggt cagtctctgt gattttggag actactgaaa agggaccgcc gtttgtgatc    660

cactatgtca ccacgacgca gttgatcctt ctgaaagatc gtgacattac ctacgggatt    720

ggtccacgca cgacctggac aactgtaacc cgggatctgc tgacggactt acgcaaaggt    780

atcggcctta gcaacacgaa ggcagtaaaa gcaaccaaaa ccatgccgcg ccgtgtggta    840

aaactggtcg tacatggcac gggtaccatt gacaacatca ccattagcac cacgtcccat    900

atggccgcct tttatgccgc gtctgattgg ttggtgcgca atcaggatga acgtggtggc    960

tggccgatta tggtcacccg caaattaggc gagggcttcc gtgccttgga accgggctgg   1020

tattccgcga tggcgcaggg ccaagcgatg tccactctgg tgcgtgccta tctcatgacg   1080

aaagacgatc gttatctgaa agcggcgctg cgtgcaactg gcccttttaa gctgccgtca   1140

gaacagcacg gagtgaaagc ggtgtttatg aacaaatacg attggtacga agagtatccg   1200

acaatcccta gttcctttgt cctgaacggt ttcatctatt cacttattgg cctgtttgat   1260

ctggcacaga ctgctggcga gaaactgggc cgtgatgcgg gtcagctcta cagcaagggg   1320

atggagtctc tgaaagttat gttaccgctc tacgatacag ggtcggggac catctatgat   1380

ctccgccact tcattctggg aacagctccc aatctggcac gttgggatta ccacaccacg   1440

catattaatc agctgcaact gctgggtact atcgataata gtccgatttt ccgcgactcg   1500

gtcaaacgct ggaaatcgta cctgaaaggc ggtcgcgcaa agcataatta a             1551
```

<210> SEQ ID NO 5
<211> LENGTH: 516
<212> TYPE: PRT
<213> ORGANISM: Danio rerio

<400> SEQUENCE: 5

```
Gly Val Arg Tyr Glu Glu Ile Asp Cys Leu Ile Asn Asp Asp Ala Thr
1               5                   10                  15

Ile Lys Gly Arg Arg Glu Gly Ser Glu Val Tyr Met Pro Phe Ser Trp
            20                  25                  30

Met Glu Lys Tyr Phe Glu Val Tyr Gly Lys Val Val Gln Tyr Asp Gly
        35                  40                  45

Tyr Asp Arg Phe Glu Phe Ser His Ser Tyr Ser Lys Val Tyr Ala Gln
    50                  55                  60

Arg Glu Gln Tyr His Pro Asn Gly Val Phe Met Ser Phe Glu Gly Tyr
65                  70                  75                  80

Asn Val Glu Val Arg Asp Arg Val Lys Cys Ile Ser Gly Val Glu Gly
                85                  90                  95

Val Pro Leu Ser Thr Gln Trp Gly Pro Gln Gly Tyr Phe Tyr Ala Ile
            100                 105                 110

Gln Ile Ala Gln Tyr Gly Leu Ser His Tyr Ser Lys Asn Leu Thr Glu
        115                 120                 125

Arg Pro Pro His Val Glu Val Tyr Asp Thr Ala Glu Glu Arg Asp Ser
    130                 135                 140

Arg Ser Ser Ala Trp Thr Val Pro Lys Gly Cys Ser Leu Thr Arg Val
145                 150                 155                 160

Tyr Asp Lys Thr Arg Ala Thr Ser Val Arg Glu Phe Ser Ala Pro Glu
```

-continued

```
                165                 170                 175

Asn Ser Glu Gly Val Ser Leu Pro Leu Gly Asn Thr Lys Asp Phe Ile
            180                 185                 190

Ile Ser Phe Asp Leu Lys Phe Thr Ser Asn Gly Ser Val Ser Val Ile
        195                 200                 205

Leu Glu Thr Thr Glu Lys Gly Pro Pro Phe Val Ile His Tyr Val Thr
    210                 215                 220

Thr Thr Gln Leu Ile Leu Leu Lys Asp Arg Asp Ile Thr Tyr Gly Ile
225                 230                 235                 240

Gly Pro Arg Thr Thr Trp Thr Thr Val Thr Arg Asp Leu Leu Thr Asp
                245                 250                 255

Leu Arg Lys Gly Ile Gly Leu Ser Asn Thr Lys Ala Val Lys Ala Thr
            260                 265                 270

Lys Thr Met Pro Arg Arg Val Val Lys Leu Val Val His Gly Thr Gly
        275                 280                 285

Thr Ile Asp Asn Ile Thr Ile Ser Thr Thr Ser His Met Ala Ala Phe
    290                 295                 300

Tyr Ala Ala Ser Asp Trp Leu Val Arg Asn Gln Asp Glu Arg Gly Gly
305                 310                 315                 320

Trp Pro Ile Met Val Thr Arg Lys Leu Gly Glu Gly Phe Arg Ala Leu
                325                 330                 335

Glu Pro Gly Trp Tyr Ser Ala Met Ala Gln Gly Gln Ala Met Ser Thr
            340                 345                 350

Leu Val Arg Ala Tyr Leu Met Thr Lys Asp Asp Arg Tyr Leu Lys Ala
        355                 360                 365

Ala Leu Arg Ala Thr Gly Pro Phe Lys Leu Pro Ser Glu Gln His Gly
    370                 375                 380

Val Lys Ala Val Phe Met Asn Lys Tyr Asp Trp Tyr Glu Glu Tyr Pro
385                 390                 395                 400

Thr Ile Pro Ser Ser Phe Val Leu Asn Gly Phe Ile Tyr Ser Leu Ile
                405                 410                 415

Gly Leu Phe Asp Leu Ala Gln Thr Ala Gly Glu Lys Leu Gly Arg Asp
            420                 425                 430

Ala Gly Gln Leu Tyr Ser Lys Gly Met Glu Ser Leu Lys Val Met Leu
        435                 440                 445

Pro Leu Tyr Asp Thr Gly Ser Gly Thr Ile Tyr Asp Leu Arg His Phe
    450                 455                 460

Ile Leu Gly Thr Ala Pro Asn Leu Ala Arg Trp Asp Tyr His Thr Thr
465                 470                 475                 480

His Ile Asn Gln Leu Gln Leu Leu Gly Thr Ile Asp Asn Ser Pro Ile
                485                 490                 495

Phe Arg Asp Ser Val Lys Arg Trp Lys Ser Tyr Leu Lys Gly Gly Arg
            500                 505                 510

Ala Lys His Asn
        515


<210> SEQ ID NO 6
<211> LENGTH: 1575
<212> TYPE: DNA
<213> ORGANISM: Homo sapiens

<400> SEQUENCE: 6

ggccgcgtct tctggaggcc tgaaatatga agaaattgac tgcctgatca acgatgagca      60

taccattaaa ggtcgtcgtg aaggtaatga agtttttctg ccgtttacct gggtggagaa     120
```

-continued

```
atactttgat gtttatggta aagtggtgca gtatgatggc tatgatcgtt ttgaatttag    180

ccatagctac agcaaagttt atgcacagcg tgcaccgtat catcctgatg gtgtttttat    240

gagctttgag ggctataatg ttgaagttcg tgatcgcgtt aaatgcatta gcggtgttga    300

aggtgttccg ctgagcaccc agtggggtcc gcagggttat ttctatccga ttcagattgc    360

acagtatggc ctgagccatt atagcaaaaa tctgaccgaa aaaccgcctc acattgaagt    420

ttatgaaacc gcagaagatc gcgacaaaaa caaaccgaat gattggaccg ttccgaaagg    480

ttgttttatg gcaaatgttg cagataaaag ccgcttcacc aatgtgaaac agtttattgc    540

accggaaacc agcgaaggtg ttagcctgca gctgggtaat accaaagatt ttatcattag    600

cttcgatctg aaatttctga ccaatggtag cgttagcgtt gttctggaaa ccaccgaaaa    660

aaatcagctg tttaccatcc attatgtgag caatgcccag ctgattgcat ttaaagaacg    720

cgatatctat tatggcattg gtccgcgtac cagttggagc accgttaccc gtgatctggt    780

taccgatctg cgtaaaggtg ttggtctgag caatacaaaa gcagttaaac cgaccaaaat    840

tatgccgaaa aaagttgttc gtctgatcgc caaaggtaaa ggttttctgg ataacattac    900

cattagcacc accgcacata tggcagcatt ttttgcagca agcgattggc tggttcgtaa    960

ccaggatgaa aaaggtggtt ggccgattat ggttacccgt aaactgggtg aaggttttaa   1020

aagcctggaa ccgggttggt atagcgcaat ggcacagggt caggcaatta gcaccctggt   1080

tcgtgcatat ctgctgacca aagatcatat ttttctgaat agcgcactgc gtgcaaccgc   1140

accgtacaaa tttctgtcag aacagcatgg tgttaaagcc gtgtttatga acaaacacga   1200

ttggtatgaa gaatatccga ccaccccgag cagctttgtt ctgaatggtt ttatgtatag   1260

cctgatcggt ctgtacgacc tgaaagaaac agccggtgaa aaactgggta aagaagcacg   1320

tagcctgtac gaacgtggta tggaaagcct gaaagcaatg ctgccgctgt atgataccgg   1380

tagcggcacc atttatgatc tgcgtcattt tatgctgggt atcgcaccga atctggcacg   1440

ttgggattat cataccaccc atattaatca gctgcaactg ctgagtacca ttgatgaaag   1500

tccggtgttt aaagaatttg tgaaacgctg gaaaagctac ctgaaaggta gccgtgcaaa   1560

acacaattaa ctcga                                                    1575
```

<210> SEQ ID NO 7
<211> LENGTH: 517
<212> TYPE: PRT
<213> ORGANISM: Homo sapiens

<400> SEQUENCE: 7

```
Gly Leu Lys Tyr Glu Glu Ile Asp Cys Leu Ile Asn Asp Glu His Thr
1               5                   10                  15

Ile Lys Gly Arg Arg Glu Gly Asn Glu Val Phe Leu Pro Phe Thr Trp
            20                  25                  30

Val Glu Lys Tyr Phe Asp Val Tyr Gly Lys Val Val Gln Tyr Asp Gly
        35                  40                  45

Tyr Asp Arg Phe Glu Phe Ser His Ser Tyr Ser Lys Val Tyr Ala Gln
    50                  55                  60

Arg Ala Pro Tyr His Pro Asp Gly Val Phe Met Ser Phe Glu Gly Tyr
65                  70                  75                  80

Asn Val Glu Val Arg Asp Arg Val Lys Cys Ile Ser Gly Val Glu Gly
                85                  90                  95

Val Pro Leu Ser Thr Gln Trp Gly Pro Gln Gly Tyr Phe Tyr Pro Ile
            100                 105                 110
```

-continued

```
Gln Ile Ala Gln Tyr Gly Leu Ser His Tyr Ser Lys Asn Leu Thr Glu
        115                 120                 125

Lys Pro Pro His Ile Glu Val Tyr Glu Thr Ala Glu Asp Arg Asp Lys
    130                 135                 140

Asn Lys Pro Asn Asp Trp Thr Val Pro Lys Gly Cys Phe Met Ala Asn
145                 150                 155                 160

Val Ala Asp Lys Ser Arg Phe Thr Asn Val Lys Gln Phe Ile Ala Pro
                165                 170                 175

Glu Thr Ser Glu Gly Val Ser Leu Gln Leu Gly Asn Thr Lys Asp Phe
            180                 185                 190

Ile Ile Ser Phe Asp Leu Lys Phe Leu Thr Asn Gly Ser Val Ser Val
        195                 200                 205

Val Leu Glu Thr Thr Glu Lys Asn Gln Leu Phe Thr Ile His Tyr Val
    210                 215                 220

Ser Asn Ala Gln Leu Ile Ala Phe Lys Glu Arg Asp Ile Tyr Tyr Gly
225                 230                 235                 240

Ile Gly Pro Arg Thr Ser Trp Ser Thr Val Thr Arg Asp Leu Val Thr
                245                 250                 255

Asp Leu Arg Lys Gly Val Gly Leu Ser Asn Thr Lys Ala Val Lys Pro
            260                 265                 270

Thr Lys Ile Met Pro Lys Lys Val Val Arg Leu Ile Ala Lys Gly Lys
        275                 280                 285

Gly Phe Leu Asp Asn Ile Thr Ile Ser Thr Thr Ala His Met Ala Ala
    290                 295                 300

Phe Phe Ala Ala Ser Asp Trp Leu Val Arg Asn Gln Asp Glu Lys Gly
305                 310                 315                 320

Gly Trp Pro Ile Met Val Thr Arg Lys Leu Gly Glu Gly Phe Lys Ser
                325                 330                 335

Leu Glu Pro Gly Trp Tyr Ser Ala Met Ala Gln Gly Gln Ala Ile Ser
            340                 345                 350

Thr Leu Val Arg Ala Tyr Leu Leu Thr Lys Asp His Ile Phe Leu Asn
        355                 360                 365

Ser Ala Leu Arg Ala Thr Ala Pro Tyr Lys Phe Leu Ser Glu Gln His
    370                 375                 380

Gly Val Lys Ala Val Phe Met Asn Lys His Asp Trp Tyr Glu Glu Tyr
385                 390                 395                 400

Pro Thr Thr Pro Ser Ser Phe Val Leu Asn Gly Phe Met Tyr Ser Leu
                405                 410                 415

Ile Gly Leu Tyr Asp Leu Lys Glu Thr Ala Gly Glu Lys Leu Gly Lys
            420                 425                 430

Glu Ala Arg Ser Leu Tyr Glu Arg Gly Met Glu Ser Leu Lys Ala Met
        435                 440                 445

Leu Pro Leu Tyr Asp Thr Gly Ser Gly Thr Ile Tyr Asp Leu Arg His
    450                 455                 460

Phe Met Leu Gly Ile Ala Pro Asn Leu Ala Arg Trp Asp Tyr His Thr
465                 470                 475                 480

Thr His Ile Asn Gln Leu Gln Leu Leu Ser Thr Ile Asp Glu Ser Pro
                485                 490                 495

Val Phe Lys Glu Phe Val Lys Arg Trp Lys Ser Tyr Leu Lys Gly Ser
            500                 505                 510

Arg Ala Lys His Asn
        515
```

<210> SEQ ID NO 8
<211> LENGTH: 1554
<212> TYPE: DNA
<213> ORGANISM: Monodelphis domestica

<400> SEQUENCE: 8
ggcctgaaat acgaggaaat cgattgtctg attaatgacg agcatacgat aaaaggccgt 60
cgtgaaggga acgaaatttt cctgccgttt acctgggtgg agaaatactt tgaggtgtac 120
ggcaagatgg ttcagtatga tggctatgat cgcttcgaat tttcgcacag ctattcgaaa 180
gtgtatgcgc aacgtgctcc ttaccatccg gacggggtgt tcatgtcctt tgaaggctat 240
aacgttgagg ttcgtgatcg tgttaaatgc atctctggtg ttgagggagt gccgttaagc 300
acccagtggg ggccacaggg ttacttctat ccgattcaga tagcgcaata tggactgtcg 360
cactactcca agaacctgac cgaaaagccg ccgcatattg aagtgtatga aactgcggaa 420
gacaaagaca agcattcacg cccgaatgat tggaccgttc ctaagggttg ctttatgact 480
agcgttgccg acaaatcgcg cttcacgaac gtcaaacagt tcgtggcacc cgaaacgtca 540
gaaggtgtgt cgttacttct tggcaacaca aaggatttca ttattagctt tgatttaaaa 600
ttcctgacga atgggtcagt atccgtagtc ctagaaacca cggagaaaaa tcagctcttt 660
accgtacact atatctcgaa tacgcagtta atcgcattta aagaacgcga catttactat 720
ggcatcggtc cgcgaacatc gtggagcact gtcactcggg atctggtgac ggatttacgc 780
aaaggcgttg gtctcagtaa caccaaggca gtcaagcaga ccaaaattat gccgaaaaaa 840
gtggtacggc tgattgccaa aggcaaaggc tttctggata acatcaccat ctctaccact 900
gcccatatgg cagcgttttt cgctgcaagc cactggttag tgaccaatca agacgaaaaa 960
ggcggatggc cgatcatggt gacgcgcaaa ctgggtgaag gttttcgcgc acttgaacct 1020
ggttggtatt ccgcgatggc tcagggtcag gcgatttcta ccttggttcg cgcatatctc 1080
ttgaccaagg atcatgtctt cttggatagt gcgttgcgag ccaccgcgcc gtacaaattt 1140
ctgtctgaac aacatggcgt gaaagccgtc tttatgaaca agtatgactg gtatgaagag 1200
tatccgacca caccgagcag ttttgtgctg aatggtttca tgtattccct gattggcctc 1260
tatgacctga aagaaacagc tggtgagaaa ctgggaaaag aagcgcgtct gctgtacgaa 1320
cgtggcatgg aaagtttgaa agccatgctc ccactgtacg ataccggtag tggcaccatt 1380
tacgatctgc gtcacttcat gctggggagt gcgccgaatc tggcacgttg ggattatcat 1440
acgactcaca tcaatcagct gcaattgctg agcaccattg atgaagcgcc agtttttcgc 1500
gagttcgtca aacgctggaa aagctacctg aaaggctctc gcgcgaaaca caac 1554

<210> SEQ ID NO 9
<211> LENGTH: 518
<212> TYPE: PRT
<213> ORGANISM: Monodelphis domestica

<400> SEQUENCE: 9

Gly Leu Lys Tyr Glu Glu Ile Asp Cys Leu Ile Asn Asp Glu His Thr
1 5 10 15

Ile Lys Gly Arg Arg Glu Gly Asn Glu Ile Phe Leu Pro Phe Thr Trp
20 25 30

Val Glu Lys Tyr Phe Glu Val Tyr Gly Lys Met Val Gln Tyr Asp Gly
35 40 45

Tyr Asp Arg Phe Glu Phe Ser His Ser Tyr Ser Lys Val Tyr Ala Gln
50 55 60

-continued

```
Arg Ala Pro Tyr His Pro Asp Gly Val Phe Met Ser Phe Glu Gly Tyr
65                  70                  75                  80

Asn Val Glu Val Arg Asp Arg Val Lys Cys Ile Ser Gly Val Glu Gly
                85                  90                  95

Val Pro Leu Ser Thr Gln Trp Gly Pro Gln Gly Tyr Phe Tyr Pro Ile
            100                 105                 110

Gln Ile Ala Gln Tyr Gly Leu Ser His Tyr Ser Lys Asn Leu Thr Glu
        115                 120                 125

Lys Pro Pro His Ile Glu Val Tyr Glu Thr Ala Glu Asp Lys Asp Lys
    130                 135                 140

His Ser Arg Pro Asn Asp Trp Thr Val Pro Lys Gly Cys Phe Met Thr
145                 150                 155                 160

Ser Val Ala Asp Lys Ser Arg Phe Thr Asn Val Lys Gln Phe Val Ala
                165                 170                 175

Pro Glu Thr Ser Glu Gly Val Ser Leu Leu Leu Gly Asn Thr Lys Asp
            180                 185                 190

Phe Ile Ile Ser Phe Asp Leu Lys Phe Leu Thr Asn Gly Ser Val Ser
        195                 200                 205

Val Val Leu Glu Thr Thr Glu Lys Asn Gln Leu Phe Thr Val His Tyr
    210                 215                 220

Ile Ser Asn Thr Gln Leu Ile Ala Phe Lys Glu Arg Asp Ile Tyr Tyr
225                 230                 235                 240

Gly Ile Gly Pro Arg Thr Ser Trp Ser Thr Val Thr Arg Asp Leu Val
                245                 250                 255

Thr Asp Leu Arg Lys Gly Val Gly Leu Ser Asn Thr Lys Ala Val Lys
            260                 265                 270

Gln Thr Lys Ile Met Pro Lys Lys Val Val Arg Leu Ile Ala Lys Gly
        275                 280                 285

Lys Gly Phe Leu Asp Asn Ile Thr Ile Ser Thr Thr Ala His Met Ala
    290                 295                 300

Ala Phe Phe Ala Ala Ser His Trp Leu Val Thr Asn Gln Asp Glu Lys
305                 310                 315                 320

Gly Gly Trp Pro Ile Met Val Thr Arg Lys Leu Gly Glu Gly Phe Arg
                325                 330                 335

Ala Leu Glu Pro Gly Trp Tyr Ser Ala Met Ala Gln Gly Gln Ala Ile
            340                 345                 350

Ser Thr Leu Val Arg Ala Tyr Leu Leu Thr Lys Asp His Val Phe Leu
        355                 360                 365

Asp Ser Ala Leu Arg Ala Thr Ala Pro Tyr Lys Phe Leu Ser Glu Gln
    370                 375                 380

His Gly Val Lys Ala Val Phe Met Asn Lys Tyr Asp Trp Tyr Glu Glu
385                 390                 395                 400

Tyr Pro Thr Thr Pro Ser Ser Phe Val Leu Asn Gly Phe Met Tyr Ser
                405                 410                 415

Leu Ile Gly Leu Tyr Asp Leu Lys Glu Thr Ala Gly Glu Lys Leu Gly
            420                 425                 430

Lys Glu Ala Arg Leu Leu Tyr Glu Arg Gly Met Glu Ser Leu Lys Ala
        435                 440                 445

Met Leu Pro Leu Tyr Asp Thr Gly Ser Gly Thr Ile Tyr Asp Leu Arg
    450                 455                 460

His Phe Met Leu Gly Ser Ala Pro Asn Leu Ala Arg Trp Asp Tyr His
465                 470                 475                 480
```

-continued

```
Thr Thr His Ile Asn Gln Leu Gln Leu Leu Ser Thr Ile Asp Glu Ala
                485                 490                 495

Pro Val Phe Arg Glu Phe Val Lys Arg Trp Lys Ser Tyr Leu Lys Gly
            500                 505                 510

Ser Arg Ala Lys His Asn
        515
```

<210> SEQ ID NO 10
<211> LENGTH: 1557
<212> TYPE: DNA
<213> ORGANISM: Gallus gallus

<400> SEQUENCE: 10

```
ggattgaaat acgaagaaat tgactgcctg attaacgatg aacataccat taagggccgt     60

cgggagggct cggaggtatt cctcccgttt tcatgggtgg aaaagtattt cgaagtgtat    120

ggcaaaattg cccagtatga tggttatgac cgctttgaat ttagccacag ttattcgaaa    180

gtctataccc aacgcgcacc ctaccatcct gatggggtgt ttatgtcgtt tgagggttat    240

aacgtcgaag tacgcgatcg tgtcaaatgc atcagcggcg tagaaggtgt gcccctgagc    300

actcagtggg gtccgcaagg ttacttctac cctatccaga tcgcccagta cggcttgtct    360

cattatagta agaacctgac tgagaaacca ccgcatattg aagtctatga aactgcggaa    420

gaaaaggatc gcggttcccg tgcggcggag tggacagtgc cgaagggctg cagtctgtcc    480

accgtccccg acaaagcgaa atttacctcc gtgaaacact ttgttgcacc agagaatacc    540

gagggcgtat ctctgcagct tgggaatgct cgcgacttta tcatctcctt tgacttaaaa    600

ttggtgacga atggttccat ttctgtggtg ctggaaacga cggaaaagaa ccaactgttc    660

acggtgcact atgtctcaaa tacgcagctc attgcctttc gtgagcgcga tatttactat    720

ggcatcggag cgcgtacgag ttggtcaaca atcacccgtg acctggttac cgatctgcgg    780

aaaggcgtcg ggctgagcaa caccaaagcc gttaaacaaa cgcggattat gccgaagaaa    840

gttgtccgct taatcgcaaa aggacgcggt tttctggaca acgttactat ttccgctaca    900

gcgcatatgg ctgctttctt tgcggcgagt aattggctgg ttcgcaatca ggatgaacgc    960

ggtgggtggc cgattatggt gacccgcaag ttaggagaag gttttcgctc tttggatcca   1020

ggttggtact cggcgatggc ccaaggtcag gcaatttcaa ctctggttcg cgcttatctg   1080

ctgacaaaag aacacgcatt tctgagctct gcccttcgtg ccaccgcgcc ctataaactc   1140

ccgtctgaac agcatggcgt gaaagccgtc tttatgaacc gtcatgattg gtacgaagag   1200

tatcctacgt cgcctagcag tttcgtgttg aatggcttca tgtatagcct gattgggctc   1260

tacgacttaa aagaaaccgc gggcgagaaa cttggcaaag aggcgcgctt actgtacgaa   1320

cgcggtatgg aaagccttaa agcgatgctg ccgttatatg acaccgggtc gggcaccatc   1380

tacgatttgc gccatttcat gctgggcaca gctccgaatc ttgcgcggtg ggattatcac   1440

acgacccaca ttaaccaatt gcagctgctg tcgaccatcg atgaagcccc aatcttcaaa   1500

gagtttgtgc gtcgttggaa aagctactta cgtggtggtc gtgcgaaaca taactaa      1557
```

<210> SEQ ID NO 11
<211> LENGTH: 518
<212> TYPE: PRT
<213> ORGANISM: Gallus gallus

<400> SEQUENCE: 11

```
Gly Leu Lys Tyr Glu Glu Ile Asp Cys Leu Ile Asn Asp Glu His Thr
1               5                   10                  15
```

-continued

```
Ile Lys Gly Arg Arg Glu Gly Ser Glu Val Phe Leu Pro Phe Ser Trp
            20                  25                  30

Val Glu Lys Tyr Phe Glu Val Tyr Gly Lys Ile Ala Gln Tyr Asp Gly
        35                  40                  45

Tyr Asp Arg Phe Glu Phe Ser His Ser Tyr Ser Lys Val Tyr Thr Gln
    50                  55                  60

Arg Ala Pro Tyr His Pro Asp Gly Val Phe Met Ser Phe Glu Gly Tyr
65                  70                  75                  80

Asn Val Glu Val Arg Asp Arg Val Lys Cys Ile Ser Gly Val Glu Gly
                85                  90                  95

Val Pro Leu Ser Thr Gln Trp Gly Pro Gln Gly Tyr Phe Tyr Pro Ile
            100                 105                 110

Gln Ile Ala Gln Tyr Gly Leu Ser His Tyr Ser Lys Asn Leu Thr Glu
        115                 120                 125

Lys Pro Pro His Ile Glu Val Tyr Glu Thr Ala Glu Glu Lys Asp Arg
    130                 135                 140

Gly Ser Arg Ala Ala Glu Trp Thr Val Pro Lys Gly Cys Ser Leu Ser
145                 150                 155                 160

Thr Val Pro Asp Lys Ala Lys Phe Thr Ser Val Lys His Phe Val Ala
                165                 170                 175

Pro Glu Asn Thr Glu Gly Val Ser Leu Gln Leu Gly Asn Ala Arg Asp
            180                 185                 190

Phe Ile Ile Ser Phe Asp Leu Lys Leu Val Thr Asn Gly Ser Ile Ser
        195                 200                 205

Val Val Leu Glu Thr Thr Glu Lys Asn Gln Leu Phe Thr Val His Tyr
    210                 215                 220

Val Ser Asn Thr Gln Leu Ile Ala Phe Arg Glu Arg Asp Ile Tyr Tyr
225                 230                 235                 240

Gly Ile Gly Ala Arg Thr Ser Trp Ser Thr Ile Thr Arg Asp Leu Val
                245                 250                 255

Thr Asp Leu Arg Lys Gly Val Gly Leu Ser Asn Thr Lys Ala Val Lys
            260                 265                 270

Gln Thr Arg Ile Met Pro Lys Lys Val Val Arg Leu Ile Ala Lys Gly
        275                 280                 285

Arg Gly Phe Leu Asp Asn Val Thr Ile Ser Ala Thr Ala His Met Ala
    290                 295                 300

Ala Phe Phe Ala Ala Ser Asn Trp Leu Val Arg Asn Gln Asp Glu Arg
305                 310                 315                 320

Gly Gly Trp Pro Ile Met Val Thr Arg Lys Leu Gly Glu Gly Phe Arg
                325                 330                 335

Ser Leu Asp Pro Gly Trp Tyr Ser Ala Met Ala Gln Gly Gln Ala Ile
            340                 345                 350

Ser Thr Leu Val Arg Ala Tyr Leu Leu Thr Lys Glu His Ala Phe Leu
        355                 360                 365

Ser Ser Ala Leu Arg Ala Thr Ala Pro Tyr Lys Leu Pro Ser Glu Gln
    370                 375                 380

His Gly Val Lys Ala Val Phe Met Asn Arg His Asp Trp Tyr Glu Glu
385                 390                 395                 400

Tyr Pro Thr Ser Pro Ser Ser Phe Val Leu Asn Gly Phe Met Tyr Ser
                405                 410                 415

Leu Ile Gly Leu Tyr Asp Leu Lys Glu Thr Ala Gly Glu Lys Leu Gly
            420                 425                 430
```

-continued

```
Lys Glu Ala Arg Leu Leu Tyr Glu Arg Gly Met Glu Ser Leu Lys Ala
        435                 440                 445

Met Leu Pro Leu Tyr Asp Thr Gly Ser Gly Thr Ile Tyr Asp Leu Arg
    450                 455                 460

His Phe Met Leu Gly Thr Ala Pro Asn Leu Ala Arg Trp Asp Tyr His
465                 470                 475                 480

Thr Thr His Ile Asn Gln Leu Gln Leu Leu Ser Thr Ile Asp Glu Ala
                485                 490                 495

Pro Ile Phe Lys Glu Phe Val Arg Arg Trp Lys Ser Tyr Leu Arg Gly
            500                 505                 510

Gly Arg Ala Lys His Asn
        515


<210> SEQ ID NO 12
<211> LENGTH: 1548
<212> TYPE: DNA
<213> ORGANISM: Xenopus tropicalis

<400> SEQUENCE: 12

ggtcagaaat acgaagaaat tgattgtatg attaatgaag aacagactgt caggtgtcgc     60

aaagaaggca ccgaagtgta catgccgttt tcgtgggttg agaaatactt tgaagtgtat    120

ggcaaaatcg cccaatatga cggctttgaa cgcttcgagt tctcgcacag ttatagcaaa    180

gtctatgccc aacgtgggcc ctatcatcca gatggcgtgt tcatgagctt tgaaggctac    240

aatgtggaag ttcgtgatcg tgttaagtgc atcagtggcg ttgaaggcgt tccgctgagc    300

actcaatggg gtccgcaggg ctatttctac ccgattcaga ttgcgcagta tggcttatcc    360

cactactcaa aaaacctgac ggaaaaaccc ccgcatgtag aagtatatga gaaagcggat    420

gagaaatccg gagttacggg ggtatggaag attccgaaag gcgctagcgt caccaccgtc    480

tttgattcaa cgaaaaattc gcatgtgaag cattttgttg tcccggagaa cttagaaggg    540

gcgtctttga ccctgggtaa cattaaagac ttcatccttt ctctggatgt gaagttcacc    600

accaacggct ccataagcgt tgtgatggaa accacggaga aaaatcagat cttcaccgtg    660

cactacatta ccaacaccca gctgattgcc tttcgcgatc atgacgtttt ttacggcttg    720

ggtagcagaa cggcatggtc aacgctgaca cgcgatttag tgaccgacct gaagaaaggt    780

gtaggccttt cgaacactaa agcggtcaaa cagaccaaga tcatgccgaa aaaagtggtg    840

cagattgtcc tgaaaggcag tggatacctg gataatgtga cgatttcaac cacagcccat    900

acggcagcct tttttgctgc gagtgattgg ttggtgcgga atcaagacac aaaaggtggt    960

tggccgatca tggtaacgcg aaaactgggt gatggattca aagccctgga acctggctgg   1020

tatagtgcaa tggcgcaagg tcaggcgatt agcacactgg tccgtgcgta tttactcacc   1080

aaggagcaat tctacctcga ttccgctctg cgcgccacag ccccctttaa acttccgagt   1140

gaaaagcacg gtgtcaaagc agtctttatg aacaaatatg attggtatga ggagtatccg   1200

acgacgccat cgagctttgt gctgaatggg ttcatatatg cattactggg cctgtacgat   1260

ctcaaagaaa ccgccggtga gaaacaggga aaagaagcgc gtctcctgta tgaacgcggt   1320

atggagagtt tgcgtgcgat gttacccctg tatgacaccg gttcagggtc tatctatgac   1380

ctgcgccatg ttatgctggg cactgcgcct aatttggctc gttgggacta ccataccact   1440

cacatcaacc agcttcagct ccttgccagc atggatggtt cgccgatctt tcgcgacttc   1500

attcgtcgct ggaagtctta tctgaaaggc gggcgagcaa agcataac                 1548
```

<210> SEQ ID NO 13
<211> LENGTH: 516
<212> TYPE: PRT
<213> ORGANISM: Xenopus tropicalis

<400> SEQUENCE: 13

```
Gly Gln Lys Tyr Glu Glu Ile Asp Cys Met Ile Asn Glu Glu Gln Thr
1               5                   10                  15

Val Arg Cys Arg Lys Glu Gly Thr Glu Val Tyr Met Pro Phe Ser Trp
            20                  25                  30

Val Glu Lys Tyr Phe Glu Val Tyr Gly Lys Ile Ala Gln Tyr Asp Gly
        35                  40                  45

Phe Glu Arg Phe Glu Phe Ser His Ser Tyr Ser Lys Val Tyr Ala Gln
    50                  55                  60

Arg Gly Pro Tyr His Pro Asp Gly Val Phe Met Ser Phe Glu Gly Tyr
65                  70                  75                  80

Asn Val Glu Val Arg Asp Arg Val Lys Cys Ile Ser Gly Val Glu Gly
                85                  90                  95

Val Pro Leu Ser Thr Gln Trp Gly Pro Gln Gly Tyr Phe Tyr Pro Ile
            100                 105                 110

Gln Ile Ala Gln Tyr Gly Leu Ser His Tyr Ser Lys Asn Leu Thr Glu
        115                 120                 125

Lys Pro Pro His Val Glu Val Tyr Glu Lys Ala Asp Glu Lys Ser Gly
    130                 135                 140

Val Thr Gly Val Trp Lys Ile Pro Lys Gly Ala Ser Val Thr Thr Val
145                 150                 155                 160

Phe Asp Ser Thr Lys Asn Ser His Val Lys His Phe Val Val Pro Glu
                165                 170                 175

Asn Leu Glu Gly Ala Ser Leu Thr Leu Gly Asn Ile Lys Asp Phe Ile
            180                 185                 190

Leu Ser Leu Asp Val Lys Phe Thr Thr Asn Gly Ser Ile Ser Val Val
        195                 200                 205

Met Glu Thr Thr Glu Lys Asn Gln Ile Phe Thr Val His Tyr Ile Thr
    210                 215                 220

Asn Thr Gln Leu Ile Ala Phe Arg Asp His Asp Val Phe Tyr Gly Leu
225                 230                 235                 240

Gly Ser Arg Thr Ala Trp Ser Thr Leu Thr Arg Asp Leu Val Thr Asp
                245                 250                 255

Leu Lys Lys Gly Val Gly Leu Ser Asn Thr Lys Ala Val Lys Gln Thr
            260                 265                 270

Lys Ile Met Pro Lys Lys Val Val Gln Ile Val Leu Lys Gly Ser Gly
        275                 280                 285

Tyr Leu Asp Asn Val Thr Ile Ser Thr Thr Ala His Thr Ala Ala Phe
    290                 295                 300

Phe Ala Ala Ser Asp Trp Leu Val Arg Asn Gln Asp Thr Lys Gly Gly
305                 310                 315                 320

Trp Pro Ile Met Val Thr Arg Lys Leu Gly Asp Gly Phe Lys Ala Leu
                325                 330                 335

Glu Pro Gly Trp Tyr Ser Ala Met Ala Gln Gly Gln Ala Ile Ser Thr
            340                 345                 350

Leu Val Arg Ala Tyr Leu Leu Thr Lys Glu Gln Phe Tyr Leu Asp Ser
        355                 360                 365

Ala Leu Arg Ala Thr Ala Pro Phe Lys Leu Pro Ser Glu Lys His Gly
    370                 375                 380
```

-continued

Val Lys Ala Val Phe Met Asn Lys Tyr Asp Trp Tyr Glu Glu Tyr Pro
385 390 395 400

Thr Thr Pro Ser Ser Phe Val Leu Asn Gly Phe Ile Tyr Ala Leu Leu
405 410 415

Gly Leu Tyr Asp Leu Lys Glu Thr Ala Gly Glu Lys Gln Gly Lys Glu
420 425 430

Ala Arg Leu Leu Tyr Glu Arg Gly Met Glu Ser Leu Arg Ala Met Leu
435 440 445

Pro Leu Tyr Asp Thr Gly Ser Gly Ser Ile Tyr Asp Leu Arg His Val
450 455 460

Met Leu Gly Thr Ala Pro Asn Leu Ala Arg Trp Asp Tyr His Thr Thr
465 470 475 480

His Ile Asn Gln Leu Gln Leu Leu Ala Ser Met Asp Gly Ser Pro Ile
485 490 495

Phe Arg Asp Phe Ile Arg Arg Trp Lys Ser Tyr Leu Lys Gly Gly Arg
500 505 510

Ala Lys His Asn
515

<210> SEQ ID NO 14
<211> LENGTH: 1638
<212> TYPE: DNA
<213> ORGANISM: Ciona intestinalis

<400> SEQUENCE: 14
aaaccgtctg ttagtgccat tgaatgcctg atcaatgatg aagaaacggt acaatgcctc 60
aagagctcag attcaaatgc gcagatctat atgccatttg atttcatcca gaactacttt 120
gatgtctatg gcaaaatgaa gcattatgat ggttacgatc gctttgagtt ccagcagagc 180
aacgcgaaag tggtttacga tccgaaaagc ccgtatacct ataccggggt ctttatgacc 240
tttgactcgt acaacgtcga agcccgtgaa cgggtgaaat gcattagcgg cattaccggg 300
gttccgctga gtacgcaatg gcacattgaa gggtattatt acggcattca gatagcacag 360
ttcggcatgt ctcactatag caaacacatg acacagaaac cgccgaccaa acaagtgtat 420
gaaaacgccg aaggttctgt tcagtcacgg tggagcagct ctaacaaata ctgtctggtt 480
gaaaacgagg aggacaagga acgcaattca cgtgttatca agttttcgac tcctgatagc 540
attcccttgg gtagcggagc ctctttggtg ttgggcaata ccatggaatt tatcctgtct 600
ttcgacctga aaatggtggc gaatggttcg ttgagcgttg tgctggagac gaacgacaaa 660
atgaaacagt acacgattca ttacatcacg aattccctcg ttattgatta tgatttaaag 720
tccaacatct attatggcat tggcccatca cgtacatggc gacatatggc gagagacctt 780
cttaccgatc tgaaaaaagg catcggcttg acgaccaaaa aacaggcgaa aaaggtgcgt 840
attgcaatcc agaaagtgtc ccgtttaatc gtgcgtggtc gtggctacat tgacaacgtg 900
acgctgtcga cgtcggaaca cctgacccag ttctttgatg ctagccaatg gatgtacctg 960
aaccaagata agaaaactgg aggttggaaa aatgacgttg aacgtcgatt ggaaggttat 1020
cccccgattc cagcagggtg gatttcagcg atgggacaag gccaaggtat gtccgtatta 1080
agtcgcgctt atcacgtctt tcatgacccg aagtacattg tcgctctgtc ccatgcatta 1140
cagccgttta cgaaatcctc ggaacaggga ggtgtccgcg caaccttttt gaaaacttat 1200
acttggtatg aggagtatcc gactaaaccg agtagtttcg ttctgaatgg cttcatgtat 1260
tccctgatag gcctctatga ctttaaaagc ctcctggaac atgagtttgg ctttgggagt 1320

-continued

```
aacgaacagc cgccgaaagt gtcgttgcaa atctcgagcg tagatctgcc tgccacctac   1380

aaactggtga aacagcttta ccacgatggt atgacatccc taaaagcgat gctcccctta   1440

tacgatggtg gttctcgcac attctacgat ctgcgccatt tcattctggg gatgccgcct   1500

aatgtggcta ggtgggatta tcataccacc catctctcac aactggtact tctgtattct   1560

gtgagtaatg aacctgtcct aaaaaaatac ttcgataact ggagtggcta tttacgtggc   1620

aaagtcgcga aacataat                                                 1638


<210> SEQ ID NO 15
<211> LENGTH: 546
<212> TYPE: PRT
<213> ORGANISM: Ciona intestinalis

<400> SEQUENCE: 15

Lys Pro Ser Val Ser Ala Ile Glu Cys Leu Ile Asn Asp Glu Glu Thr
1               5                   10                  15

Val Gln Cys Leu Lys Ser Ser Asp Ser Asn Ala Gln Ile Tyr Met Pro
            20                  25                  30

Phe Asp Phe Ile Gln Asn Tyr Phe Asp Val Tyr Gly Lys Met Lys His
        35                  40                  45

Tyr Asp Gly Tyr Asp Arg Phe Glu Phe Gln Gln Ser Asn Ala Lys Val
    50                  55                  60

Val Tyr Asp Pro Lys Ser Pro Tyr Thr Tyr Thr Gly Val Phe Met Thr
65                  70                  75                  80

Phe Asp Ser Tyr Asn Val Glu Ala Arg Glu Arg Val Lys Cys Ile Ser
                85                  90                  95

Gly Ile Thr Gly Val Pro Leu Ser Thr Gln Trp His Ile Glu Gly Tyr
            100                 105                 110

Tyr Tyr Gly Ile Gln Ile Ala Gln Phe Gly Met Ser His Tyr Ser Lys
        115                 120                 125

His Met Thr Gln Lys Pro Pro Thr Lys Gln Val Tyr Glu Asn Ala Glu
    130                 135                 140

Gly Ser Val Gln Ser Arg Trp Ser Ser Ser Asn Lys Tyr Cys Leu Val
145                 150                 155                 160

Glu Asn Glu Glu Asp Lys Glu Arg Asn Ser Arg Val Ile Lys Phe Ser
                165                 170                 175

Thr Pro Asp Ser Ile Pro Leu Gly Ser Gly Ala Ser Leu Val Leu Gly
            180                 185                 190

Asn Thr Met Glu Phe Ile Leu Ser Phe Asp Leu Lys Met Val Ala Asn
        195                 200                 205

Gly Ser Leu Ser Val Val Leu Glu Thr Asn Asp Lys Met Lys Gln Tyr
    210                 215                 220

Thr Ile His Tyr Ile Thr Asn Ser Leu Val Ile Asp Tyr Asp Leu Lys
225                 230                 235                 240

Ser Asn Ile Tyr Tyr Gly Ile Gly Pro Ser Arg Thr Trp Arg His Met
                245                 250                 255

Ala Arg Asp Leu Leu Thr Asp Leu Lys Lys Gly Ile Gly Leu Thr Thr
            260                 265                 270

Lys Lys Gln Ala Lys Lys Val Arg Ile Ala Ile Gln Lys Val Ser Arg
        275                 280                 285

Leu Ile Val Arg Gly Arg Gly Tyr Ile Asp Asn Val Thr Leu Ser Thr
    290                 295                 300

Ser Glu His Leu Thr Gln Phe Phe Asp Ala Ser Gln Trp Met Tyr Leu
305                 310                 315                 320
```

```
Asn Gln Asp Lys Lys Thr Gly Gly Trp Lys Asn Asp Val Glu Arg Arg
                325                 330                 335

Leu Glu Gly Tyr Pro Pro Ile Pro Ala Gly Trp Ile Ser Ala Met Gly
            340                 345                 350

Gln Gly Gln Gly Met Ser Val Leu Ser Arg Ala Tyr His Val Phe His
        355                 360                 365

Asp Pro Lys Tyr Ile Val Ala Leu Ser His Ala Leu Gln Pro Phe Thr
    370                 375                 380

Lys Ser Ser Glu Gln Gly Gly Val Arg Ala Thr Phe Leu Lys Thr Tyr
385                 390                 395                 400

Thr Trp Tyr Glu Glu Tyr Pro Thr Lys Pro Ser Ser Phe Val Leu Asn
                405                 410                 415

Gly Phe Met Tyr Ser Leu Ile Gly Leu Tyr Asp Phe Lys Ser Leu Leu
            420                 425                 430

Glu His Glu Phe Gly Phe Gly Ser Asn Glu Gln Pro Pro Lys Val Ser
        435                 440                 445

Leu Gln Ile Ser Ser Val Asp Leu Pro Ala Thr Tyr Lys Leu Val Lys
    450                 455                 460

Gln Leu Tyr His Asp Gly Met Thr Ser Leu Lys Ala Met Leu Pro Leu
465                 470                 475                 480

Tyr Asp Gly Gly Ser Arg Thr Phe Tyr Asp Leu Arg His Phe Ile Leu
                485                 490                 495

Gly Met Pro Pro Asn Val Ala Arg Trp Asp Tyr His Thr Thr His Leu
            500                 505                 510

Ser Gln Leu Val Leu Leu Tyr Ser Val Ser Asn Glu Pro Val Leu Lys
        515                 520                 525

Lys Tyr Phe Asp Asn Trp Ser Gly Tyr Leu Arg Gly Lys Val Ala Lys
    530                 535                 540

His Asn
545
```

<210> SEQ ID NO 16
<211> LENGTH: 1646
<212> TYPE: DNA
<213> ORGANISM: Drosophila melanogaster

<400> SEQUENCE: 16

```
tatatgcgct gtgcagcgtt cagcttttca cccgatttcg tacgccctct tgatcgcagc      60

gcccgtcaat cgagttctgg tggtgaagcg actgccctgc acgatatcga atgctcgatc     120

aatcaggaat ataccgtgca ttgtaagcgc gatgaaaacg ctaacgaagt gtatgtccct     180

tttagcttct tgcggaatta ctttgatgtc tcgggcgccg tatcaactaa ctcaaacgaa     240

gtagcgaaat ttaactgggt ccattctacc gcgaaagtga accttccccg tggcaaatat     300

gacgcacgcg gtgtgtacat gtattttgag aattacaatg ttgaggtacg cgaccgtgtt     360

aaatgcatta gcgctgcgga aggcgttcca gtgtccaccc aatgggagaa acgcggttac     420

ttctacccga cccagattgc acagttcgcc ttgtcacatt atagcaagaa tctgacagaa     480

ccagccccgc gtgtgcgcgt tctggaagat ggtgacggga atcagatgga gtggtctacc     540

ccgaaaacct caaacatgac ccgcatttgg caccacaaat ttaacaccag tgtggttcag     600

ttcgaaacgg caccaggtta tgagggagtc attagcatcg ccctgaacca gaccctggat     660

ctgttactca gcgtggatct tttactggtc accaacagta gcagtttgat gatcacggtt     720

cagaatcggg acactcgcca taactactcc ttacactaca tcccagcgga cttactgctg     780
```

agtgtgcagg acacaaacat ctactatggg ctgggcggct cggcccttaa caaatggcgc 840
cacattaccc gcgatctgca tattgactta cagaaaggaa ttatgggtga taaacgcagt 900
ccgctcaaaa tccgccgctc tgatctggag gtgatcagca ttggttttct gggcctgggc 960
ttctttgaca atattactct gtccacgtct gatcatctgg cccactttta tgatgctgcg 1020
gagtggtttg tacacaacca ggatcctaaa acgggaggtt ggacaaatcc ggtacgtcgt 1080
tccctgaatg ggtttgctga actgcgtcca ggctggatct ctgccatggg ccagggtcat 1140
gcgatctccg ttttagcgcg tgcttactgg cattcgggtg gggatgaacg ctacctccgc 1200
gcggcagcgg ctgggcttca accgtatcgt gtatattcgc gcgatggagg cgtcctcgcg 1260
caattcatgg acaagttcta ttggtacgaa gaatatccga cgactccgcc cagttatgtt 1320
ctgaacggct ttatctacag cttgctgggc ttgtatgatc ttaatagcac ggccccggga 1380
aagattgctc gtgaggcggg caaactgttt gcacaaggca tgcatagcct gaagaaaatg 1440
ctgttactct tcgacaccgg ttcggggacg tcttatgatt tacgccacct gagcctgggt 1500
gttgcaccca acctcgcacg ttgggactat cacgctaccc atgttaatca gctgttgctg 1560
ctcgcgacga ttgactcgga tccgctgatt gcccagaccg cggaacgctg gaaaggttac 1620
atgtttgtcg tgccaagcat aattaa 1646

<210> SEQ ID NO 17
<211> LENGTH: 549
<212> TYPE: PRT
<213> ORGANISM: Drosophila melanogaster

<400> SEQUENCE: 17

Tyr Met Arg Cys Ala Ala Phe Ser Phe Ser Pro Asp Phe Val Arg Pro
1 5 10 15

Leu Asp Arg Ser Ala Arg Gln Ser Ser Ser Gly Gly Glu Ala Thr Ala
20 25 30

Leu His Asp Ile Glu Cys Ser Ile Asn Gln Glu Tyr Thr Val His Cys
35 40 45

Lys Arg Asp Glu Asn Ala Asn Glu Val Tyr Val Pro Phe Ser Phe Leu
50 55 60

Arg Asn Tyr Phe Asp Val Ser Gly Ala Val Ser Thr Asn Ser Asn Glu
65 70 75 80

Val Ala Lys Phe Asn Trp Val His Ser Thr Ala Lys Val Asn Leu Pro
85 90 95

Arg Gly Lys Tyr Asp Ala Arg Gly Val Tyr Met Tyr Phe Glu Asn Tyr
100 105 110

Asn Val Glu Val Arg Asp Arg Val Lys Cys Ile Ser Ala Ala Glu Gly
115 120 125

Val Pro Val Ser Thr Gln Trp Glu Lys Arg Gly Tyr Phe Tyr Pro Thr
130 135 140

Gln Ile Ala Gln Phe Ala Leu Ser His Tyr Ser Lys Asn Leu Thr Glu
145 150 155 160

Pro Ala Pro Arg Val Arg Val Leu Glu Asp Gly Asp Gly Asn Gln Met
165 170 175

Glu Trp Ser Thr Pro Lys Thr Ser Asn Met Thr Arg Ile Trp His His
180 185 190

Lys Phe Asn Thr Ser Val Val Gln Phe Glu Thr Ala Pro Gly Tyr Glu
195 200 205

Gly Val Ile Ser Ile Ala Leu Asn Gln Thr Leu Asp Leu Leu Leu Ser

-continued

```
    210                 215                 220

Val Asp Leu Leu Leu Val Thr Asn Ser Ser Ser Leu Met Ile Thr Val
225                 230                 235                 240

Gln Asn Arg Asp Thr Arg His Asn Tyr Ser Leu His Tyr Ile Pro Ala
                245                 250                 255

Asp Leu Leu Leu Ser Val Gln Asp Thr Asn Ile Tyr Tyr Gly Leu Gly
            260                 265                 270

Gly Ser Ala Leu Asn Lys Trp Arg His Ile Thr Arg Asp Leu His Ile
        275                 280                 285

Asp Leu Gln Lys Gly Ile Met Gly Asp Lys Arg Ser Pro Leu Lys Ile
    290                 295                 300

Arg Arg Ser Asp Leu Glu Val Ile Ser Ile Gly Phe Leu Gly Leu Gly
305                 310                 315                 320

Phe Phe Asp Asn Ile Thr Leu Ser Thr Ser Asp His Leu Ala His Phe
                325                 330                 335

Tyr Asp Ala Ala Glu Trp Phe Val His Asn Gln Asp Pro Lys Thr Gly
            340                 345                 350

Gly Trp Thr Asn Pro Val Arg Arg Ser Leu Asn Gly Phe Ala Glu Leu
        355                 360                 365

Arg Pro Gly Trp Ile Ser Ala Met Gly Gln Gly His Ala Ile Ser Val
    370                 375                 380

Leu Ala Arg Ala Tyr Trp His Ser Gly Gly Asp Glu Arg Tyr Leu Arg
385                 390                 395                 400

Ala Ala Ala Ala Gly Leu Gln Pro Tyr Arg Val Tyr Ser Arg Asp Gly
                405                 410                 415

Gly Val Leu Ala Gln Phe Met Asp Lys Phe Tyr Trp Tyr Glu Glu Tyr
            420                 425                 430

Pro Thr Thr Pro Pro Ser Tyr Val Leu Asn Gly Phe Ile Tyr Ser Leu
        435                 440                 445

Leu Gly Leu Tyr Asp Leu Asn Ser Thr Ala Pro Gly Lys Ile Ala Arg
    450                 455                 460

Glu Ala Gly Lys Leu Phe Ala Gln Gly Met His Ser Leu Lys Lys Met
465                 470                 475                 480

Leu Leu Leu Phe Asp Thr Gly Ser Gly Thr Ser Tyr Asp Leu Arg His
                485                 490                 495

Leu Ser Leu Gly Val Ala Pro Asn Leu Ala Arg Trp Asp Tyr His Ala
            500                 505                 510

Thr His Val Asn Gln Leu Leu Leu Leu Ala Thr Ile Asp Ser Asp Pro
        515                 520                 525

Leu Ile Ala Gln Thr Ala Glu Arg Trp Lys Gly Tyr Met Phe Gly Arg
    530                 535                 540

Arg Ala Lys His Asn
545


<210> SEQ ID NO 18
<211> LENGTH: 1851
<212> TYPE: DNA
<213> ORGANISM: Caenorhabditis elegans

<400> SEQUENCE: 18

atgaaatgct tgcgttggcg gagtaaccgc catcgcatct atcttcttgt ggcatgtggc      60

gcccttttc tgctgaatcg ccatctgact caggaagaat ctcgcatcga tgaagaagac     120

gaggaattaa cccaggtgga cgtcaacgag gatgacaaaa agatagaatg cgaaccacca     180
```

-continued

```
ggctctatcg aatcgaagtg cattgcggac aacgggaaga gcatgaagtg ctggaaagac    240

gaagaggatg tgtatttccc ggtatcgtat ctgaaaaaac gctttgacat gactggtaaa    300

ctcggcaaag atggtagcac gttcgaactg tatacgtcat acgccaagat gcgtagtccg    360

gatagtacct atgacccgct aggacccttt gggcacttta gcacctactc agttgaaacc    420

cgtgatcgtg tgcgttgtgt cagtgccaaa accgacgttc ccatgtccac acaatgggat    480

ccgatcccgt attattaccc tattcagatt agccagtatg gtctgcaaca ctatagccgt    540

atgaaactgg attcgatctc gaataaatcc gaagcaagcc ccaaagacga tgtcattctg    600

ggagtgaaca gcaaagaatg gaaaggtgct gctggtatgc acgagactac ggaacgcctg    660

ttctttaacg atgagcagat gggcaaagtc gtcaatatct cagccggtgc cgctctggca    720

aatgcgggtg cgtacgtcta cttagacaag tctccggatc tgcacgtgat ttccttcgat    780

tggaaaccgt acgaagcgaa ctccagcttt acagtgctgg ctaaaatgaa acaggatgac    840

ttgctggtcc tgatcaacta cgtttattcg gagggaaacg gtaaatgtgt ctggcaagaa    900

gaagaacgga tttcggatga ctatattgtg cagaaaccga aaaaggatgg ccaggtgtcg    960

tacagttact cctacattgg gaatagcccg attggtgaat ggtcgacagt aacccgcgat   1020

ctcttggtag atgttgcgcg cgcgttgagc tccggagaca atcggaaaaa ggacgataat   1080

gtagtgttac acgcggggga tcttcgcctc gtgagtttag gctttcgtgg cgaactgacc   1140

gtaaaacaga aaatcaccca gcgtagggaa cagcatagcc atgccttcta cgcagcagcc   1200

gattggctag tcaaaaacca gaatgataga ggaggctgga gtgtaccggt tgagcgttcc   1260

atcgcagagc gcaagttggt tctcccgcca ggttggcatt ctgcaatggc gcaaggccat   1320

ggtatttcag tgcttacgcg tgcgtttaaa cactttaatg acgagaaata cctcaaatcc   1380

gctgcgaaag cgcttaagct gttcaaaatc aactcttcag atggtggtgt tcgcggggaa   1440

ttcttcggca atatttggta tgaagaatat ccgaccactc ctggttcttt tgtgttaaat   1500

ggctttctgt acagcctgat tggcctgtat gacctgagcc aattggagct gatgatagat   1560

gagaacgatg aaaccatgcg cgccaaaatc caggaagcgc aagaactgta ttcagctggc   1620

gtgcgttctc tgaaacaatt gctgccactg tatgatacgg gcagtggcac gatctacgat   1680

ctgcgacatg ttgcgttagg tacggcacct aacttagccc gttgggatta tcatgcggtt   1740

catgtttatc tgctgaaatg gattgccggc attgagaagg acgaagtgct cagcaaaacc   1800

gccgatcgat ggattggcta tgcgtacggg aaacgcgcaa aacacaacta a             1851
```

<210> SEQ ID NO 19
<211> LENGTH: 616
<212> TYPE: PRT
<213> ORGANISM: Caenorhabditis elegans

<400> SEQUENCE: 19

```
Met Lys Cys Leu Arg Trp Arg Ser Asn Arg His Arg Ile Tyr Leu Leu
1               5                   10                  15

Val Ala Cys Gly Ala Leu Phe Leu Leu Asn Arg His Leu Thr Gln Glu
            20                  25                  30

Glu Ser Arg Ile Asp Glu Glu Asp Glu Glu Leu Thr Gln Val Asp Val
        35                  40                  45

Asn Glu Asp Asp Lys Lys Ile Glu Cys Glu Pro Pro Gly Ser Ile Glu
    50                  55                  60

Ser Lys Cys Ile Ala Asp Asn Gly Lys Ser Met Lys Cys Trp Lys Asp
65                  70                  75                  80
```

-continued

```
Glu Glu Asp Val Tyr Phe Pro Val Ser Tyr Leu Lys Lys Arg Phe Asp
                85                  90                  95

Met Thr Gly Lys Leu Gly Lys Asp Gly Ser Thr Phe Glu Leu Tyr Thr
            100                 105                 110

Ser Tyr Ala Lys Met Arg Ser Pro Asp Ser Thr Tyr Asp Pro Leu Gly
        115                 120                 125

Pro Phe Gly His Phe Ser Thr Tyr Ser Val Glu Thr Arg Asp Arg Val
    130                 135                 140

Arg Cys Val Ser Ala Lys Thr Asp Val Pro Met Ser Thr Gln Trp Asp
145                 150                 155                 160

Pro Ile Pro Tyr Tyr Tyr Pro Ile Gln Ile Ser Gln Tyr Gly Leu Gln
                165                 170                 175

His Tyr Ser Arg Met Lys Leu Asp Ser Ile Ser Asn Lys Ser Glu Ala
            180                 185                 190

Ser Pro Lys Asp Asp Val Ile Leu Gly Val Asn Ser Lys Glu Trp Lys
        195                 200                 205

Gly Ala Ala Gly Met His Glu Thr Thr Glu Arg Leu Phe Phe Asn Asp
    210                 215                 220

Glu Gln Met Gly Lys Val Val Asn Ile Ser Ala Gly Ala Ala Leu Ala
225                 230                 235                 240

Asn Ala Gly Ala Tyr Val Tyr Leu Asp Lys Ser Pro Asp Leu His Val
                245                 250                 255

Ile Ser Phe Asp Trp Lys Pro Tyr Glu Ala Asn Ser Ser Phe Thr Val
            260                 265                 270

Leu Ala Lys Met Lys Gln Asp Asp Leu Leu Val Leu Ile Asn Tyr Val
        275                 280                 285

Tyr Ser Glu Gly Asn Gly Lys Cys Val Trp Gln Glu Glu Glu Arg Ile
    290                 295                 300

Ser Asp Asp Tyr Ile Val Gln Lys Pro Lys Lys Asp Gly Gln Val Ser
305                 310                 315                 320

Tyr Ser Tyr Ser Tyr Ile Gly Asn Ser Pro Ile Gly Glu Trp Ser Thr
                325                 330                 335

Val Thr Arg Asp Leu Leu Val Asp Val Ala Arg Ala Leu Ser Ser Gly
            340                 345                 350

Asp Asn Arg Lys Lys Asp Asp Asn Val Val Leu His Ala Gly Asp Leu
        355                 360                 365

Arg Leu Val Ser Leu Gly Phe Arg Gly Glu Leu Thr Val Lys Gln Lys
    370                 375                 380

Ile Thr Gln Arg Arg Glu Gln His Ser His Ala Phe Tyr Ala Ala Ala
385                 390                 395                 400

Asp Trp Leu Val Lys Asn Gln Asn Asp Arg Gly Gly Trp Ser Val Pro
                405                 410                 415

Val Glu Arg Ser Ile Ala Glu Arg Lys Leu Val Leu Pro Pro Gly Trp
            420                 425                 430

His Ser Ala Met Ala Gln Gly His Gly Ile Ser Val Leu Thr Arg Ala
        435                 440                 445

Phe Lys His Phe Asn Asp Glu Lys Tyr Leu Lys Ser Ala Ala Lys Ala
    450                 455                 460

Leu Lys Leu Phe Lys Ile Asn Ser Ser Asp Gly Gly Val Arg Gly Glu
465                 470                 475                 480

Phe Phe Gly Asn Ile Trp Tyr Glu Glu Tyr Pro Thr Thr Pro Gly Ser
                485                 490                 495

Phe Val Leu Asn Gly Phe Leu Tyr Ser Leu Ile Gly Leu Tyr Asp Leu
```

```
            500                 505                 510

Ser Gln Leu Glu Leu Met Ile Asp Glu Asn Asp Glu Thr Met Arg Ala
        515                 520                 525

Lys Ile Gln Glu Ala Gln Glu Leu Tyr Ser Ala Gly Val Arg Ser Leu
    530                 535                 540

Lys Gln Leu Leu Pro Leu Tyr Asp Thr Gly Ser Gly Thr Ile Tyr Asp
545                 550                 555                 560

Leu Arg His Val Ala Leu Gly Thr Ala Pro Asn Leu Ala Arg Trp Asp
                565                 570                 575

Tyr His Ala Val His Val Tyr Leu Leu Lys Trp Ile Ala Gly Ile Glu
            580                 585                 590

Lys Asp Glu Val Leu Ser Lys Thr Ala Asp Arg Trp Ile Gly Tyr Ala
        595                 600                 605

Tyr Gly Lys Arg Ala Lys His Asn
    610                 615


<210> SEQ ID NO 20
<211> LENGTH: 6646
<212> TYPE: DNA
<213> ORGANISM: Artificial Sequence
<220> FEATURE:
<223> OTHER INFORMATION: plasmid

<400> SEQUENCE: 20

ccgacaccat cgaatggtgc aaaacctttc gcggtatggc atgatagcgc ccggaagaga     60

gtcaattcag ggtggtgaat gtgaaaccag taacgttata cgatgtcgca gagtatgccg    120

gtgtctctta tcagaccgtt tcccgcgtgg tgaaccaggc cagccacgtt tctgcgaaaa    180

cgcgggaaaa agtggaagcg gcgatggcgg agctgaatta cattcccaac cgcgtggcac    240

aacaactggc gggcaaacag tcgttgctga ttggcgttgc cacctccagt ctggccctgc    300

acgcgccgtc gcaaattgtc gcggcgatta aatctcgcgc cgatcaactg ggtgccagcg    360

tggtggtgtc gatggtagaa cgaagcggcg tcgaagcctg taaagcggcg gtgcacaatc    420

ttctcgcgca acgcgtcagt gggctgatca ttaactatcc gctggatgac caggatgcca    480

ttgctgtgga agctgcctgc actaatgttc cggcgttatt tcttgatgtc tctgaccaga    540

cacccatcaa cagtattatt ttctcccatg aagacggtac gcgactgggc gtggagcatc    600

tggtcgcatt gggtcaccag caaatcgcgc tgttagcggg cccattaagt tctgtctcgg    660

cgcgtctgcg tctggctggc tggcataaat atctcactcg caatcaaatt cagccgatag    720

cggaacggga aggcgactgg agtgccatgt ccggttttca acaaaccatg caaatgctga    780

atgagggcat cgttcccact gcgatgctgg ttgccaacga tcagatggcg ctgggcgcaa    840

tgcgcgccat taccgagtcc gggctgcgcg ttggtgcgga tatctcggta gtgggatacg    900

acgataccga agacagctca tgttatatcc cgccgttaac caccatcaaa caggattttc    960

gcctgctggg gcaaaccagc gtggaccgct tgctgcaact ctctcagggc caggcggtga   1020

agggcaatca gctgttgccc gtctcactgg tgaaaagaaa aaccaccctg gcgcccaata   1080

cgcaaaccgc ctctccccgc gcgttggccg attcattaat gcagctggca cgacaggttt   1140

cccgactgga aagcgggcag tgagcgcaac gcaattaatg taagttagct cactcattag   1200

gcacaattct catgtttgac agcttatcat cgactgcacg gtgcaccaat gcttctggcg   1260

tcaggcagcc atcggaagct gtggtatggc tgtgcaggtc gtaaatcact gcataattcg   1320

tgtcgctcaa ggcgcactcc cgttctggat aatgtttttt gcgccgacat cataacggtt   1380
```

-continued

```
ctggcaaata ttctgaaatg agctgttgac aattaatcat cggctcgtat aatgtgtgga   1440
attgtgagcg gataacaatt tcacacagga aacagccagt ccgtttaggt gttttcacga   1500
gcacttcacc aacaaggacc atagcatatg aaaatcgaag aaggtaaact ggtaatctgg   1560
attaacggcg ataaaggcta taacggtctc gctgaagtcg gtaagaaatt cgagaaagat   1620
accggaatta aagtcaccgt tgagcatccg gataaactgg aagagaaatt cccacaggtt   1680
gcggcaactg gcgatggccc tgacattatc ttctgggcac acgaccgctt tggtggctac   1740
gctcaatctg gcctgttggc tgaaatcacc ccggacaaag cgttccagga caagctgtat   1800
ccgtttacct gggatgccgt acgttacaac ggcaagctga ttgcttaccc gatcgctgtt   1860
gaagcgttat cgctgattta taacaaagat ctgctgccga acccgccaaa aacctgggaa   1920
gagatcccgg cgctggataa agaactgaaa gcgaaaggta agagcgcgct gatgttcaac   1980
ctgcaagaac cgtacttcac ctggccgctg attgctgctg acggggggtta tgcgttcaag   2040
tatgaaaacg gcaagtacga cattaaagac gtgggcgtgg ataacgctgg cgcgaaagcg   2100
ggtctgacct tcctggttga cctgattaaa aacaaacaca tgaatgcaga caccgattac   2160
tccatcgcag aagctgcctt taataaaggc gaaacagcga tgaccatcaa cggcccgtgg   2220
gcatggtcca acatcgacac cagcaaagtg aattatggtg taacggtact gccgaccttc   2280
aagggtcaac catccaaacc gttcgttggc gtgctgagcg caggtattaa cgccgccagt   2340
ccgaacaaag agctggcaaa agagttcctc gaaaactatc tgctgactga tgaaggtctg   2400
gaagcggtta ataaagacaa accgctgggt gccgtagcgc tgaagtctta cgaggaagag   2460
ttggcgaaag atccacgtat tgccgccact atggaaaacg cccagaaagg tgaaatcatg   2520
ccgaacatcc cgcagatgtc cgctttctgg tatgccgtgc gtactgcggt gatcaacgcc   2580
gccagcggtc gtcagactgt cgatgaagcc ctgaaagacg cgcagactaa ttcgagctcg   2640
aacaacaaca acaataacaa taacaacaac ctcgggatcg agggaaggat ttcagaattc   2700
ggatcctcta gagtcgacct gcaggcaagc ttggcactgg ccgtcgtttt acaacgtcgt   2760
gactgggaaa accctggcgt tacccaactt aatcgccttg cagcacatcc ccctttcgcc   2820
agctggcgta atagcgaaga ggcccgcacc gatcgccctt cccaacagtt gcgcagcctg   2880
aatggcgaat ggcagcttgg ctgttttggc ggatgagata agattttcag cctgatacag   2940
attaaatcag aacgcagaag cggtctgata aaacagaatt tgcctggcgg cagtagcgcg   3000
gtggtcccac ctgaccccat gccgaactca gaagtgaaac gccgtagcgc cgatggtagt   3060
gtggggtctc cccatgcgag agtagggaac tgccaggcat caaataaaac gaaaggctca   3120
gtcgaaagac tgggcctttc gttttatctg ttgtttgtcg gtgaacgctc tcctgagtag   3180
gacaaatccg ccgggagcgg atttgaacgt tgcgaagcaa cggcccggag ggtggcgggc   3240
aggacgcccg ccataaactg ccaggcatca aattaagcag aaggccatcc tgacggatgg   3300
cctttttgcg tttctacaaa ctctttttgt ttatttttct aaatacattc aaatatgtat   3360
ccgctcatga gacaataacc ctgataaatg cttcaataat attgaaaaag gaagagtatg   3420
agtattcaac atttccgtgt cgcccttatt cccttttttg cggcattttg ccttcctgtt   3480
tttgctcacc cagaaacgct ggtgaaagta aaagatgctg aagatcagtt gggtgcacga   3540
gtgggttaca tcgaactgga tctcaacagc ggtaagatcc ttgagagttt tcgccccgaa   3600
gaacgttctc caatgatgag cacttttaaa gttctgctat gtggcgcggt attatcccgt   3660
gttgacgccg ggcaagagca actcggtcgc cgcatacact attctcagaa tgacttggtt   3720
gagtactcac cagtcacaga aaagcatctt acggatggca tgacagtaag agaattatgc   3780
```

agtgctgcca taaccatgag tgataacact gcggccaact tacttctgac aacgatcgga 3840
ggaccgaagg agctaaccgc ttttttgcac aacatggggg atcatgtaac tcgccttgat 3900
cgttgggaac cggagctgaa tgaagccata ccaaacgacg agcgtgacac cacgatgcct 3960
gtagcaatgg caacaacgtt gcgcaaacta ttaactggcg aactacttac tctagcttcc 4020
cggcaacaat taatagactg gatggaggcg gataaagttg caggaccact tctgcgctcg 4080
gcccttccgg ctggctggtt tattgctgat aaatctggag ccggtgagcg tgggtctcgc 4140
ggtatcattg cagcactggg gccagatggt aagccctccc gtatcgtagt tatctacacg 4200
acggggagtc aggcaactat ggatgaacga aatagacaga tcgctgagat aggtgcctca 4260
ctgattaagc attggtaact gtcagaccaa gtttactcat atatacttta gattgattta 4320
ccccggttga taatcagaaa agccccaaaa acaggaagat tgtataagca aatatttaaa 4380
ttgtaaacgt taatattttg ttaaaattcg cgttaaattt ttgttaaatc agctcatttt 4440
ttaaccaata ggccgaaatc ggcaaaatcc cttataaatc aaaagaatag accgagatag 4500
ggttgagtgt tgttccagtt tggaacaaga gtccactatt aaagaacgtg gactccaacg 4560
tcaaagggcg aaaaaccgtc tatcagggcg atggcccact acgtgaacca tcacccaaat 4620
caagtttttt ggggtcgagg tgccgtaaag cactaaatcg gaaccctaaa gggagccccc 4680
gatttagagc ttgacgggga aagccggcga acgtggcgag aaaggaaggg aagaaagcga 4740
aaggagcggg cgctagggcg ctggcaagtg tagcggtcac gctgcgcgta accaccacac 4800
ccgccgcgct taatgcgccg ctacagggcg cgtaaaagga tctaggtgaa gatccttttt 4860
gataatctca tgaccaaaat cccttaacgt gagttttcgt tccactgagc gtcagacccc 4920
gtagaaaaga tcaaaggatc ttcttgagat cctttttttc tgcgcgtaat ctgctgcttg 4980
caaacaaaaa aaccaccgct accagcggtg gtttgtttgc cggatcaaga gctaccaact 5040
ctttttccga aggtaactgg cttcagcaga gcgcagatac caaatactgt ccttctagtg 5100
tagccgtagt taggccacca cttcaagaac tctgtagcac cgcctacata cctcgctctg 5160
ctaatcctgt taccagtggc tgctgccagt ggcgataagt cgtgtcttac cgggttggac 5220
tcaagacgat agttaccgga taaggcgcag cggtcgggct gaacgggggg ttcgtgcaca 5280
cagcccagct tggagcgaac gacctacacc gaactgagat acctacagcg tgagctatga 5340
gaaagcgcca cgcttcccga agggagaaag gcggacaggt atccggtaag cggcagggtc 5400
ggaacaggag agcgcacgag ggagcttcca gggggaaacg cctggtatct ttatagtcct 5460
gtcgggtttc gccacctctg acttgagcgt cgatttttgt gatgctcgtc aggggggcgg 5520
agcctatgga aaaacgccag caacgcggcc tttttacggt tcctggcctt ttgctggcct 5580
tttgctcaca tgttctttcc tgcgttatcc cctgattctg tggataaccg tattaccgcc 5640
tttgagtgag ctgataccgc tcgccgcagc cgaacgaccg agcgcagcga gtcagtgagc 5700
gaggaagcgg aagagcgcct gatgcggtat tttctcctta cgcatctgtg cggtatttca 5760
caccgcatat atggtgcact ctcagtacaa tctgctctga tgccgcatag ttaagccagt 5820
atacactccg ctatcgctac gtgactgggt catggctgcg ccccgacacc cgccaacacc 5880
cgctgacgcg ccctgacggg cttgtctgct cccggcatcc gcttacagac aagctgtgac 5940
cgtctccggg agctgcatgt gtcagaggtt ttcaccgtca tcaccgaaac gcgcgaggca 6000
gctgcggtaa agctcatcag cgtggtcgtg cagcgattca cagatgtctg cctgttcatc 6060
cgcgtccagc tcgttgagtt tctccagaag cgttaatgtc tggcttctga taaagcgggc 6120

-continued catgttaagg gcggtttttt cctgtttggt cactgatgcc tccgtgtaag ggggatttct 6180
gttcatgggg gtaatgatac cgatgaaacg agagaggatg ctcacgatac gggttactga 6240
tgatgaacat gcccggttac tggaacgttg tgagggtaaa caactggcgg tatggatgcg 6300
gcgggaccag agaaaaatca ctcagggtca atgccagcgc ttcgttaata cagatgtagg 6360
tgttccacag ggtagccagc agcatcctgc gatgcagatc cggaacataa tggtgcaggg 6420
cgctgacttc cgcgtttcca gactttacga aacacggaaa ccgaagacca ttcatgttgt 6480
tgctcaggtc gcagacgttt tgcagcagca gtcgcttcac gttcgctcgc gtatcggtga 6540
ttcattctgc taaccagtaa ggcaaccccg ccagcctagc cgggtcctca acgacaggag 6600
cacgatcatg cgcacccgtg gccaggaccc aacgctgccc gaaatt 6646

<210> SEQ ID NO 21
<211> LENGTH: 6556
<212> TYPE: DNA
<213> ORGANISM: Artificial Sequence
<220> FEATURE:
<223> OTHER INFORMATION: plasmid

<400> SEQUENCE: 21
ccgacaccat cgaatggtgc aaaacctttc gcggtatggc atgatagcgc ccggaagaga 60
gtcaattcag ggtggtgaat gtgaaaccag taacgttata cgatgtcgca gagtatgccg 120
gtgtctctta tcagaccgtt tcccgcgtgg tgaaccaggc cagccacgtt tctgcgaaaa 180
cgcgggaaaa agtggaagcg gcgatggcgg agctgaatta cattcccaac cgcgtggcac 240
aacaactggc gggcaaacag tcgttgctga ttggcgttgc cacctccagt ctggccctgc 300
acgcgccgtc gcaaattgtc gcggcgatta aatctcgcgc cgatcaactg ggtgccagcg 360
tggtggtgtc gatggtagaa cgaagcggcg tcgaagcctg taaagcggcg gtgcacaatc 420
ttctcgcgca acgcgtcagt gggctgatca ttaactatcc gctggatgac caggatgcca 480
ttgctgtgga agctgcctgc actaatgttc cggcgttatt tcttgatgtc tctgaccaga 540
cacccatcaa cagtattatt ttctcccatg aagacggtac gcgactgggc gtggagcatc 600
tggtcgcatt gggtcaccag caaatcgcgc tgttagcggg cccattaagt tctgtctcgg 660
cgcgtctgcg tctggctggc tggcataaat atctcactcg caatcaaatt cagccgatag 720
cggaacggga aggcgactgg agtgccatgt ccggttttca acaaaccatg caaatgctga 780
atgagggcat cgttcccact gcgatgctgg ttgccaacga tcagatggcg ctgggcgcaa 840
tgcgcgccat taccgagtcc gggctgcgcg ttggtgcgga tatctcggta gtgggatacg 900
acgataccga agacagctca tgttatatcc cgccgttaac caccatcaaa caggattttc 960
gcctgctggg gcaaaccagc gtggaccgct tgctgcaact ctctcagggc caggcggtga 1020
agggcaatca gctgttgccc gtctcactgg tgaaaagaaa aaccaccctg gcgcccaata 1080
cgcaaaccgc ctctccccgc gcgttggccg attcattaat gcagctggca cgacaggttt 1140
cccgactgga aagcgggcag tgagcgcaac gcaattaatg taagttagct cactcattag 1200
gcacaattct catgtttgac agcttatcat cgactgcacg gtgcaccaat gcttctggcg 1260
tcaggcagcc atcggaagct gtggtatggc tgtgcaggtc gtaaatcact gcataattcg 1320
tgtcgctcaa ggcgcactcc cgttctggat aatgtttttt gcgccgacat cataacggtt 1380
ctggcaaata ttctgaaatg agctgttgac aattaatcat cggctcgtat aatgtgtgga 1440
attgtgagcg gataacaatt tcacacagga aacagccagt ccgtttaggt gttttcacga 1500
gcacttcacc aacaaggacc atagcatatg aaaatcgaag aaggtaaact ggtaatctgg 1560

-continued

```
attaacggcg ataaaggcta taacggtctc gctgaagtcg gtaagaaatt cgagaaagat   1620
accggaatta aagtcaccgt tgagcatccg gataaactgg aagagaaatt cccacaggtt   1680
gcggcaactg gcgatggccc tgacattatc ttctgggcac acgaccgctt tggtggctac   1740
gctcaatctg gcctgttggc tgaaatcacc ccggacaaag cgttccagga caagctgtat   1800
ccgtttacct gggatgccgt acgttacaac ggcaagctga ttgcttaccc gatcgctgtt   1860
gaagcgttat cgctgattta taacaaagat ctgctgccga acccgccaaa aacctgggaa   1920
gagatcccgg cgctggataa agaactgaaa gcgaaaggta agagcgcgct gatgttcaac   1980
ctgcaagaac cgtacttcac ctggccgctg attgctgctg acggggggtta tgcgttcaag   2040
tatgaaaacg gcaagtacga cattaaagac gtgggcgtgg ataacgctgg cgcgaaagcg   2100
ggtctgacct tcctggttga cctgattaaa aacaaacaca tgaatgcaga caccgattac   2160
tccatcgcag aagctgcctt taataaaggc gaaacagcga tgaccatcaa cggcccgtgg   2220
gcatggtcca acatcgacac cagcaaagtg aattatggtg taacggtact gccgaccttc   2280
aagggtcaac catccaaacc gttcgttggc gtgctgagcg caggtattaa cgccgccagt   2340
ccgaacaaag agctggcaaa agagttcctc gaaaactatc tgctgactga tgaaggtctg   2400
gaagcggtta ataaagacaa accgctgggt gccgtagcgc tgaagtctta cgaggaagag   2460
ttggcgaaag atccacgtat tgccgccact atggaaaacg cccagaaagg tgaaatcatg   2520
ccgaacatcc cgcagatgtc cgctttctgg tatgccgtgc gtactgcggt gatcaacgcc   2580
gccagcggtc gtcagactgt cgatgcagcc ctggcggccg cctcgagctc ggatccaagc   2640
ttggcactgg ccgtcgtttt acaacgtcgt gactgggaaa accctggcgt tacccaactt   2700
aatcgccttg cagcacatcc ccctttcgcc agctggcgta atagcgaaga ggcccgcacc   2760
gatcgccctt cccaacagtt gcgcagcctg aatggcgaat ggcagcttgg ctgttttggc   2820
ggatgagata agattttcag cctgatacag attaaatcag aacgcagaag cggtctgata   2880
aaacagaatt tgcctggcgg cagtagcgcg gtggtcccac ctgaccccat gccgaactca   2940
gaagtgaaac gccgtagcgc cgatggtagt gtggggtctc cccatgcgag agtagggaac   3000
tgccaggcat caaataaaac gaaaggctca gtcgaaagac tgggcctttc gttttatctg   3060
ttgtttgtcg gtgaacgctc tcctgagtag gacaaatccg ccgggagcgg atttgaacgt   3120
tgcgaagcaa cggcccggag ggtggcgggc aggacgcccg ccataaactg ccaggcatca   3180
aattaagcag aaggccatcc tgacggatgg cctttttgcg tttctacaaa ctctttttgt   3240
ttatttttct aaatacattc aaatatgtat ccgctcatga gacaataacc ctgataaatg   3300
cttcaataat attgaaaaag gaagagtatg agtattcaac atttccgtgt cgcccttatt   3360
ccctttttttg cggcattttg ccttcctgtt tttgctcacc cagaaacgct ggtgaaagta   3420
aaagatgctg aagatcagtt gggtgcacga gtgggttaca tcgaactgga tctcaacagc   3480
ggtaagatcc ttgagagttt tcgccccgaa gaacgttctc caatgatgag cacttttaaa   3540
gttctgctat gtggcgcggt attatcccgt gttgacgccg ggcaagagca actcggtcgc   3600
cgcatacact attctcagaa tgacttggtt gagtactcac cagtcacaga aaagcatctt   3660
acggatggca tgacagtaag agaattatgc agtgctgcca taaccatgag tgataacact   3720
gcggccaact tacttctgac aacgatcgga ggaccgaagg agctaaccgc ttttttgcac   3780
aacatggggg atcatgtaac tcgccttgat cgttgggaac cggagctgaa tgaagccata   3840
ccaaacgacg agcgtgacac cacgatgcct gtagcaatgg caacaacgtt gcgcaaacta   3900
```

-continued

```
ttaactggcg aactacttac tctagcttcc cggcaacaat taatagactg gatggaggcg   3960
gataaagttg caggaccact tctgcgctcg gcccttccgg ctggctggtt tattgctgat   4020
aaatctggag ccggtgagcg tgggtctcgc ggtatcattg cagcactggg gccagatggt   4080
aagccctccc gtatcgtagt tatctacacg acggggagtc aggcaactat ggatgaacga   4140
aatagacaga tcgctgagat aggtgcctca ctgattaagc attggtaact gtcagaccaa   4200
gtttactcat atatacttta gattgattta ccccggttga taatcagaaa agccccaaaa   4260
acaggaagat tgtataagca aatatttaaa ttgtaaacgt taatattttg ttaaaattcg   4320
cgttaaattt ttgttaaatc agctcatttt ttaaccaata ggccgaaatc ggcaaaatcc   4380
cttataaatc aaaagaatag accgagatag ggttgagtgt tgttccagtt tggaacaaga   4440
gtccactatt aaagaacgtg gactccaacg tcaaagggcg aaaaaccgtc tatcagggcg   4500
atggcccact acgtgaacca tcacccaaat caagtttttt ggggtcgagg tgccgtaaag   4560
cactaaatcg gaaccctaaa gggagccccc gatttagagc ttgacgggga aagccggcga   4620
acgtggcgag aaaggaaggg aagaaagcga aaggagcggg cgctagggcg ctggcaagtg   4680
tagcggtcac gctgcgcgta accaccacac ccgccgcgct taatgcgccg ctacagggcg   4740
cgtaaaagga tctaggtgaa gatccttttt gataatctca tgaccaaaat cccttaacgt   4800
gagttttcgt tccactgagc gtcagacccc gtagaaaaga tcaaaggatc ttcttgagat   4860
cctttttttc tgcgcgtaat ctgctgcttg caaacaaaaa aaccaccgct accagcggtg   4920
gtttgtttgc cggatcaaga gctaccaact ctttttccga aggtaactgg cttcagcaga   4980
gcgcagatac caaatactgt ccttctagtg tagccgtagt taggccacca cttcaagaac   5040
tctgtagcac cgcctacata cctcgctctg ctaatcctgt taccagtggc tgctgccagt   5100
ggcgataagt cgtgtcttac cgggttggac tcaagacgat agttaccgga taaggcgcag   5160
cggtcgggct gaacgggggg ttcgtgcaca cagcccagct tggagcgaac gacctacacc   5220
gaactgagat acctacagcg tgagctatga gaaagcgcca cgcttcccga agggagaaag   5280
gcggacaggt atccggtaag cggcagggtc ggaacaggag agcgcacgag ggagcttcca   5340
gggggaaacg cctggtatct ttatagtcct gtcgggtttc gccacctctg acttgagcgt   5400
cgatttttgt gatgctcgtc aggggggcgg agcctatgga aaaacgccag caacgcggcc   5460
tttttacggt tcctggcctt ttgctggcct tttgctcaca tgttctttcc tgcgttatcc   5520
cctgattctg tggataaccg tattaccgcc tttgagtgag ctgataccgc tcgccgcagc   5580
cgaacgaccg agcgcagcga gtcagtgagc gaggaagcgg aagagcgcct gatgcggtat   5640
tttctcctta cgcatctgtg cggtatttca caccgcatat atggtgcact ctcagtacaa   5700
tctgctctga tgccgcatag ttaagccagt atacactccg ctatcgctac gtgactgggt   5760
catggctgcg ccccgacacc cgccaacacc cgctgacgcg ccctgacggg cttgtctgct   5820
cccggcatcc gcttacagac aagctgtgac cgtctccggg agctgcatgt gtcagaggtt   5880
ttcaccgtca tcaccgaaac gcgcgaggca gctgcggtaa agctcatcag cgtggtcgtg   5940
cagcgattca cagatgtctg cctgttcatc cgcgtccagc tcgttgagtt tctccagaag   6000
cgttaatgtc tggcttctga taaagcgggc catgttaagg gcggtttttt cctgtttggt   6060
cactgatgcc tccgtgtaag ggggatttct gttcatgggg gtaatgatac cgatgaaacg   6120
agagaggatg ctcacgatac gggttactga tgatgaacat gcccggttac tggaacgttg   6180
tgagggtaaa caactggcgg tatggatgcg gcgggaccag agaaaaatca ctcagggtca   6240
atgccagcgc ttcgttaata cagatgtagg tgttccacag ggtagccagc agcatcctgc   6300
```

gatgcagatc cggaacataa tggtgcaggg cgctgacttc cgcgtttcca gactttacga 6360
aacacggaaa ccgaagacca ttcatgttgt tgctcaggtc gcagacgttt tgcagcagca 6420
gtcgcttcac gttcgctcgc gtatcggtga ttcattctgc taaccagtaa ggcaaccccg 6480
ccagcctagc cgggtcctca acgacaggag cacgatcatg cgcacccgtg gccaggaccc 6540
aacgctgccc gaaatt 6556

<210> SEQ ID NO 22
<211> LENGTH: 36
<212> TYPE: DNA
<213> ORGANISM: Artificial Sequence
<220> FEATURE:
<223> OTHER INFORMATION: primer

<400> SEQUENCE: 22
agctgagtcg acccccagga aaaattggtt aataac 36

<210> SEQ ID NO 23
<211> LENGTH: 33
<212> TYPE: DNA
<213> ORGANISM: Artificial Sequence
<220> FEATURE:
<223> OTHER INFORMATION: primer

<400> SEQUENCE: 23
agctgagcat gcttccaact gcgctaatga cgc 33

<210> SEQ ID NO 24
<211> LENGTH: 313
<212> TYPE: DNA
<213> ORGANISM: Artificial Sequence
<220> FEATURE:
<223> OTHER INFORMATION: fragment

<400> SEQUENCE: 24
gcatgcttcc aactgcgcta atgacgcagc tggacgaagg cgggattctc gtcttacccg 60
taggggagga gcaccagtat ttgaaacggg tgcgtcgtcg gggaggcgaa tttattatcg 120
ataccgtgga ggccgtgcgc tttgtccctt tagtgaaggg tgagctggct taaaacgtga 180
ggaaatacct ggatttttcc tggttatttt gccgcaggtc agcgtatcgt gaacatcttt 240
tccagtgttc agtagggtgc cttgcacggt aattatgtca ctggttatta accaattttt 300
cctgggggtc gac 313

<210> SEQ ID NO 25
<211> LENGTH: 33
<212> TYPE: DNA
<213> ORGANISM: Artificial Sequence
<220> FEATURE:
<223> OTHER INFORMATION: primer

<400> SEQUENCE: 25
agctgatcta gaaaacagaa tttgcctggc ggc 33

<210> SEQ ID NO 26
<211> LENGTH: 33
<212> TYPE: DNA
<213> ORGANISM: Artificial Sequence
<220> FEATURE:
<223> OTHER INFORMATION: primer

<400> SEQUENCE: 26
agctgaggat ccaggaagag tttgtagaaa cgc 33

<210> SEQ ID NO 27
<211> LENGTH: 369
<212> TYPE: DNA
<213> ORGANISM: Artificial Sequence
<220> FEATURE:
<223> OTHER INFORMATION: fragment

<400> SEQUENCE: 27
tctagaaaca gaatttgcct ggcggcagta gcgcggtggt cccacctgac cccatgccga 60
actcagaagt gaaacgccgt agcgccgatg gtagtgtggg gtctccccat gcgagagtag 120
ggaactgcca ggcatcaaat aaaacgaaag gctcagtcga aagactgggc ctttcgtttt 180
atctgttgtt tgtcggtgaa cgctctcctg agtaggacaa atccgccggg agcggatttg 240
aacgttgcga agcaacggcc cggagggtgg cgggcaggac gcccgccata aactgccagg 300
catcaaatta agcagaaggc catcctgacg gatggccttt ttgcgtttct acaaactctt 360
cctggatcc 369

<210> SEQ ID NO 28
<211> LENGTH: 35
<212> TYPE: DNA
<213> ORGANISM: Artificial Sequence
<220> FEATURE:
<223> OTHER INFORMATION: primer

<400> SEQUENCE: 28
ttcctggggg tcgacatgac tacgaaaatt tttaa 35

<210> SEQ ID NO 29
<211> LENGTH: 35
<212> TYPE: DNA
<213> ORGANISM: Artificial Sequence
<220> FEATURE:
<223> OTHER INFORMATION: primer

<400> SEQUENCE: 29
attctgtttt ctagactaag gaaccaacac aagct 35

<210> SEQ ID NO 30
<211> LENGTH: 30
<212> TYPE: DNA
<213> ORGANISM: Artificial Sequence
<220> FEATURE:
<223> OTHER INFORMATION: primer

<400> SEQUENCE: 30
gtcgaccccc aggaaaaatt ggttaataac 30

<210> SEQ ID NO 31
<211> LENGTH: 30
<212> TYPE: DNA
<213> ORGANISM: Artificial Sequence
<220> FEATURE:
<223> OTHER INFORMATION: primer

<400> SEQUENCE: 31
tctagaaaac agaatttgcc tggcggcagt 30

<210> SEQ ID NO 32
<211> LENGTH: 1980
<212> TYPE: DNA
<213> ORGANISM: Flavobacterium heparinum

<400> SEQUENCE: 32

```
atgactacga aaatttttaa aaggatcatt gtatttgctg taattgccct atcgtcggga     60
aatatacttg cacaaagctc ttccattacc aggaaagatt ttgaccacat caaccttgag    120
tattccggac tggaaaaggt taataaagca gttgctgccg gcaactatga cgatgcggcc    180
aaagcattac tggcatacta cagggaaaaa agtaaggcca gggaacctga tttcagtaat    240
gcagaaaagc ctgccgatat acgccagccc atagataagg ttacgcgtga aatggccgac    300
aaggctttgg tccaccagtt tcaaccgcac aaaggctacg gctattttga ttatggtaaa    360
gacatcaact ggcagatgtg gccggtaaaa gacaatgaag tacgctggca gttgcaccgt    420
gtaaaatggt ggcaggctat ggccctggtt tatcacgcta cgggcgatga aaaatatgca    480
agagaatggg tatatcagta cagcgattgg gccagaaaaa acccattggg cctgtcgcag    540
gataatgata aatttgtgtg gcggcccctt gaagtgtcgg acagggtaca aagtcttccc    600
ccaaccttca gcttatttgt aaactcgcca gcctttaccc cagccttttt aatggaattt    660
ttaaacagtt accaccaaca ggccgattat ttatctacgc attatgccga acagggaaac    720
caccgtttat ttgaagccca acgcaacttg tttgcagggg tatctttccc tgaatttaaa    780
gattcaccaa gatggaggca aaccggcata tcggtgctga acaccgagat caaaaaacag    840
gtttatgccg atgggatgca gtttgaactt tcaccaattt accatgtagc tgccatcgat    900
atcttcttaa aggcctatgg ttctgcaaaa cgagttaacc ttgaaaaaga atttccgcaa    960
tcttatgtac aaactgtaga aaatatgatt atggcgctga tcagtatttc actgccagat   1020
tataacaccc ctatgtttgg agattcatgg attacagata aaaatttcag gatggcacag   1080
tttgccagct gggcccgggt tttcccggca aaccaggcca taaaatattt tgctacagat   1140
ggcaaacaag gtaaggcgcc taacttttta tccaaagcat tgagcaatgc aggcttttat   1200
acgtttagaa gcggatggga taaaaatgca accgttatgg tattaaaagc cagtcctccc   1260
ggagaatttc atgcccagcc ggataacggg acttttgaac tttttataaa gggcagaaac   1320
tttaccccag acgccggggt atttgtgtat agcggcgacg aagccatcat gaaactgcgg   1380
aactggtacc gtcaaacccg catacacagc acgcttacac tcgacaatca aaatatggtc   1440
attaccaaag cccggcaaaa caaatgggaa acaggaaata accttgatgt gcttacctat   1500
accaacccaa gctatccgaa tctggaccat cagcgcagtg tacttttcat caacaaaaaa   1560
tactttctgg tcatcgatag ggcaataggc gaagctaccg gaaacctggg cgtacactgg   1620
cagcttaaag aagacagcaa ccctgttttc gataagacaa agaaccgggt ttacaccact   1680
tacagagatg gtaacaacct gatgatccaa tcgttgaatg cggacaggac cagcctcaat   1740
gaagaagaag gaaaggtatc ttatgtttac aataaggagc tgaaaagacc tgctttcgta   1800
tttgaaaagc ctaaaaagaa tgccggcaca caaaattttg tcagtatagt ttatccatac   1860
gacggccaga aggctccaga gatcagcata cgggaaaaca agggcaatga ttttgagaaa   1920
ggcaagctta atctaaccct taccattaac ggaaaacaac agcttgtgtt ggttccttag   1980
```

<210> SEQ ID NO 33
<211> LENGTH: 659
<212> TYPE: PRT
<213> ORGANISM: Flavobacterium heparinum

<400> SEQUENCE: 33

```
Met Thr Thr Lys Ile Phe Lys Arg Ile Ile Val Phe Ala Val Ile Ala
1               5                   10                  15
```

```
Leu Ser Ser Gly Asn Ile Leu Ala Gln Ser Ser Ser Ile Thr Arg Lys
            20                  25                  30

Asp Phe Asp His Ile Asn Leu Glu Tyr Ser Gly Leu Glu Lys Val Asn
        35                  40                  45

Lys Ala Val Ala Ala Gly Asn Tyr Asp Asp Ala Ala Lys Ala Leu Leu
    50                  55                  60

Ala Tyr Tyr Arg Glu Lys Ser Lys Ala Arg Glu Pro Asp Phe Ser Asn
65                  70                  75                  80

Ala Glu Lys Pro Ala Asp Ile Arg Gln Pro Ile Asp Lys Val Thr Arg
                85                  90                  95

Glu Met Ala Asp Lys Ala Leu Val His Gln Phe Gln Pro His Lys Gly
            100                 105                 110

Tyr Gly Tyr Phe Asp Tyr Gly Lys Asp Ile Asn Trp Gln Met Trp Pro
        115                 120                 125

Val Lys Asp Asn Glu Val Arg Trp Gln Leu His Arg Val Lys Trp Trp
    130                 135                 140

Gln Ala Met Ala Leu Val Tyr His Ala Thr Gly Asp Glu Lys Tyr Ala
145                 150                 155                 160

Arg Glu Trp Val Tyr Gln Tyr Ser Asp Trp Ala Arg Lys Asn Pro Leu
                165                 170                 175

Gly Leu Ser Gln Asp Asn Asp Lys Phe Val Trp Arg Pro Leu Glu Val
            180                 185                 190

Ser Asp Arg Val Gln Ser Leu Pro Pro Thr Phe Ser Leu Phe Val Asn
        195                 200                 205

Ser Pro Ala Phe Thr Pro Ala Phe Leu Met Glu Phe Leu Asn Ser Tyr
    210                 215                 220

His Gln Gln Ala Asp Tyr Leu Ser Thr His Tyr Ala Glu Gln Gly Asn
225                 230                 235                 240

His Arg Leu Phe Glu Ala Gln Arg Asn Leu Phe Ala Gly Val Ser Phe
                245                 250                 255

Pro Glu Phe Lys Asp Ser Pro Arg Trp Arg Gln Thr Gly Ile Ser Val
            260                 265                 270

Leu Asn Thr Glu Ile Lys Lys Gln Val Tyr Ala Asp Gly Met Gln Phe
        275                 280                 285

Glu Leu Ser Pro Ile Tyr His Val Ala Ala Ile Asp Ile Phe Leu Lys
    290                 295                 300

Ala Tyr Gly Ser Ala Lys Arg Val Asn Leu Glu Lys Glu Phe Pro Gln
305                 310                 315                 320

Ser Tyr Val Gln Thr Val Glu Asn Met Ile Met Ala Leu Ile Ser Ile
                325                 330                 335

Ser Leu Pro Asp Tyr Asn Thr Pro Met Phe Gly Asp Ser Trp Ile Thr
            340                 345                 350

Asp Lys Asn Phe Arg Met Ala Gln Phe Ala Ser Trp Ala Arg Val Phe
        355                 360                 365

Pro Ala Asn Gln Ala Ile Lys Tyr Phe Ala Thr Asp Gly Lys Gln Gly
    370                 375                 380

Lys Ala Pro Asn Phe Leu Ser Lys Ala Leu Ser Asn Ala Gly Phe Tyr
385                 390                 395                 400

Thr Phe Arg Ser Gly Trp Asp Lys Asn Ala Thr Val Met Val Leu Lys
                405                 410                 415

Ala Ser Pro Pro Gly Glu Phe His Ala Gln Pro Asp Asn Gly Thr Phe
            420                 425                 430
```

-continued

```
Glu Leu Phe Ile Lys Gly Arg Asn Phe Thr Pro Asp Ala Gly Val Phe
        435                 440                 445

Val Tyr Ser Gly Asp Glu Ala Ile Met Lys Leu Arg Asn Trp Tyr Arg
    450                 455                 460

Gln Thr Arg Ile His Ser Thr Leu Thr Leu Asp Asn Gln Asn Met Val
465                 470                 475                 480

Ile Thr Lys Ala Arg Gln Asn Lys Trp Glu Thr Gly Asn Asn Leu Asp
                485                 490                 495

Val Leu Thr Tyr Thr Asn Pro Ser Tyr Pro Asn Leu Asp His Gln Arg
            500                 505                 510

Ser Val Leu Phe Ile Asn Lys Lys Tyr Phe Leu Val Ile Asp Arg Ala
        515                 520                 525

Ile Gly Glu Ala Thr Gly Asn Leu Gly Val His Trp Gln Leu Lys Glu
    530                 535                 540

Asp Ser Asn Pro Val Phe Asp Lys Thr Lys Asn Arg Val Tyr Thr Thr
545                 550                 555                 560

Tyr Arg Asp Gly Asn Asn Leu Met Ile Gln Ser Leu Asn Ala Asp Arg
                565                 570                 575

Thr Ser Leu Asn Glu Glu Glu Gly Lys Val Ser Tyr Val Tyr Asn Lys
            580                 585                 590

Glu Leu Lys Arg Pro Ala Phe Val Phe Glu Lys Pro Lys Lys Asn Ala
        595                 600                 605

Gly Thr Gln Asn Phe Val Ser Ile Val Tyr Pro Tyr Asp Gly Gln Lys
    610                 615                 620

Ala Pro Glu Ile Ser Ile Arg Glu Asn Lys Gly Asn Asp Phe Glu Lys
625                 630                 635                 640

Gly Lys Leu Asn Leu Thr Leu Thr Ile Asn Gly Lys Gln Gln Leu Val
                645                 650                 655

Leu Val Pro


<210> SEQ ID NO 34
<211> LENGTH: 35
<212> TYPE: DNA
<213> ORGANISM: Artificial Sequence
<220> FEATURE:
<223> OTHER INFORMATION: primer

<400> SEQUENCE: 34

aagcttggca ctggccgtcg ttttacaacg tcgtg                              35


<210> SEQ ID NO 35
<211> LENGTH: 35
<212> TYPE: DNA
<213> ORGANISM: Artificial Sequence
<220> FEATURE:
<223> OTHER INFORMATION: primer

<400> SEQUENCE: 35

ggatccgaat tctgaaatcc ttccctcgat cccga                              35


<210> SEQ ID NO 36
<211> LENGTH: 48
<212> TYPE: DNA
<213> ORGANISM: Artificial Sequence
<220> FEATURE:
<223> OTHER INFORMATION: primer

<400> SEQUENCE: 36

atagcggccg cgtcttctgg aggcctgaaa tatgaagaaa ttgactgc                48
```

<210> SEQ ID NO 37
<211> LENGTH: 31
<212> TYPE: DNA
<213> ORGANISM: Artificial Sequence
<220> FEATURE:
<223> OTHER INFORMATION: primer

<400> SEQUENCE: 37
atactcgagt taattgtgtt ttgcacggct a 31

<210> SEQ ID NO 38
<211> LENGTH: 18
<212> TYPE: DNA
<213> ORGANISM: Artificial Sequence
<220> FEATURE:
<223> OTHER INFORMATION: primer

<400> SEQUENCE: 38
tccagaagac gcggccgc 18

<210> SEQ ID NO 39
<211> LENGTH: 22
<212> TYPE: DNA
<213> ORGANISM: Artificial Sequence
<220> FEATURE:
<223> OTHER INFORMATION: primer

<400> SEQUENCE: 39
ctcgagctcg gatccaagct tg 22

<210> SEQ ID NO 40
<211> LENGTH: 37
<212> TYPE: DNA
<213> ORGANISM: Artificial Sequence
<220> FEATURE:
<223> OTHER INFORMATION: primer

<400> SEQUENCE: 40
gccgcgtctt ctggaggcct gaaatacgag gaaatcg 37

<210> SEQ ID NO 41
<211> LENGTH: 37
<212> TYPE: DNA
<213> ORGANISM: Artificial Sequence
<220> FEATURE:
<223> OTHER INFORMATION: primer

<400> SEQUENCE: 41
ggatccgagc tcgagttagt tgtgtttcgc gcgagag 37

<210> SEQ ID NO 42
<211> LENGTH: 41
<212> TYPE: DNA
<213> ORGANISM: Artificial Sequence
<220> FEATURE:
<223> OTHER INFORMATION: primer

<400> SEQUENCE: 42
gccgcgtctt ctggaggatt gaaatacgaa gaaattgact g 41

<210> SEQ ID NO 43
<211> LENGTH: 39
<212> TYPE: DNA
<213> ORGANISM: Artificial Sequence
<220> FEATURE:

<223> OTHER INFORMATION: primer

<400> SEQUENCE: 43
ggatccgagc tcgagttagt tatgtttcgc acgaccacc 39

<210> SEQ ID NO 44
<211> LENGTH: 41
<212> TYPE: DNA
<213> ORGANISM: Artificial Sequence
<220> FEATURE:
<223> OTHER INFORMATION: primer

<400> SEQUENCE: 44
gccgcgtctt ctggaggtca gaaatacgaa gaaattgatt g 41

<210> SEQ ID NO 45
<211> LENGTH: 37
<212> TYPE: DNA
<213> ORGANISM: Artificial Sequence
<220> FEATURE:
<223> OTHER INFORMATION: primer

<400> SEQUENCE: 45
ggatccgagc tcgagttagt tatgctttgc tcgcccg 37

<210> SEQ ID NO 46
<211> LENGTH: 36
<212> TYPE: DNA
<213> ORGANISM: Artificial Sequence
<220> FEATURE:
<223> OTHER INFORMATION: primer

<400> SEQUENCE: 46
gccgcgtctt ctggaggcgt tcggtatgaa gaaatc 36

<210> SEQ ID NO 47
<211> LENGTH: 37
<212> TYPE: DNA
<213> ORGANISM: Artificial Sequence
<220> FEATURE:
<223> OTHER INFORMATION: primer

<400> SEQUENCE: 47
ggatccgagc tcgagttaat tatgctttgc gcgaccg 37

<210> SEQ ID NO 48
<211> LENGTH: 37
<212> TYPE: DNA
<213> ORGANISM: Artificial Sequence
<220> FEATURE:
<223> OTHER INFORMATION: primer

<400> SEQUENCE: 48
gccgcgtctt ctggaaaacc gtctgttagt gccattg 37

<210> SEQ ID NO 49
<211> LENGTH: 39
<212> TYPE: DNA
<213> ORGANISM: Artificial Sequence
<220> FEATURE:
<223> OTHER INFORMATION: primer

<400> SEQUENCE: 49
ggatccgagc tcgagttaat tatgtttcgc gactttgcc 39

<210> SEQ ID NO 50
<211> LENGTH: 33
<212> TYPE: DNA
<213> ORGANISM: Artificial Sequence
<220> FEATURE:
<223> OTHER INFORMATION: primer

<400> SEQUENCE: 50
gccgcgtctt ctggatatat gcgctgtgca gcg 33

<210> SEQ ID NO 51
<211> LENGTH: 37
<212> TYPE: DNA
<213> ORGANISM: Artificial Sequence
<220> FEATURE:
<223> OTHER INFORMATION: primer

<400> SEQUENCE: 51
ggatccgagc tcgagttaat tatgcttggc acgaccg 37

<210> SEQ ID NO 52
<211> LENGTH: 34
<212> TYPE: DNA
<213> ORGANISM: Artificial Sequence
<220> FEATURE:
<223> OTHER INFORMATION: primer

<400> SEQUENCE: 52
gccgcgtctt ctggaatgaa atgcttgcgt tggc 34

<210> SEQ ID NO 53
<211> LENGTH: 38
<212> TYPE: DNA
<213> ORGANISM: Artificial Sequence
<220> FEATURE:
<223> OTHER INFORMATION: primer

<400> SEQUENCE: 53
ggatccgagc tcgagttagt tgtgttttgc gcgtttcc 38

<210> SEQ ID NO 54
<211> LENGTH: 585
<212> TYPE: PRT
<213> ORGANISM: Danio rerio

<400> SEQUENCE: 54

```
Met Arg Cys Leu Ala Ala Arg Val Asn Tyr Lys Thr Leu Ile Val Ile
1               5                   10                  15

Cys Ala Leu Phe Thr Leu Val Thr Val Leu Leu Trp Asn Arg Cys Ser
            20                  25                  30

Ser Asp Lys Ala Ile Gln Phe Pro Arg Arg Leu Ser Ser Gly Ala Pro
        35                  40                  45

Ser Pro Gln Gln Ser Glu Glu Ala Gln Pro Pro Glu Pro Pro Lys Ala
    50                  55                  60

Pro Pro Val Val Gly Gly Leu Lys Tyr Glu Glu Ile Asp Cys Leu Ile
65                  70                  75                  80

Asn Asp Glu His Thr Ile Lys Gly Arg Arg Glu Gly Asn Glu Val Phe
                85                  90                  95

Leu Pro Phe Ser Trp Val Glu Lys Tyr Phe Glu Val Tyr Gly Lys Val
            100                 105                 110

Ala Gln Tyr Asp Gly Tyr Asp Arg Phe Glu Phe Ser His Ser Tyr Ser
        115                 120                 125
```

-continued

```
Lys Val Tyr Ala Gln Arg Ala Pro Tyr His Pro Asp Gly Val Phe Met
    130                 135                 140

Ser Phe Glu Gly Tyr Asn Val Glu Val Arg Asp Arg Val Lys Cys Ile
145                 150                 155                 160

Ser Gly Val Glu Gly Val Pro Leu Ser Thr Gln Trp Gly Pro Gln Gly
                165                 170                 175

Tyr Phe Tyr Pro Ile Gln Ile Ala Gln Tyr Gly Leu Ser His Tyr Ser
            180                 185                 190

Lys Asn Leu Thr Glu Lys Pro Pro His Val Glu Val Tyr Glu Thr Ala
        195                 200                 205

Glu Asp Lys Asp Ser Arg Ser Ala Asp Trp Thr Val Pro Lys Gly Cys
    210                 215                 220

Ser Leu Ser Thr Val Ala Asp Lys Ser Arg Phe Thr Asn Val Lys Gln
225                 230                 235                 240

Phe Val Ala Pro Glu Asn Ser Glu Gly Val Ser Leu Gln Leu Gly Asn
                245                 250                 255

Thr Lys Asp Phe Ile Ile Ser Phe Asp Leu Lys Phe Leu Thr Asn Gly
            260                 265                 270

Ser Val Ser Val Val Leu Glu Thr Thr Glu Lys Asn Gln Leu Phe Thr
        275                 280                 285

Val His Tyr Val Ser Asn Thr Gln Leu Ile Ala Phe Lys Asp Arg Asp
    290                 295                 300

Ile Tyr Tyr Gly Ile Gly Pro Arg Thr Ser Trp Ser Thr Val Thr Arg
305                 310                 315                 320

Asp Leu Val Thr Asp Leu Arg Lys Gly Val Gly Leu Ser Asn Thr Lys
                325                 330                 335

Ala Val Lys Gln Thr Lys Ile Met Pro Lys Arg Val Val Arg Leu Val
            340                 345                 350

Ala Lys Gly Arg Gly Phe Leu Asp Asn Ile Thr Ile Ser Thr Thr Ala
        355                 360                 365

His Met Ala Ala Phe Phe Ala Ala Ser Asp Trp Leu Val Arg Asn Gln
    370                 375                 380

Asp Glu Arg Gly Gly Trp Pro Ile Met Val Thr Arg Lys Leu Gly Glu
385                 390                 395                 400

Gly Phe Lys Ser Leu Glu Pro Gly Trp Tyr Ser Ala Met Ala Gln Gly
                405                 410                 415

Gln Ala Ile Ser Thr Leu Val Arg Ala Tyr Leu Leu Thr Lys Asp His
            420                 425                 430

Ala Phe Leu Ser Ser Ala Leu Arg Ala Thr Ala Pro Tyr Lys Leu Pro
        435                 440                 445

Ser Glu Gln His Gly Val Lys Ala Val Phe Met Asn Lys His Asp Trp
    450                 455                 460

Tyr Glu Glu Tyr Pro Thr Thr Pro Ser Ser Phe Val Leu Asn Gly Phe
465                 470                 475                 480

Met Tyr Ser Leu Ile Gly Leu Tyr Asp Leu Lys Glu Thr Ala Gly Glu
                485                 490                 495

Lys Leu Gly Lys Glu Ala Arg Leu Leu Tyr Glu Arg Gly Met Glu Ser
            500                 505                 510

Leu Lys Ala Met Leu Pro Leu Tyr Asp Thr Gly Ser Gly Thr Ile Tyr
        515                 520                 525

Asp Leu Arg His Phe Met Leu Gly Thr Ala Pro Asn Leu Ala Arg Trp
    530                 535                 540

Asp Tyr His Thr Thr His Ile Asn Gln Leu Gln Leu Leu Ser Thr Ile
```

-continued

```
545                 550                 555                 560

Asp Glu Ser Pro Ile Phe Lys Glu Phe Val Lys Arg Trp Lys Ser Tyr
                565                 570                 575

Leu Lys Gly Gly Arg Ala Lys His Asn
            580                 585


<210> SEQ ID NO 55
<211> LENGTH: 1548
<212> TYPE: DNA
<213> ORGANISM: Danio rerio

<400> SEQUENCE: 55

ggcctgaaat acgaggaaat tgactgcctg atcaacgatg agcataccat caaagggcgc      60

cgtgagggga atgaagtgtt tctgccgttc agttgggttg agaaatactt tgaagtttat     120

gggaaagtcg cacagtacga tggttatgat cgttttgaat tttcccatag ctattcaaaa     180

gtgtatgcgc agcgggcgcc gtatcatccc gatggtgtgt ttatgagctt tgaaggttac     240

aatgtggaag tacgtgatcg cgtaaaatgc attagcggtg tagaaggtgt cccgttgagc     300

acccagtggg gtccccaagg ctacttttac ccgattcaga ttgctcagta tgggctttct     360

cactatagta agaatctgac cgaaaagccg ccacacgtgg aagtctatga aacggccgaa     420

gataaagatt cccgctcggc cgattggacc gtaccgaagg gctgctcgtt atcgacggtg     480

gctgacaaaa gccgctttac caatgtgaaa cagtttgtgg cgcctgagaa cagtgaagga     540

gtttccctgc aacttggcaa cactaaagac ttcattatta gcttcgatct caaatttctg     600

acaaatggct ctgtgtccgt tgtgctggaa accactgaaa agaatcagtt attcaccgtg     660

cactatgtta gcaacactca gctgattgcc tttaaagatc gtgatattta ctacggtatt     720

gggccacgga catcatggtc taccgtcacc cgggatcttg tgacggacct ccgtaaaggc     780

gttggcttga gcaacacaaa agcagtcaag cagacgaaaa tcatgccgaa gcgcgttgta     840

cgtctggtag cgaaaggccg tggattcctc gacaatatca ccatctccac cactgctcat     900

atggctgcgt tctttgctgc gtccgattgg ttggtgcgca accaagacga gcgcggaggt     960

tggccgatta tggttacgcg caaactgggt gaaggcttta aaagtcttga acctgggtgg    1020

tattcagcca tggcacaggg ccaggccatt tctacccttg ttcgcgcgta tctgttgacc    1080

aaagatcatg ccttcttaag ttcagcctta cgtgctaccg cgccgtataa actgcctagc    1140

gaacaacatg gcgtgaaagc agtctttatg aacaagcacg attggtacga ggagtacccg    1200

acaactccgt cctcgtttgt gttgaatggc ttcatgtatt cgctgattgg cctgtacgac    1260

ctcaaagaga ctgcgggtga gaaattaggc aaagaagcac gcttactgta cgaacgcggc    1320

atggaaagct taaaagccat gttgccgctg tatgacacgg gttctggtac gatttacgat    1380

ctgcgccatt tcatgctggg cacagcaccc aatctggccc gttgggacta tcacacgacg    1440

cacatcaacc agctgcaact cctgagtacc atcgacgaaa gcccaatctt caaagagttc    1500

gttaaacgct ggaaaagtta tctgaaaggc ggacgcgcca aacataac                1548


<210> SEQ ID NO 56
<211> LENGTH: 516
<212> TYPE: PRT
<213> ORGANISM: Danio rerio

<400> SEQUENCE: 56

Gly Leu Lys Tyr Glu Glu Ile Asp Cys Leu Ile Asn Asp Glu His Thr
1               5                   10                  15
```

-continued

```
Ile Lys Gly Arg Arg Glu Gly Asn Glu Val Phe Leu Pro Phe Ser Trp
            20                  25                  30

Val Glu Lys Tyr Phe Glu Val Tyr Gly Lys Val Ala Gln Tyr Asp Gly
        35                  40                  45

Tyr Asp Arg Phe Glu Phe Ser His Ser Tyr Ser Lys Val Tyr Ala Gln
    50                  55                  60

Arg Ala Pro Tyr His Pro Asp Gly Val Phe Met Ser Phe Glu Gly Tyr
65                  70                  75                  80

Asn Val Glu Val Arg Asp Arg Val Lys Cys Ile Ser Gly Val Glu Gly
                85                  90                  95

Val Pro Leu Ser Thr Gln Trp Gly Pro Gln Gly Tyr Phe Tyr Pro Ile
            100                 105                 110

Gln Ile Ala Gln Tyr Gly Leu Ser His Tyr Ser Lys Asn Leu Thr Glu
        115                 120                 125

Lys Pro Pro His Val Glu Val Tyr Glu Thr Ala Glu Asp Lys Asp Ser
    130                 135                 140

Arg Ser Ala Asp Trp Thr Val Pro Lys Gly Cys Ser Leu Ser Thr Val
145                 150                 155                 160

Ala Asp Lys Ser Arg Phe Thr Asn Val Lys Gln Phe Val Ala Pro Glu
                165                 170                 175

Asn Ser Glu Gly Val Ser Leu Gln Leu Gly Asn Thr Lys Asp Phe Ile
            180                 185                 190

Ile Ser Phe Asp Leu Lys Phe Leu Thr Asn Gly Ser Val Ser Val Val
        195                 200                 205

Leu Glu Thr Thr Glu Lys Asn Gln Leu Phe Thr Val His Tyr Val Ser
    210                 215                 220

Asn Thr Gln Leu Ile Ala Phe Lys Asp Arg Asp Ile Tyr Tyr Gly Ile
225                 230                 235                 240

Gly Pro Arg Thr Ser Trp Ser Thr Val Thr Arg Asp Leu Val Thr Asp
                245                 250                 255

Leu Arg Lys Gly Val Gly Leu Ser Asn Thr Lys Ala Val Lys Gln Thr
            260                 265                 270

Lys Ile Met Pro Lys Arg Val Val Arg Leu Val Ala Lys Gly Arg Gly
        275                 280                 285

Phe Leu Asp Asn Ile Thr Ile Ser Thr Thr Ala His Met Ala Ala Phe
    290                 295                 300

Phe Ala Ala Ser Asp Trp Leu Val Arg Asn Gln Asp Glu Arg Gly Gly
305                 310                 315                 320

Trp Pro Ile Met Val Thr Arg Lys Leu Gly Glu Gly Phe Lys Ser Leu
                325                 330                 335

Glu Pro Gly Trp Tyr Ser Ala Met Ala Gln Gly Gln Ala Ile Ser Thr
            340                 345                 350

Leu Val Arg Ala Tyr Leu Leu Thr Lys Asp His Ala Phe Leu Ser Ser
        355                 360                 365

Ala Leu Arg Ala Thr Ala Pro Tyr Lys Leu Pro Ser Glu Gln His Gly
    370                 375                 380

Val Lys Ala Val Phe Met Asn Lys His Asp Trp Tyr Glu Glu Tyr Pro
385                 390                 395                 400

Thr Thr Pro Ser Ser Phe Val Leu Asn Gly Phe Met Tyr Ser Leu Ile
                405                 410                 415

Gly Leu Tyr Asp Leu Lys Glu Thr Ala Gly Glu Lys Leu Gly Lys Glu
            420                 425                 430

Ala Arg Leu Leu Tyr Glu Arg Gly Met Glu Ser Leu Lys Ala Met Leu
```

-continued

```
        435                 440                 445

Pro Leu Tyr Asp Thr Gly Ser Gly Thr Ile Tyr Asp Leu Arg His Phe
    450                 455                 460

Met Leu Gly Thr Ala Pro Asn Leu Ala Arg Trp Asp Tyr His Thr Thr
465                 470                 475                 480

His Ile Asn Gln Leu Gln Leu Leu Ser Thr Ile Asp Glu Ser Pro Ile
                485                 490                 495

Phe Lys Glu Phe Val Lys Arg Trp Lys Ser Tyr Leu Lys Gly Gly Arg
            500                 505                 510

Ala Lys His Asn
        515


<210> SEQ ID NO 57
<211> LENGTH: 585
<212> TYPE: PRT
<213> ORGANISM: Danio rerio

<400> SEQUENCE: 57

Met Arg Cys Leu Ala Ala Arg Val Asn Tyr Lys Thr Leu Ile Val Ile
1               5                   10                  15

Cys Ala Leu Phe Thr Leu Val Thr Val Leu Leu Trp Asn Arg Cys Ser
            20                  25                  30

Ser Asp Lys Ala Leu Arg Phe Pro Arg Gln His Pro Gln Pro Pro Pro
        35                  40                  45

Ser Pro Lys Ile Asp Ser His Pro Gln Pro Pro Gln Pro Pro Glu Pro
    50                  55                  60

Pro Pro Val Val Gly Gly Leu Lys Tyr Glu Glu Ile Asp Cys Leu Ile
65                  70                  75                  80

Asn Asp Glu His Thr Ile Lys Gly Arg Arg Glu Gly Asn Glu Val Phe
                85                  90                  95

Leu Pro Phe Ser Trp Val Glu Lys Tyr Phe Glu Val Tyr Gly Lys Val
            100                 105                 110

Ala Gln Tyr Asp Gly Tyr Asp Arg Phe Glu Phe Ser His Ser Tyr Ser
        115                 120                 125

Lys Val Tyr Ala Gln Arg Ala Pro Tyr His Pro Asp Gly Val Phe Met
    130                 135                 140

Ser Phe Glu Gly Tyr Asn Val Glu Val Arg Asp Arg Val Lys Cys Ile
145                 150                 155                 160

Ser Gly Val Glu Gly Val Pro Leu Ser Thr Gln Trp Gly Pro Gln Gly
                165                 170                 175

Tyr Phe Tyr Pro Ile Gln Ile Ala Gln Tyr Gly Leu Ser His Tyr Ser
            180                 185                 190

Lys Asn Leu Thr Glu Lys Pro Pro His Val Glu Val Tyr Glu Thr Ala
        195                 200                 205

Glu Asp Lys Asp Ser Arg Ser Ser Asp Trp Thr Val Pro Lys Gly Cys
    210                 215                 220

Ser Leu Ser Thr Val Tyr Asp Lys Ser Arg Phe Thr Asn Val Lys Gln
225                 230                 235                 240

Phe Val Ala Pro Glu Asn Ser Glu Gly Val Ser Leu Gln Leu Gly Asn
                245                 250                 255

Thr Lys Asp Phe Ile Ile Ser Phe Asp Leu Lys Phe Leu Thr Asn Gly
            260                 265                 270

Ser Val Ser Val Val Leu Glu Thr Thr Glu Lys Asn Gln Leu Phe Thr
        275                 280                 285
```

-continued

```
Val His Tyr Val Ser Asn Thr Gln Leu Ile Ala Phe Lys Asp Arg Asp
    290                 295                 300

Ile Tyr Tyr Gly Ile Gly Pro Arg Thr Ser Trp Ser Thr Val Thr Arg
305                 310                 315                 320

Asp Leu Val Thr Asp Leu Arg Lys Gly Val Gly Leu Ser Asn Thr Lys
                325                 330                 335

Ala Val Lys Gln Thr Lys Ile Met Pro Lys Arg Val Val Arg Leu Val
            340                 345                 350

Ala Lys Gly Arg Gly Phe Leu Asp Asn Ile Thr Ile Ser Thr Thr Ala
        355                 360                 365

His Met Ala Ala Phe Phe Ala Ala Ser Asp Trp Leu Val Arg Asn Gln
    370                 375                 380

Asp Glu Arg Gly Gly Trp Pro Ile Met Val Thr Arg Lys Leu Gly Glu
385                 390                 395                 400

Gly Phe Lys Ser Leu Glu Pro Gly Trp Tyr Ser Ala Met Ala Gln Gly
                405                 410                 415

Gln Ala Ile Ser Thr Leu Val Arg Ala Tyr Leu Leu Thr Lys Asp His
            420                 425                 430

Ala Phe Leu Ser Ser Ala Leu Arg Ala Thr Ala Pro Tyr Lys Leu Pro
        435                 440                 445

Ser Glu Gln His Gly Val Lys Ala Val Phe Met Asn Lys His Asp Trp
    450                 455                 460

Tyr Glu Glu Tyr Pro Thr Thr Pro Ser Ser Phe Val Leu Asn Gly Phe
465                 470                 475                 480

Met Tyr Ser Leu Ile Gly Leu Tyr Asp Leu Lys Glu Thr Ala Gly Glu
                485                 490                 495

Lys Leu Gly Lys Glu Ala Arg Gln Leu Tyr Glu Arg Gly Met Glu Ser
            500                 505                 510

Leu Lys Ala Met Leu Pro Leu Tyr Asp Thr Gly Ser Gly Thr Ile Tyr
        515                 520                 525

Asp Leu Arg His Phe Met Leu Gly Thr Ala Pro Asn Leu Ala Arg Trp
    530                 535                 540

Asp Tyr His Thr Thr His Ile Asn Gln Leu Gln Leu Leu Ser Thr Ile
545                 550                 555                 560

Asp Glu Ser Pro Ile Phe Lys Glu Phe Val Lys Arg Trp Lys Ser Tyr
                565                 570                 575

Leu Lys Gly Gly Arg Ala Lys His Asn
            580                 585
```

<210> SEQ ID NO 58
<211> LENGTH: 1548
<212> TYPE: DNA
<213> ORGANISM: Danio rerio

<400> SEQUENCE: 58

```
ggtctgaaat atgaagagat tgactgctta attaacgatg aacacaccat caaaggtcgc      60

cgtgaaggca atgaagtgtt cctgccgttt tcatgggtgg agaaatactt tgaagtgtat     120

ggcaaagttg cgcagtatga tggctatgat cgctttgaat tctcacacag ttacagcaaa     180

gtgtacgctc agcgggcacc ctatcatccc gatggcgtct ttatgtcttt tgaagggtac     240

aatgtggaag tacgcgatcg tgtcaagtgc attagcggtg tcgaaggtgt gcctctgtcg     300

acgcaatggg gcccacaggg ctacttttac ccgattcaga tcgcccaata tggcctgtcg     360

cattatagca agaatctgac cgagaagcca ccccatgtag aggtgtatga aactgcggag     420
```

gacaaggata gccgcagctc agattggacc gtgccgaaag gctgttctct cagtaccgtc 480
tacgacaaaa gccgcttcac gaatgtgaaa cagtttgtag cccctgaaaa ctctgaaggc 540
gtttcccttc agctggggaa cacaaaagat ttcatcatct cctttgacct gaaatttctt 600
accaacgggt ccgtgagtgt agttctggag actaccgaaa agaaccagct gttcacagtg 660
cattatgtga gcaacacgca gttgattgcg tttaaagatc gcgatattta ctatggtatt 720
ggcccgcgta cgtcatggag tacggtcact cgtgacctcg ttacggatct tcgtaaaggg 780
gttgggctgt cgaacaccaa agcggttaaa cagaccaaaa ttatgccgaa acgcgtcgtt 840
cgcctcgttg cgaaaggacg tggatttctg gataacatca caatctcgac tacagcccat 900
atggctgcgt tctttgcggc atcggactgg ctggtgcgca atcaggatga acgtggtggc 960
tggccaatta tggtcacgcg taagctggga gaaggtttca aaagcttaga gccggggtgg 1020
tacagtgcta tggcccaagg tcaggccatt tccaccctgg ttcgcgccta cttgcttacc 1080
aaggatcatg cgtttctgag ttcggcgtta cgcgcaacgg caccgtataa gctgccgtct 1140
gagcaacatg gtgtaaaagc agtattcatg aacaaacatg attggtatga agaatatccg 1200
accacccctt caagctttgt gttgaatggc ttcatgtatt ccctgatcgg cctgtacgac 1260
ttaaaagaga ctgctggtga gaaactgggc aaggaagccc gtcaattgta cgaacgcggt 1320
atggaatccc tgaaagccat gctcccgttg tacgatacgg gatctggtac catctatgac 1380
ttacgtcact ttatgctggg caccgcaccg aatctggctc gctgggacta tcacacaact 1440
cacatcaacc aattacagct cttgagcacc attgacgaaa gcccaatttt caaagaattc 1500
gtcaaacggt ggaaatctta tctgaaaggc ggtcgcgcaa agcataat 1548

<210> SEQ ID NO 59
<211> LENGTH: 516
<212> TYPE: PRT
<213> ORGANISM: Danio rerio

<400> SEQUENCE: 59

Gly Leu Lys Tyr Glu Glu Ile Asp Cys Leu Ile Asn Asp Glu His Thr
1 5 10 15

Ile Lys Gly Arg Arg Glu Gly Asn Glu Val Phe Leu Pro Phe Ser Trp
20 25 30

Val Glu Lys Tyr Phe Glu Val Tyr Gly Lys Val Ala Gln Tyr Asp Gly
35 40 45

Tyr Asp Arg Phe Glu Phe Ser His Ser Tyr Ser Lys Val Tyr Ala Gln
50 55 60

Arg Ala Pro Tyr His Pro Asp Gly Val Phe Met Ser Phe Glu Gly Tyr
65 70 75 80

Asn Val Glu Val Arg Asp Arg Val Lys Cys Ile Ser Gly Val Glu Gly
85 90 95

Val Pro Leu Ser Thr Gln Trp Gly Pro Gln Gly Tyr Phe Tyr Pro Ile
100 105 110

Gln Ile Ala Gln Tyr Gly Leu Ser His Tyr Ser Lys Asn Leu Thr Glu
115 120 125

Lys Pro Pro His Val Glu Val Tyr Glu Thr Ala Glu Asp Lys Asp Ser
130 135 140

Arg Ser Ser Asp Trp Thr Val Pro Lys Gly Cys Ser Leu Ser Thr Val
145 150 155 160

Tyr Asp Lys Ser Arg Phe Thr Asn Val Lys Gln Phe Val Ala Pro Glu
165 170 175

```
Asn Ser Glu Gly Val Ser Leu Gln Leu Gly Asn Thr Lys Asp Phe Ile
            180                 185                 190

Ile Ser Phe Asp Leu Lys Phe Leu Thr Asn Gly Ser Val Ser Val Val
        195                 200                 205

Leu Glu Thr Thr Glu Lys Asn Gln Leu Phe Thr Val His Tyr Val Ser
    210                 215                 220

Asn Thr Gln Leu Ile Ala Phe Lys Asp Arg Asp Ile Tyr Tyr Gly Ile
225                 230                 235                 240

Gly Pro Arg Thr Ser Trp Ser Thr Val Thr Arg Asp Leu Val Thr Asp
                245                 250                 255

Leu Arg Lys Gly Val Gly Leu Ser Asn Thr Lys Ala Val Lys Gln Thr
            260                 265                 270

Lys Ile Met Pro Lys Arg Val Val Arg Leu Val Ala Lys Gly Arg Gly
        275                 280                 285

Phe Leu Asp Asn Ile Thr Ile Ser Thr Thr Ala His Met Ala Ala Phe
    290                 295                 300

Phe Ala Ala Ser Asp Trp Leu Val Arg Asn Gln Asp Glu Arg Gly Gly
305                 310                 315                 320

Trp Pro Ile Met Val Thr Arg Lys Leu Gly Glu Gly Phe Lys Ser Leu
                325                 330                 335

Glu Pro Gly Trp Tyr Ser Ala Met Ala Gln Gly Gln Ala Ile Ser Thr
            340                 345                 350

Leu Val Arg Ala Tyr Leu Leu Thr Lys Asp His Ala Phe Leu Ser Ser
        355                 360                 365

Ala Leu Arg Ala Thr Ala Pro Tyr Lys Leu Pro Ser Glu Gln His Gly
    370                 375                 380

Val Lys Ala Val Phe Met Asn Lys His Asp Trp Tyr Glu Glu Tyr Pro
385                 390                 395                 400

Thr Thr Pro Ser Ser Phe Val Leu Asn Gly Phe Met Tyr Ser Leu Ile
                405                 410                 415

Gly Leu Tyr Asp Leu Lys Glu Thr Ala Gly Glu Lys Leu Gly Lys Glu
            420                 425                 430

Ala Arg Gln Leu Tyr Glu Arg Gly Met Glu Ser Leu Lys Ala Met Leu
        435                 440                 445

Pro Leu Tyr Asp Thr Gly Ser Gly Thr Ile Tyr Asp Leu Arg His Phe
    450                 455                 460

Met Leu Gly Thr Ala Pro Asn Leu Ala Arg Trp Asp Tyr His Thr Thr
465                 470                 475                 480

His Ile Asn Gln Leu Gln Leu Leu Ser Thr Ile Asp Glu Ser Pro Ile
                485                 490                 495

Phe Lys Glu Phe Val Lys Arg Trp Lys Ser Tyr Leu Lys Gly Gly Arg
            500                 505                 510

Ala Lys His Asn
        515
```

<210> SEQ ID NO 60
<211> LENGTH: 585
<212> TYPE: PRT
<213> ORGANISM: Danio rerio

<400> SEQUENCE: 60

```
Met Arg Cys Leu Ala Ala Arg Val Asn Tyr Lys Thr Leu Ile Val Ile
1               5                   10                  15

Cys Ala Leu Phe Thr Leu Leu Thr Val Leu Leu Trp Asn Lys Cys Ser
            20                  25                  30
```

-continued

```
Ser Asp Lys Ala Leu Arg Phe Leu Pro Gln His Pro Gln Pro Pro Pro
        35                  40                  45

Ser Pro Lys Ile Asp Ser His Pro Gln Gln Pro Gln Pro Pro Glu Pro
    50                  55                  60

Pro Pro Val Val Gly Gly Val Lys Tyr Glu Glu Ile Asp Cys Leu Ile
65                  70                  75                  80

Asn Asp Glu Ala Thr Ile Lys Gly Arg Arg Glu Gly Ser Glu Val Phe
                85                  90                  95

Leu Pro Phe Ser Trp Val Glu Lys Tyr Phe Glu Val Tyr Gly Lys Val
            100                 105                 110

Val Gln Tyr Asp Gly Tyr Asp Arg Phe Glu Phe Ser His Ser Tyr Ser
        115                 120                 125

Lys Val Tyr Ala Gln Arg Ala Pro Tyr His Pro Asp Gly Val Phe Met
    130                 135                 140

Ser Phe Glu Gly Tyr Asn Val Glu Val Arg Asp Arg Val Lys Cys Ile
145                 150                 155                 160

Ser Gly Val Glu Gly Val Pro Leu Ser Thr Gln Trp Gly Pro Gln Gly
                165                 170                 175

Tyr Phe Tyr Pro Ile Gln Ile Ala Gln Tyr Gly Leu Ser His Tyr Ser
            180                 185                 190

Lys Asn Leu Thr Glu Lys Pro Pro His Val Glu Val Tyr Glu Thr Ala
        195                 200                 205

Glu Glu Arg Asp Ser Arg Ser Ser Ala Trp Thr Val Pro Lys Gly Cys
    210                 215                 220

Ser Leu Thr Arg Val Tyr Asp Lys Thr Arg Ala Thr Ser Val Lys Gln
225                 230                 235                 240

Phe Ser Ala Pro Glu Asn Ser Glu Gly Val Ser Leu Gln Leu Gly Asn
                245                 250                 255

Thr Lys Asp Phe Ile Ile Ser Phe Asp Leu Lys Phe Thr Thr Asn Gly
            260                 265                 270

Ser Val Ser Val Val Leu Glu Thr Thr Glu Lys Asn Gln Leu Phe Thr
        275                 280                 285

Ile His Tyr Val Ser Asn Thr Gln Leu Ile Ala Phe Lys Asp Arg Asp
    290                 295                 300

Ile Thr Tyr Gly Ile Gly Pro Arg Thr Ser Trp Ser Thr Val Thr Arg
305                 310                 315                 320

Asp Leu Val Thr Asp Leu Arg Lys Gly Val Gly Leu Ser Asn Thr Lys
                325                 330                 335

Ala Val Lys Ala Thr Lys Ile Met Pro Lys Arg Val Val Arg Leu Val
            340                 345                 350

Val Lys Gly Thr Gly Phe Ile Asp Asn Ile Thr Ile Ser Thr Thr Ala
        355                 360                 365

His Met Ala Ala Phe Phe Ala Ala Ser Asp Trp Leu Val Arg Asn Gln
    370                 375                 380

Asp Glu Arg Gly Gly Trp Pro Ile Met Val Thr Arg Lys Leu Gly Glu
385                 390                 395                 400

Gly Phe Lys Ser Leu Glu Pro Gly Trp Tyr Ser Ala Met Ala Gln Gly
                405                 410                 415

Gln Ala Met Ser Thr Leu Val Arg Ala Tyr Leu Leu Thr Lys Asp Asp
            420                 425                 430

Arg Phe Leu Lys Ala Ala Leu Arg Ala Thr Ala Pro Tyr Lys Leu Pro
        435                 440                 445
```

-continued

```
Ser Glu Gln His Gly Val Lys Ala Val Phe Met Asn Lys His Asp Trp
    450                 455                 460

Tyr Glu Glu Tyr Pro Thr Ile Pro Ser Ser Phe Val Leu Asn Gly Phe
465                 470                 475                 480

Met Tyr Ser Leu Ile Gly Leu Tyr Asp Leu Lys Glu Thr Ala Gly Glu
                485                 490                 495

Lys Leu Gly Arg Glu Ala Gly Gln Leu Tyr Ser Arg Gly Met Glu Ser
            500                 505                 510

Leu Lys Ala Met Leu Pro Leu Tyr Asp Thr Gly Ser Gly Thr Ile Tyr
        515                 520                 525

Asp Leu Arg His Phe Met Leu Gly Thr Ala Pro Asn Leu Ala Arg Trp
    530                 535                 540

Asp Tyr His Thr Thr His Ile Asn Gln Leu Gln Leu Leu Ser Thr Ile
545                 550                 555                 560

Asp Asn Ser Pro Ile Phe Lys Glu Phe Val Lys Arg Trp Lys Ser Tyr
                565                 570                 575

Leu Lys Gly Gly Arg Ala Lys His Asn
            580                 585


<210> SEQ ID NO 61
<211> LENGTH: 1548
<212> TYPE: DNA
<213> ORGANISM: Danio rerio

<400> SEQUENCE: 61

ggcgtcaagt acgaagaaat cgattgcctg attaacgatg aagccaccat caaaggtcgt     60

cgcgaaggct cggaagtgtt tctgccattc agttgggtag agaaatattt tgaagtgtat    120

gggaaagtcg tacagtacga tggctacgat cggtttgagt ttagccacag ctatagcaag    180

gtctatgcgc aacgtgcccc atatcatcca gatggggtgt ttatgtcatt cgaaggctac    240

aatgtggagg tgcgtgatcg tgttaagtgc attagcggcg ttgagggtgt gccgttgtcc    300

acccaatggg gcccacaagg ttacttttac ccgattcaaa tcgcccagta tggcctgtcc    360

cattattcga agaatctgac agagaaaccg ccgcatgttg aggtctacga aactgctgaa    420

gaacgcgatt cacgcagttc tgcttggact gtgccgaaag gttgtagtct gacgcgcgtg    480

tacgataaaa cgcgcgcaac ttctgtcaaa cagtttagcg cacccgaaaa tagcgaaggc    540

gtttcgctgc aactggggaa taccaaggac ttcatcatta gttttgacct caaatttacc    600

accaatggta gtgtgtctgt tgttttggaa accaccgaga agaaccagct ctttaccatt    660

cactatgtct ccaacacaca gttgattgcc ttcaaagatc gggatattac ctatggcatt    720

ggtccgcgca ctagctggag tactgtgacc cgtgacctgg tgactgatct gcggaaaggc    780

gtcggccttt cgaacaccaa agcggtaaaa gcaacgaaaa tcatgccgaa acgtgtggtt    840

cgcctggttg taaaaggtac gggctttatc gacaacatta ccattagcac gacggcgcat    900

atggccgcat tctttgcggc ttccgattgg ctggtacgta accaggatga gcgtggagga    960

tggccgatca tggtgacccg caaattgggc gaaggtttca aatctctgga acctggttgg   1020

tattctgcga tggcgcaggg tcaggctatg tctacgctgg ttcgcgccta tctgctgacc   1080

aaagatgacc gcttcttaaa agccgcttta cgcgcaaccg caccttataa actgccttcg   1140

gagcaacatg gggtgaaagc ggtatttatg aacaaacacg attggtatga ggaatatccg   1200

acaattccga gctcattcgt tctgaacggc ttcatgtact ccctgattgg gctgtatgac   1260

cttaaagaaa cagccggtga aaagttaggc cgtgaagcgg gtcagcttta ctcccgcgga   1320
```

-continued

```
atggaatcgt taaaagcgat gctgcccctg tacgatacgg gtagcgggac catctacgac   1380

ctccgccatt ttatgctggg aaccgcgccg aatttagcgc gttgggacta tcacacgaca   1440

catattaacc agctccagtt gcttagcacg atcgacaatt cacccatctt caaggaattc   1500

gtcaaacgct ggaaatcata cttaaaaggc ggtcgcgcaa agcataat                1548


<210> SEQ ID NO 62
<211> LENGTH: 516
<212> TYPE: PRT
<213> ORGANISM: Danio rerio

<400> SEQUENCE: 62

Gly Val Lys Tyr Glu Glu Ile Asp Cys Leu Ile Asn Asp Glu Ala Thr
1               5                   10                  15

Ile Lys Gly Arg Arg Glu Gly Ser Glu Val Phe Leu Pro Phe Ser Trp
            20                  25                  30

Val Glu Lys Tyr Phe Glu Val Tyr Gly Lys Val Val Gln Tyr Asp Gly
        35                  40                  45

Tyr Asp Arg Phe Glu Phe Ser His Ser Tyr Ser Lys Val Tyr Ala Gln
    50                  55                  60

Arg Ala Pro Tyr His Pro Asp Gly Val Phe Met Ser Phe Glu Gly Tyr
65                  70                  75                  80

Asn Val Glu Val Arg Asp Arg Val Lys Cys Ile Ser Gly Val Glu Gly
                85                  90                  95

Val Pro Leu Ser Thr Gln Trp Gly Pro Gln Gly Tyr Phe Tyr Pro Ile
            100                 105                 110

Gln Ile Ala Gln Tyr Gly Leu Ser His Tyr Ser Lys Asn Leu Thr Glu
        115                 120                 125

Lys Pro Pro His Val Glu Val Tyr Glu Thr Ala Glu Glu Arg Asp Ser
    130                 135                 140

Arg Ser Ser Ala Trp Thr Val Pro Lys Gly Cys Ser Leu Thr Arg Val
145                 150                 155                 160

Tyr Asp Lys Thr Arg Ala Thr Ser Val Lys Gln Phe Ser Ala Pro Glu
                165                 170                 175

Asn Ser Glu Gly Val Ser Leu Gln Leu Gly Asn Thr Lys Asp Phe Ile
            180                 185                 190

Ile Ser Phe Asp Leu Lys Phe Thr Thr Asn Gly Ser Val Ser Val Val
        195                 200                 205

Leu Glu Thr Thr Glu Lys Asn Gln Leu Phe Thr Ile His Tyr Val Ser
    210                 215                 220

Asn Thr Gln Leu Ile Ala Phe Lys Asp Arg Asp Ile Thr Tyr Gly Ile
225                 230                 235                 240

Gly Pro Arg Thr Ser Trp Ser Thr Val Thr Arg Asp Leu Val Thr Asp
                245                 250                 255

Leu Arg Lys Gly Val Gly Leu Ser Asn Thr Lys Ala Val Lys Ala Thr
            260                 265                 270

Lys Ile Met Pro Lys Arg Val Val Arg Leu Val Val Lys Gly Thr Gly
        275                 280                 285

Phe Ile Asp Asn Ile Thr Ile Ser Thr Thr Ala His Met Ala Ala Phe
    290                 295                 300

Phe Ala Ala Ser Asp Trp Leu Val Arg Asn Gln Asp Glu Arg Gly Gly
305                 310                 315                 320

Trp Pro Ile Met Val Thr Arg Lys Leu Gly Glu Gly Phe Lys Ser Leu
                325                 330                 335
```

Glu Pro Gly Trp Tyr Ser Ala Met Ala Gln Gly Gln Ala Met Ser Thr
            340                 345                 350

Leu Val Arg Ala Tyr Leu Leu Thr Lys Asp Asp Arg Phe Leu Lys Ala
        355                 360                 365

Ala Leu Arg Ala Thr Ala Pro Tyr Lys Leu Pro Ser Glu Gln His Gly
    370                 375                 380

Val Lys Ala Val Phe Met Asn Lys His Asp Trp Tyr Glu Glu Tyr Pro
385                 390                 395                 400

Thr Ile Pro Ser Ser Phe Val Leu Asn Gly Phe Met Tyr Ser Leu Ile
                405                 410                 415

Gly Leu Tyr Asp Leu Lys Glu Thr Ala Gly Glu Lys Leu Gly Arg Glu
            420                 425                 430

Ala Gly Gln Leu Tyr Ser Arg Gly Met Glu Ser Leu Lys Ala Met Leu
        435                 440                 445

Pro Leu Tyr Asp Thr Gly Ser Gly Thr Ile Tyr Asp Leu Arg His Phe
    450                 455                 460

Met Leu Gly Thr Ala Pro Asn Leu Ala Arg Trp Asp Tyr His Thr Thr
465                 470                 475                 480

His Ile Asn Gln Leu Gln Leu Leu Ser Thr Ile Asp Asn Ser Pro Ile
                485                 490                 495

Phe Lys Glu Phe Val Lys Arg Trp Lys Ser Tyr Leu Lys Gly Gly Arg
            500                 505                 510

Ala Lys His Asn
        515

<210> SEQ ID NO 63
<211> LENGTH: 585
<212> TYPE: PRT
<213> ORGANISM: Danio rerio

<400> SEQUENCE: 63

Met Arg Cys Leu Ala Ala Arg Val Asn Tyr Lys Thr Leu Ile Val Ile
1               5                   10                  15

Cys Ala Leu Phe Thr Leu Leu Thr Val Leu Leu Trp Asn Lys Cys Ser
            20                  25                  30

Ser Glu Lys Ala Leu Arg Phe Leu Pro Gln His Pro Gln Pro Pro Pro
        35                  40                  45

Ser Pro Lys Ile Asp Ser His Pro Gln Gln Pro Gln Pro Pro Glu Pro
    50                  55                  60

Pro Pro Val Val Gly Gly Val Arg Tyr Glu Glu Ile Asp Cys Leu Ile
65                  70                  75                  80

Asn Asp Glu Ala Thr Ile Lys Gly Arg Arg Glu Gly Ser Glu Val Tyr
                85                  90                  95

Leu Pro Phe Ser Trp Met Glu Lys Tyr Phe Glu Val Tyr Gly Lys Val
            100                 105                 110

Val Gln Tyr Asp Gly Tyr Asp Arg Phe Glu Phe Ser His Ser Tyr Ser
        115                 120                 125

Lys Val Tyr Ala Gln Arg Glu Pro Tyr His Pro Asp Gly Val Phe Met
    130                 135                 140

Ser Phe Glu Gly Tyr Asn Val Glu Val Arg Asp Arg Val Lys Cys Ile
145                 150                 155                 160

Ser Gly Val Glu Gly Val Pro Leu Ser Thr Gln Trp Gly Pro Gln Gly
                165                 170                 175

Tyr Phe Tyr Pro Ile Gln Ile Ala Gln Tyr Gly Leu Ser His Tyr Ser
            180                 185                 190

-continued

```
Lys Asn Leu Thr Glu Arg Pro Pro His Val Glu Val Tyr Asp Thr Ala
        195                 200                 205

Glu Glu Arg Asp Ser Arg Ser Ser Ala Trp Thr Val Pro Lys Gly Cys
    210                 215                 220

Ser Leu Thr Arg Val Tyr Asp Lys Thr Arg Ala Thr Ser Val Arg Gln
225                 230                 235                 240

Phe Ser Ala Pro Glu Asn Ser Glu Gly Val Ser Leu Pro Leu Gly Asn
                245                 250                 255

Thr Lys Asp Phe Ile Ile Ser Phe Asp Leu Lys Phe Thr Ser Asn Gly
            260                 265                 270

Ser Val Ser Val Val Leu Glu Thr Thr Glu Lys Gly Pro Pro Phe Thr
        275                 280                 285

Ile His Tyr Val Thr Thr Thr Gln Leu Ile Ala Phe Lys Asp Arg Asp
    290                 295                 300

Ile Thr Tyr Gly Ile Gly Pro Arg Thr Thr Trp Ser Thr Val Thr Arg
305                 310                 315                 320

Asp Leu Leu Thr Asp Leu Arg Lys Gly Val Gly Leu Ser Asn Thr Lys
                325                 330                 335

Ala Val Lys Ala Thr Lys Ile Met Pro Arg Arg Val Val Arg Leu Val
            340                 345                 350

Val His Gly Thr Gly Phe Ile Asp Asn Ile Thr Ile Ser Thr Thr Ala
        355                 360                 365

His Met Ala Ala Phe Phe Ala Ala Ser Asp Trp Leu Val Arg Asn Gln
    370                 375                 380

Asp Glu Arg Gly Gly Trp Pro Ile Met Val Thr Arg Lys Leu Gly Glu
385                 390                 395                 400

Gly Phe Arg Ala Leu Glu Pro Gly Trp Tyr Ser Ala Met Ala Gln Gly
                405                 410                 415

Gln Ala Met Ser Thr Leu Val Arg Ala Tyr Leu Leu Thr Lys Asp Asp
            420                 425                 430

Arg Tyr Leu Lys Ala Ala Leu Arg Ala Thr Gly Pro Tyr Lys Leu Pro
        435                 440                 445

Ser Glu Gln His Gly Val Lys Ala Val Phe Met Asn Lys Tyr Asp Trp
    450                 455                 460

Tyr Glu Glu Tyr Pro Thr Ile Pro Ser Ser Phe Val Leu Asn Gly Phe
465                 470                 475                 480

Ile Tyr Ser Leu Ile Gly Leu Tyr Asp Leu Ala Glu Thr Ala Gly Glu
                485                 490                 495

Lys Leu Gly Arg Glu Ala Gly Gln Leu Tyr Ser Arg Gly Met Glu Ser
            500                 505                 510

Leu Lys Ala Met Leu Pro Leu Tyr Asp Thr Gly Ser Gly Thr Ile Tyr
        515                 520                 525

Asp Leu Arg His Phe Met Leu Gly Thr Ala Pro Asn Leu Ala Arg Trp
    530                 535                 540

Asp Tyr His Thr Thr His Ile Asn Gln Leu Gln Leu Leu Gly Thr Ile
545                 550                 555                 560

Asp Asn Ser Pro Ile Phe Arg Asp Phe Val Lys Arg Trp Lys Ser Tyr
                565                 570                 575

Leu Lys Gly Gly Arg Ala Lys His Asn
            580                 585
```

<210> SEQ ID NO 64
<211> LENGTH: 1548

```
<212> TYPE: DNA
<213> ORGANISM: Danio rerio

<400> SEQUENCE: 64

ggcgttcggt atgaagaaat cgactgcctg attaacgatg aagcgacgat caaaggacgg     60

cgtgaaggtt ccgaagtgta tctgccgttt agctggatgg aaaagtattt cgaagtctat    120

ggcaaagtcg tacagtacga cggttatgac cgtttcgaat ttagtcactc atattcgaag    180

gtttatgctc agcgtgagcc ctatcatcca gatggtgtgt tcatgtcgtt tgaaggttac    240

aacgtggaag tccgtgatcg tgtcaaatgc atctcaggcg tagaaggtgt gcccttatct    300

acacaatggg gtccgcaggg ttacttctac ccgattcaga tcgcgcaata tgggctgagc    360

cactacagca agaacttgac ggaacgccca cctcatgtag aggtctatga taccgctgag    420

gaacgcgata gtcgctcatc tgcctggacc gtgcccaaag gctgttcgtt aacccgcgtg    480

tatgacaaga cccgcgcgac ctccgttcgc cagttttctg ctccggaaaa ttcggaaggc    540

gttagcttac cgctgggtaa cacgaaagat ttcatcatta gctttgatct caaatttacg    600

agcaatggct ccgttagcgt tgtcctggaa acgaccgaga aaggcccgcc ttttaccatc    660

cactatgtga cgactaccca gctgattgcc ttcaaagatc gcgatattac ctatggtatt    720

ggaccgcgta ctacctggtc cactgttaca cgcgatttgc tcacagatct gcgcaaaggc    780

gttggcctga gcaacactaa agcggtgaaa gcaaccaaga tcatgccgcg tcgtgttgta    840

cggcttgttg tgcatgggac tgggttcatt gacaacatta ccatctctac taccgcccat    900

atggccgcat tctttgcggc aagcgattgg ttagtgcgca atcaggacga acgcggagga    960

tggccgatca tggtaacccg caaacttggg gaaggctttc gtgcactgga accaggctgg   1020

tacagtgcga tggctcaagg tcaagccatg agtaccctgg tccgcgccta tctcctgacg   1080

aaagatgatc gctatctgaa ggccgcactg cgtgcaacag gcccttacaa acttccgtct   1140

gaacaacatg gcgtcaaagc cgtgtttatg aacaaatacg actggtacga agagtatccg   1200

acgattcctt ccagcttcgt gttgaatggc tttatctact cgttaattgg cttgtatgat   1260

ctggcggaaa ctgcgggcga gaaactgggt cgtgaagcgg ggcagctgta cagtcgcggt   1320

atggagtcgc tgaaagcgat gctgccatta tacgacacgg gaagtggcac gatttacgat   1380

ctgcgccact ttatgctggg tacagcgccg aatctcgcac gttgggacta ccataccacc   1440

catattaacc agttgcagct gcttggtacg atcgacaatt caccgatttt ccgcgatttt   1500

gtgaaacggt ggaaatcata tctgaaaggc ggtcgcgcaa agcataat                 1548


<210> SEQ ID NO 65
<211> LENGTH: 516
<212> TYPE: PRT
<213> ORGANISM: Danio rerio

<400> SEQUENCE: 65

Gly Val Arg Tyr Glu Glu Ile Asp Cys Leu Ile Asn Asp Glu Ala Thr
1               5                   10                  15

Ile Lys Gly Arg Arg Glu Gly Ser Glu Val Tyr Leu Pro Phe Ser Trp
            20                  25                  30

Met Glu Lys Tyr Phe Glu Val Tyr Gly Lys Val Val Gln Tyr Asp Gly
        35                  40                  45

Tyr Asp Arg Phe Glu Phe Ser His Ser Tyr Ser Lys Val Tyr Ala Gln
    50                  55                  60

Arg Glu Pro Tyr His Pro Asp Gly Val Phe Met Ser Phe Glu Gly Tyr
65                  70                  75                  80
```

-continued

```
Asn Val Glu Val Arg Asp Arg Val Lys Cys Ile Ser Gly Val Glu Gly
                85                  90                  95

Val Pro Leu Ser Thr Gln Trp Gly Pro Gln Gly Tyr Phe Tyr Pro Ile
            100                 105                 110

Gln Ile Ala Gln Tyr Gly Leu Ser His Tyr Ser Lys Asn Leu Thr Glu
        115                 120                 125

Arg Pro Pro His Val Glu Val Tyr Asp Thr Ala Glu Glu Arg Asp Ser
    130                 135                 140

Arg Ser Ser Ala Trp Thr Val Pro Lys Gly Cys Ser Leu Thr Arg Val
145                 150                 155                 160

Tyr Asp Lys Thr Arg Ala Thr Ser Val Arg Gln Phe Ser Ala Pro Glu
                165                 170                 175

Asn Ser Glu Gly Val Ser Leu Pro Leu Gly Asn Thr Lys Asp Phe Ile
            180                 185                 190

Ile Ser Phe Asp Leu Lys Phe Thr Ser Asn Gly Ser Val Ser Val Val
        195                 200                 205

Leu Glu Thr Thr Glu Lys Gly Pro Pro Phe Thr Ile His Tyr Val Thr
    210                 215                 220

Thr Thr Gln Leu Ile Ala Phe Lys Asp Arg Asp Ile Thr Tyr Gly Ile
225                 230                 235                 240

Gly Pro Arg Thr Thr Trp Ser Thr Val Thr Arg Asp Leu Leu Thr Asp
                245                 250                 255

Leu Arg Lys Gly Val Gly Leu Ser Asn Thr Lys Ala Val Lys Ala Thr
            260                 265                 270

Lys Ile Met Pro Arg Arg Val Val Arg Leu Val Val His Gly Thr Gly
        275                 280                 285

Phe Ile Asp Asn Ile Thr Ile Ser Thr Thr Ala His Met Ala Ala Phe
    290                 295                 300

Phe Ala Ala Ser Asp Trp Leu Val Arg Asn Gln Asp Glu Arg Gly Gly
305                 310                 315                 320

Trp Pro Ile Met Val Thr Arg Lys Leu Gly Glu Gly Phe Arg Ala Leu
                325                 330                 335

Glu Pro Gly Trp Tyr Ser Ala Met Ala Gln Gly Gln Ala Met Ser Thr
            340                 345                 350

Leu Val Arg Ala Tyr Leu Leu Thr Lys Asp Asp Arg Tyr Leu Lys Ala
        355                 360                 365

Ala Leu Arg Ala Thr Gly Pro Tyr Lys Leu Pro Ser Glu Gln His Gly
    370                 375                 380

Val Lys Ala Val Phe Met Asn Lys Tyr Asp Trp Tyr Glu Glu Tyr Pro
385                 390                 395                 400

Thr Ile Pro Ser Ser Phe Val Leu Asn Gly Phe Ile Tyr Ser Leu Ile
                405                 410                 415

Gly Leu Tyr Asp Leu Ala Glu Thr Ala Gly Glu Lys Leu Gly Arg Glu
            420                 425                 430

Ala Gly Gln Leu Tyr Ser Arg Gly Met Glu Ser Leu Lys Ala Met Leu
        435                 440                 445

Pro Leu Tyr Asp Thr Gly Ser Gly Thr Ile Tyr Asp Leu Arg His Phe
    450                 455                 460

Met Leu Gly Thr Ala Pro Asn Leu Ala Arg Trp Asp Tyr His Thr Thr
465                 470                 475                 480

His Ile Asn Gln Leu Gln Leu Leu Gly Thr Ile Asp Asn Ser Pro Ile
                485                 490                 495
```

```
Phe Arg Asp Phe Val Lys Arg Trp Lys Ser Tyr Leu Lys Gly Gly Arg
            500                 505                 510

Ala Lys His Asn
        515


<210> SEQ ID NO 66
<211> LENGTH: 585
<212> TYPE: PRT
<213> ORGANISM: Danio rerio

<400> SEQUENCE: 66

Met Arg Cys Leu Ala Ala Arg Val His Tyr Lys Thr Leu Ile Val Ile
1               5                   10                  15

Cys Ala Leu Leu Ser Leu Leu Thr Val Leu Leu Trp Asn Lys Cys Thr
            20                  25                  30

Ser Glu Lys Ala Leu Arg Phe Leu Pro Gln His Pro Gln Pro Pro Pro
        35                  40                  45

Ser Pro Lys Ile Asp Ser His Pro Gln Gln Pro Gln Pro Pro Glu Pro
    50                  55                  60

Pro Pro Val Val Gly Gly Val Arg Tyr Glu Glu Ile Asp Cys Leu Ile
65                  70                  75                  80

Asn Asp Asp Ala Thr Ile Lys Gly Arg Arg Glu Gly Ser Glu Val Tyr
                85                  90                  95

Leu Pro Phe Ser Trp Met Glu Lys Tyr Phe Glu Val Tyr Gly Lys Val
            100                 105                 110

Val Gln Tyr Asp Gly Tyr Asp Arg Phe Glu Phe Ser His Ser Tyr Ser
        115                 120                 125

Lys Val Tyr Ala Gln Arg Glu Pro Tyr His Pro Asn Gly Val Phe Met
    130                 135                 140

Ser Phe Glu Gly Tyr Asn Val Glu Val Arg Asp Arg Val Lys Cys Ile
145                 150                 155                 160

Ser Gly Val Glu Gly Val Pro Leu Ser Thr Gln Trp Gly Pro Gln Gly
                165                 170                 175

Tyr Phe Tyr Ala Ile Gln Ile Ala Gln Tyr Gly Leu Ser His Tyr Ser
            180                 185                 190

Lys Asn Leu Thr Glu Arg Pro Pro His Val Glu Val Tyr Asp Thr Ala
        195                 200                 205

Glu Glu Arg Asp Ser Arg Ser Ser Ala Trp Thr Val Pro Lys Gly Cys
    210                 215                 220

Ser Leu Thr Arg Val Tyr Asp Lys Thr Arg Ala Thr Ser Val Arg Glu
225                 230                 235                 240

Phe Ser Ala Pro Glu Asn Ser Glu Gly Val Ser Leu Pro Leu Gly Asn
                245                 250                 255

Thr Lys Asp Phe Ile Ile Ser Phe Asp Leu Lys Phe Thr Ser Asn Gly
            260                 265                 270

Ser Val Ser Val Ile Leu Glu Thr Thr Glu Lys Gly Pro Pro Phe Val
        275                 280                 285

Ile His Tyr Val Thr Thr Thr Gln Leu Ile Leu Phe Lys Asp Arg Asp
    290                 295                 300

Ile Thr Tyr Gly Ile Gly Pro Arg Thr Thr Trp Ser Thr Val Thr Arg
305                 310                 315                 320

Asp Leu Leu Thr Asp Leu Arg Lys Gly Val Gly Leu Ser Asn Thr Lys
                325                 330                 335

Ala Val Lys Ala Thr Lys Thr Met Pro Arg Arg Val Val Lys Leu Val
            340                 345                 350
```

```
Val His Gly Thr Gly Thr Ile Asp Asn Ile Thr Ile Ser Thr Thr Ser
        355                 360                 365

His Met Ala Ala Phe Phe Ala Ala Ser Asp Trp Leu Val Arg Asn Gln
    370                 375                 380

Asp Glu Arg Gly Gly Trp Pro Ile Met Val Thr Arg Lys Leu Gly Glu
385                 390                 395                 400

Gly Phe Arg Ala Leu Glu Pro Gly Trp Tyr Ser Ala Met Ala Gln Gly
                405                 410                 415

Gln Ala Met Ser Thr Leu Val Arg Ala Tyr Leu Leu Thr Lys Asp Asp
            420                 425                 430

Arg Tyr Leu Lys Ala Ala Leu Arg Ala Thr Gly Pro Phe Lys Leu Pro
        435                 440                 445

Ser Glu Gln His Gly Val Lys Ala Val Phe Met Asn Lys Tyr Asp Trp
    450                 455                 460

Tyr Glu Glu Tyr Pro Thr Ile Pro Ser Ser Phe Val Leu Asn Gly Phe
465                 470                 475                 480

Ile Tyr Ser Leu Ile Gly Leu Phe Asp Leu Ala Glu Thr Ala Gly Glu
                485                 490                 495

Lys Leu Gly Arg Glu Ala Gly Gln Leu Tyr Ser Lys Gly Met Glu Ser
            500                 505                 510

Leu Lys Ala Met Leu Pro Leu Tyr Asp Thr Gly Ser Gly Thr Ile Tyr
        515                 520                 525

Asp Leu Arg His Phe Ile Leu Gly Thr Ala Pro Asn Leu Ala Arg Trp
    530                 535                 540

Asp Tyr His Thr Thr His Ile Asn Gln Leu Gln Leu Leu Gly Thr Ile
545                 550                 555                 560

Asp Asn Ser Pro Ile Phe Arg Asp Ser Val Lys Arg Trp Lys Ser Tyr
                565                 570                 575

Leu Lys Gly Gly Arg Ala Lys His Asn
            580                 585
```

<210> SEQ ID NO 67
<211> LENGTH: 1548
<212> TYPE: DNA
<213> ORGANISM: Danio rerio

<400> SEQUENCE: 67

```
ggcgttcggt atgaagaaat cgattgcctg atcaacgatg acgccaccat caaaggtcgc      60

cgtgaaggca gcgaagttta tctgccgttc agttggatgg agaagtattt tgaagtctac     120

ggcaaagtgg tgcagtatga cggatatgat cgctttgaat tttctcatag ctactccaaa     180

gtgtacgcac aacgtgaacc ttatcaccca aatggcgtgt tcatgagttt tgagggctat     240

aacgtcgagg tgcgcgaccg tgtgaaatgc atctcaggcg ttgagggagt tccgctttca     300

acccaatggg gtccacaagg ttacttttat gccattcaga tcgcacagta tggtttaagc     360

cattactcga agaaccttac ggaacgccct ccgcatgtgg aagtctatga taccgcggaa     420

gaacgcgatt cacgctcgtc ggcttggacg gtgcctaaag gctgtagctt gacgcgcgtt     480

tatgacaaga cacgcgcaac tagtgtacgc gagttttctg cgcctgaaaa ctccgaaggc     540

gtcagtctgc cactgggcaa taccaaagat ttcattatct cctttgacct taaatttacc     600

tccaatggct ctgtttccgt gattctcgaa accaccgaga aaggcccgcc ctttgtaatt     660

cactacgtca ccaccaccca gctgattctg ttcaaagatc gcgatattac gtatggcatt     720

ggaccgcgta ctacgtggtc gacggtaact cgtgacttat tgactgatct tcggaaaggt     780
```

-continued

```
gtcggcctgt caaacacaaa agcggttaaa gcgaccaaga ccatgccgcg tcgcgtggtt    840

aaactcgtag tacatgggac gggcaccatt gacaacatca ccattagcac gacaagccac    900

atggcggcct tcttcgccgc atctgactgg ctggtacgga atcaggatga acgtggtggc    960

tggccgatca tggttactcg taaactgggt gaagggtttc gtgcattaga accgggctgg   1020

tatagtgcga tggcccaagg tcaggccatg agcaccttag tgcgtgctta tctgctgacg   1080

aaagacgatc ggtacctgaa agcagcttta cgcgccaccg ggccgttcaa attgcccagc   1140

gaacagcatg gtgtcaaagc ggttttcatg aacaagtatg actggtatga agagtaccca   1200

acgattccct cgagctttgt cctgaacggt ttcatttact ctctgattgg cctgtttgat   1260

ctggcggaaa ccgcgggtga aaagctgggt cgtgaggctg gtcagttgta ctcgaaaggg   1320

atggaatccc tgaaggccat gttaccgctg tacgatacag ggtcaggcac catctatgat   1380

ctgcgccatt tcattctggg tactgctccg aatctcgcgc gttgggatta ccatactacg   1440

cacattaacc aactccagct gctgggaaca atcgataata gcccgatctt tcgcgatagc   1500

gtgaaacgct ggaaaagtta cttgaaaggc ggtcgcgcaa agcataat               1548
```

<210> SEQ ID NO 68
<211> LENGTH: 516
<212> TYPE: PRT
<213> ORGANISM: Danio rerio

<400> SEQUENCE: 68

```
Gly Val Arg Tyr Glu Glu Ile Asp Cys Leu Ile Asn Asp Asp Ala Thr
1               5                   10                  15

Ile Lys Gly Arg Arg Glu Gly Ser Glu Val Tyr Leu Pro Phe Ser Trp
            20                  25                  30

Met Glu Lys Tyr Phe Glu Val Tyr Gly Lys Val Val Gln Tyr Asp Gly
        35                  40                  45

Tyr Asp Arg Phe Glu Phe Ser His Ser Tyr Ser Lys Val Tyr Ala Gln
    50                  55                  60

Arg Glu Pro Tyr His Pro Asn Gly Val Phe Met Ser Phe Glu Gly Tyr
65                  70                  75                  80

Asn Val Glu Val Arg Asp Arg Val Lys Cys Ile Ser Gly Val Glu Gly
                85                  90                  95

Val Pro Leu Ser Thr Gln Trp Gly Pro Gln Gly Tyr Phe Tyr Ala Ile
            100                 105                 110

Gln Ile Ala Gln Tyr Gly Leu Ser His Tyr Ser Lys Asn Leu Thr Glu
        115                 120                 125

Arg Pro Pro His Val Glu Val Tyr Asp Thr Ala Glu Glu Arg Asp Ser
    130                 135                 140

Arg Ser Ser Ala Trp Thr Val Pro Lys Gly Cys Ser Leu Thr Arg Val
145                 150                 155                 160

Tyr Asp Lys Thr Arg Ala Thr Ser Val Arg Glu Phe Ser Ala Pro Glu
                165                 170                 175

Asn Ser Glu Gly Val Ser Leu Pro Leu Gly Asn Thr Lys Asp Phe Ile
            180                 185                 190

Ile Ser Phe Asp Leu Lys Phe Thr Ser Asn Gly Ser Val Ser Val Ile
        195                 200                 205

Leu Glu Thr Thr Glu Lys Gly Pro Pro Phe Val Ile His Tyr Val Thr
    210                 215                 220

Thr Thr Gln Leu Ile Leu Phe Lys Asp Arg Asp Ile Thr Tyr Gly Ile
225                 230                 235                 240
```

```
Gly Pro Arg Thr Thr Trp Ser Thr Val Thr Arg Asp Leu Leu Thr Asp
                245                 250                 255

Leu Arg Lys Gly Val Gly Leu Ser Asn Thr Lys Ala Val Lys Ala Thr
            260                 265                 270

Lys Thr Met Pro Arg Arg Val Val Lys Leu Val Val His Gly Thr Gly
        275                 280                 285

Thr Ile Asp Asn Ile Thr Ile Ser Thr Thr Ser His Met Ala Ala Phe
    290                 295                 300

Phe Ala Ala Ser Asp Trp Leu Val Arg Asn Gln Asp Glu Arg Gly Gly
305                 310                 315                 320

Trp Pro Ile Met Val Thr Arg Lys Leu Gly Glu Gly Phe Arg Ala Leu
                325                 330                 335

Glu Pro Gly Trp Tyr Ser Ala Met Ala Gln Gly Gln Ala Met Ser Thr
            340                 345                 350

Leu Val Arg Ala Tyr Leu Leu Thr Lys Asp Asp Arg Tyr Leu Lys Ala
        355                 360                 365

Ala Leu Arg Ala Thr Gly Pro Phe Lys Leu Pro Ser Glu Gln His Gly
    370                 375                 380

Val Lys Ala Val Phe Met Asn Lys Tyr Asp Trp Tyr Glu Glu Tyr Pro
385                 390                 395                 400

Thr Ile Pro Ser Ser Phe Val Leu Asn Gly Phe Ile Tyr Ser Leu Ile
                405                 410                 415

Gly Leu Phe Asp Leu Ala Glu Thr Ala Gly Glu Lys Leu Gly Arg Glu
            420                 425                 430

Ala Gly Gln Leu Tyr Ser Lys Gly Met Glu Ser Leu Lys Ala Met Leu
        435                 440                 445

Pro Leu Tyr Asp Thr Gly Ser Gly Thr Ile Tyr Asp Leu Arg His Phe
    450                 455                 460

Ile Leu Gly Thr Ala Pro Asn Leu Ala Arg Trp Asp Tyr His Thr Thr
465                 470                 475                 480

His Ile Asn Gln Leu Gln Leu Leu Gly Thr Ile Asp Asn Ser Pro Ile
                485                 490                 495

Phe Arg Asp Ser Val Lys Arg Trp Lys Ser Tyr Leu Lys Gly Gly Arg
            500                 505                 510

Ala Lys His Asn
        515
```

<210> SEQ ID NO 69
<211> LENGTH: 35
<212> TYPE: DNA
<213> ORGANISM: Artificial Sequence
<220> FEATURE:
<223> OTHER INFORMATION: primer

<400> SEQUENCE: 69
gccgcgtctt ctggaggcct gaaatacgag gaaat 35

<210> SEQ ID NO 70
<211> LENGTH: 38
<212> TYPE: DNA
<213> ORGANISM: Artificial Sequence
<220> FEATURE:
<223> OTHER INFORMATION: primer

<400> SEQUENCE: 70
ggatccgagc tcgagttagt tatgtttggc gcgtccgc 38

-continued

```
<210> SEQ ID NO 71
<211> LENGTH: 36
<212> TYPE: DNA
<213> ORGANISM: Artificial Sequence
<220> FEATURE:
<223> OTHER INFORMATION: primer

<400> SEQUENCE: 71

gccgcgtctt ctggaggtct gaaatatgaa gagatt                          36


<210> SEQ ID NO 72
<211> LENGTH: 36
<212> TYPE: DNA
<213> ORGANISM: Artificial Sequence
<220> FEATURE:
<223> OTHER INFORMATION: primer

<400> SEQUENCE: 72

gccgcgtctt ctggaggcgt caagtacgaa gaaatc                          36
```

METHOD FOR PRODUCING HEPAROSAN COMPOUND HAVING ISOMERIZED HEXURONIC ACID RESIDUE

This application is a Continuation of, and claims priority under 35 U.S.C. § 120 to, International Application No. PCT/JP2017/030998, filed Aug. 29, 2017, and claims priority therethrough under 35 U.S.C. § 119 to Japanese Patent Application No. 2017-007900, filed Jan. 19, 2017, the entireties of which are incorporated by reference herein. Also, the Sequence Listing filed electronically herewith is hereby incorporated by reference (File name: 2019-07-17T_US-596_Seq_List; File size: 152 KB; Date recorded: Jul. 17, 2019).

TECHNICAL FIELD

The present invention relates to a method for producing a heparosan compound having an isomerized hexuronic acid residue and a method for producing a heparan sulfate.

BACKGROUND ART

Heparin is a compound which is a kind of heparan sulfate, and has anticoagulant activity. Animal-derived heparin has problems in quality control, and so development of quality-controlled non-animal-derived heparin has been investigated. Examples of a method for producing non-animal-derived heparin include a method for producing heparin by subjecting heparosan produced using a microorganism to sulfation and isomerization reactions, for example (see Patent Literatures 1 and 2, Non-Patent Literatures 1 to 3).

Heparosan is a polysaccharide composed of repetitive structures of a disaccharide composed of a glucuronic acid (GlcA) residue and an N-acetyl-D-glucosamine (GlcNAc) residue [→4)-β-D-GlcA-(1→4)-α-D-GlcNAc-(1→]. Heparin has a structure where some of the D-glucuronic acid residues in heparosan are isomerized to α-L-iduronic acids (IdoA), which are the epimers. Therefore, in order to produce a heparan sulfate such as heparin from heparosan, a reaction for isomerizing a part of a hexuronic acid residue, i.e., a reaction for isomerizing the part of the D-glucuronic acid residues to α-L-iduronic acids (C5-epimerization reaction), is required. The C5-epimerization reaction includes enzymatic procedures using D-glucuronyl C5-epimerase. As C5-epimerase, utilization of mammal-derived C5-epimerase has been reported (see Patent Literatures 1 to 3, Non-Patent Literatures 1 to 3). In addition, a marine bacterium-derived protein which catalyzes the C5-epimerization reaction has been also identified (Non-Patent Literature 4). However, none of these enzymes have sufficient C-5 epimerization activity, and so more efficient enzymes are required.

PATENT LITERATURE

Patent literature 1: U.S. Pat. No. 8,227,449

Patent literature 2: US Patent Application Publication No. 2012-322114

Patent literature 3: WO 02/46379 A

NON-PATENT LITERATURE

Non-patent literature 1: Lindahl U. et al. (2005) J Med Chem 48(2):349-352

Non-patent literature 2: Zhang Z. et al.(2008) Journal of the American Chemical Society 130(39):12998-13007

Non-patent literature 3: Chen J, et al., J Biol Chem. 2005 December 30; 280 (52):42817-25.

Non-patent literature 4: John R, et al., J Biol Chem. 2013 August 23; 288(34):24332-9.

SUMMARY

An aspect of the present invention is to provide an efficient method for producing a heparan sulfate.

It has been found that C5-epimerization, which is required for the production of heparan sulfate, can be efficiently performed using a series of proteins having 80% or more sequence homology to D-glucuronyl C5-epimerase derived from zebrafish (see Table 4).

It is one aspect of the present invention to provide a method for producing a heparosan compound having an isomerized hexuronic acid residue, said method comprising producing the heparosan compound having the isomerized hexuronic acid residue from a heparosan compound in the presence of a protein selected from the group of consisting of: (A) a protein comprising the amino acid sequence of SEQ ID No:2; (B) a protein which comprises an amino acid sequence having 80% or more homology to the amino acid sequence of SEQ ID No:2 and has a D-glucuronyl C5-epimerase activity; (C) a protein which comprises an amino acid sequence having one or several deleted, substituted, added or inserted amino acid residues in the amino acid sequence of SEQ ID No:2 and has a D-glucuronyl C5-epimerase activity; (D) a protein comprising the amino acid sequence of SEQ ID NO:5; (E) a protein which comprises an amino acid sequence having 80% or more homology to the amino acid sequence of SEQ ID No:5 and has a D-glucuronyl C5-epimerase activity; and (F) a protein which comprises an amino acid sequence having one or several deleted, substituted, added or inserted amino acid residues in the amino acid sequence of SEQ ID No:5 and has a D-glucuronyl C5-epimerase activity.

It is a further aspect of the present invention to provide the method as described above, wherein the protein (B) comprises an amino acid sequence having 90% or more homology to the amino acid sequence of SEQ ID No:2 and has a D-glucuronyl C5-epimerase activity, and wherein the protein (E) comprises an amino acid sequence having 90% or more homology to the amino acid sequence of SEQ ID No:5 and has a D-glucuronyl C5-epimerase activity.

It is a further aspect of the present invention to provide the method as described above, wherein said protein is selected from the group consisting of: (E1) a protein comprising an amino acid sequence selected from the group consisting of SEQ ID NOS:56, 59, 62, 65 and 68; (E2) a protein which comprises an amino acid sequence having 95% or more homology to an amino acid sequence selected from the group consisting of SEQ ID NOS:59, 62, 65 and 68 and has a D-glucuronyl C5-epimerase activity; and (F1) a protein which comprises an amino acid sequence having 1 to 25 deleted, substituted, added or inserted amino acid residues in an amino acid sequence selected from the group consisting of SEQ ID NOS:59, 62, 65 and 68 and has a D-glucuronyl C5-epimerase activity.

It is a further aspect of the present invention to provide the method as described above, wherein said protein is derived from zebrafish.

It is a further aspect of the present invention to provide the method as described above, wherein the heparosan compound having the isomerized hexuronic acid residue is produced in the presence of a transformed microorganism producing said protein or an extract thereof.

It is a further aspect of the present invention to provide the method as described above, wherein said transformed microorganism is a host cell comprising an expression unit comprising a promoter operably linked to a polynucleotide selected from the group consisting of: (a) a polynucleotide comprising the nucleotide sequence of SEQ ID NO:1; (b) a polynucleotide which comprises a nucleotide sequence having 80% or more homology to the nucleotide sequence of SEQ ID NO:1 and encodes a protein having a D-glucuronyl C5-epimerase activity; (c) a polynucleotide which hybridizes with a polynucleotide consisting of the nucleotide sequence complementary to the nucleotide sequence of SEQ ID NO:1 under the stringent conditions and encodes a protein having a D-glucuronyl C5-epimerase activity; (d) a polynucleotide comprising the nucleotide sequence of SEQ ID NO:3; (e) a polynucleotide which comprises a nucleotide sequence having 80% or more homology to the nucleotide sequence of SEQ ID NO:3 and encodes a protein having a D-glucuronyl C5-epimerase activity; (f) a polynucleotide which hybridizes with a polynucleotide consisting of the nucleotide sequence complementary to the nucleotide sequence of SEQ ID NO:3 under the stringent conditions and encodes a protein having a D-glucuronyl C5-epimerase activity; (g) a polynucleotide comprising the nucleotide sequence of SEQ ID NO:4; (h) a polynucleotide which comprises a nucleotide sequence having 80% or more homology to the nucleotide sequence of SEQ ID NO:4 and encodes a protein having a D-glucuronyl C5-epimerase activity; (i) a polynucleotide which hybridizes with a polynucleotide consisting of the nucleotide sequence complementary to the nucleotide sequence of SEQ ID NO:4 under the stringent conditions and encodes a protein having a D-glucuronyl C5-epimerase activity; and (j) a degenerate mutant of a polynucleotide selected from the group consisting of (a) to (i).

It is a further aspect of the present invention to provide the method as described above, wherein the polynucleotide (b) is comprises a nucleotide sequence having 90% or more homology to the nucleotide sequence of SEQ ID NO:1 and encodes a protein having a D-glucuronyl C5-epimerase activity, wherein the polynucleotide (e) comprises a nucleotide sequence having 90% or more homology to the nucleotide sequence of SEQ ID NO:3 and encodes a protein having a D-glucuronyl C5-epimerase activity, and wherein the polynucleotide (h) comprises a nucleotide sequence having 90% or more homology to the nucleotide sequence of SEQ ID NO:4 and encodes a protein having a D-glucuronyl C5-epimerase activity.

It is a further aspect of the present invention to provide the method as described above, wherein said polynucleotide is selected from the group consisting of: (e1) a polynucleotide comprising a nucleotide sequence selected from the group consisting of SEQ ID NOS:55, 58, 61, 64 and 67; (e2) a polynucleotide which comprises a nucleotide sequence having 95% or more homology to a nucleotide sequence selected from the group consisting of SEQ ID NOS:58, 61, 64 and 67 and encodes a protein having a D-glucuronyl C5-epimerase activity; and (j1) a degenerate mutant of the polynucleotide (e1) or (e2).

It is a further aspect of the present invention to provide the method as described above, wherein said transformed microorganism is a bacterium belonging to genus *Escherichia.*

It is a further aspect of the present invention to provide the method as described above, wherein said transformed microorganism is *Escherichia coli.*

It is a further aspect of the present invention to provide the method as described above, wherein said heparosan compound is an N-sulfated heparosan.

It is a further aspect of the present invention to provide the method as described above, wherein said heparosan compound is a low-molecularized heparosan.

It is a further aspect of the present invention to provide a method for producing heparan sulfate, said method comprising subjecting a heparosan to a treatment comprising C5-epimerization of a hexuronic acid residue, 2-O-sulfation of a hexuronic acid residue, N-deacetylation of an α-D-glucosamine residue, N-sulfation of an α-D-glucosamine residue, 3-O-sulfation of an α-D-glucosamine residue, and 6-O-sulfation of an α-D-glucosamine residue to produce the heparan sulfate, wherein the C5-epimerization is performed in the presence of a protein selected from the group consisting of: (A) a protein comprising the amino acid sequence of SEQ ID NO:2; (B) a protein which comprises an amino acid sequence having 80% or more identity to the amino acid sequence of SEQ ID NO:2 and has a D-glucuronyl C5-epimerase activity; (C) a protein which comprises an amino acid sequence having one or several deleted, substituted, added or inserted amino acid residues in the amino acid sequence of SEQ ID NO:2 and has a D-glucuronyl C5-epimerase activity; (D) a protein comprising the amino acid sequence of SEQ ID NO:5; (E) a protein which comprises an amino acid sequence having 80% or more identity to the amino acid sequence of SEQ ID NO:5 and has a D-glucuronyl C5-epimerase activity; and (F) a protein which comprises an amino acid sequence having one or several deleted, substituted, added or inserted amino acid residues in the amino acid sequence of SEQ ID NO:5 and has a D-glucuronyl C5-epimerase activity.

It is a further aspect of the present invention to provide the method as described above, wherein the protein (B) comprises an amino acid sequence having 90% or more identity to the amino acid sequence of SEQ ID NO:2 and has a D-glucuronyl C5-epimerase activity, and wherein the protein (E) comprises an amino acid sequence having 90% or more identity to the amino acid sequence of SEQ ID NO:5 and has a D-glucuronyl C5-epimerase activity.

It is a further aspect of the present invention to provide the method as described above, wherein said protein is selected from the group consisting of: (E1) a protein comprising an amino acid sequence selected from the group consisting of SEQ ID NOS:56, 59, 62, 65 and 68; (E2) a protein which comprises an amino acid sequence having 95% or more homology to an amino acid sequence selected from the group consisting of SEQ ID NOS:59, 62, 65 and 68, and has a D-glucuronyl C5-epimerase activity; and (F1) a protein which comprises an amino acid sequence having 1 to 25 deleted, substituted, added or inserted amino acid residues in an amino acid sequence selected from the group consisting of SEQ ID NOS:59, 62, 65 and 68 and has a D-glucuronyl C5-epimerase activity.

It is a further aspect of the present invention to provide the method as described above, wherein the treatment further comprises low-molecularizing a heparosan.

It is a further aspect of the present invention to provide a protein selected from the group consisting of: (E1) a protein comprising an amino acid sequence selected from the group consisting of SEQ ID NOS:56, 59, 62, 65 and 68; (E2) a protein which comprises an amino acid sequence having 95% or more homology to an amino acid sequence selected from the group consisting of SEQ ID NOS:59, 62, 65 and 68 and has a D-glucuronyl C5-epimerase activity; and (F1) a protein which comprises an amino acid sequence having 1 to 25 deleted, substituted, added or inserted amino acid residues in an amino acid sequence selected from the group consisting of SEQ ID NOS:59, 62, 65 and 68, and has a D-glucuronyl C5-epimerase activity.

BRIEF DESCRIPTION OF DRAWINGS

FIG. 1 shows the full-length nucleotide sequence (GenBank Accession No: AY388517.1, SEQ ID NO:1) encoding a naturally occurring D-glucuronyl C5-epimerase derived from zebrafish. The sequence surrounded by the framework in this figure shows a naturally occurring nucleotide sequence (SEQ ID NO:3) encoding the partial amino acid sequence (Gly70 to Asn585 in SEQ ID NO:2: SEQ ID NO:5).

FIG. 2 shows the full-length amino acid sequence (GenBank Accession No: AY388517.1, SEQ ID NO:2) of the naturally occurring D-glucuronyl C5-epimerase derived from zebrafish. The sequence surrounded by the framework in this figure (partial amino acid sequence from Gly70 to Asn585) corresponds to SEQ ID NO:5 (see Example 2).

FIG. 3 shows a codon-optimized nucleotide sequence (SEQ ID NO:4) encoding the partial amino acid sequence (SEQ ID NO:5) of D-glucuronyl C5-epimerase derived from zebrafish (see Example 2).

DETAILED DESCRIPTION

Described herein is a method for producing a heparosan compound having an isomerized hexuronic acid residue from a heparosan compound in the presence of one of the following proteins: (A) a protein including the amino acid sequence of SEQ ID No:2; (B) a protein which includes an amino acid sequence having 80% or more homology to the amino acid sequence of SEQ ID No:2 and has a D-glucuronyl C5-epimerase activity; (C) a protein which includes an amino acid sequence having one or several deleted, substituted, added or inserted amino acid residues in the amino acid sequence of SEQ ID No:2 and has a D-glucuronyl C5-epimerase activity; (D) a protein including the amino acid sequence of SEQ ID NO:5; (E) a protein which includes an amino acid sequence having 80% or more homology to the amino acid sequence of SEQ ID No:5 and has a D-glucuronyl C5-epimerase activity; and (F) a protein which includes an amino acid sequence having one or several deleted, substituted, added or inserted amino acid residues in the amino acid sequence of SEQ ID No:5 and has a D-glucuronyl C5-epimerase activity.

The protein may be one of the following: (E1) a protein including an amino acid sequence of SEQ ID NOS:56, 59, 62, 65 or 68; (E2) a protein which includes an amino acid sequence having 95% or more homology to an amino acid sequence of SEQ ID NOS:59, 62, 65 or 68, and has a D-glucuronyl C5-epimerase activity; and (F1) a protein which includes an amino acid sequence having 1 to 25 deleted, substituted, added or inserted amino acid residues in an amino acid sequence of SEQ ID NOS:59, 62, 65 or 68, and has a D-glucuronyl C5-epimerase activity.

The "heparosan compounds" include heparosan and heparosan derivatives. Heparosan can be produced, for example, by a fermentation method utilizing a microorganism having an ability to produce heparosan (e.g., WO2015/050184).

The "heparosan derivative" refers to heparosan having one or more (e.g., 1, 2, 3, 4, 5 or 6) of the following modifications: (1) low molecularization; (2) N-deacetylation of an N-acetyl group of an α-D-glucosamine residue in heparosan (e.g., partial N-deacetylation); (3) N-sulfation of an amino group of an α-D-glucosamine residue in heparosan; (4) sulfation of a hydroxyl group at position 2 of a hexuronic acid residue in heparosan (2-O-sulfation); (5) sulfation of a hydroxyl group at position 3 of an α-D-glucosamine residue (3-O-sulfation); and (6) sulfation of a hydroxyl group at position 6 of an α-D-glucosamine residue (6-O-sulfation).

Such derivatives can be obtained by utilizing N-deacetylation of the α-D-glucosamine residue, low molecularization, N-sulfation of the α-D-glucosamine residue, 2-O-sulfation of the hexuronic acid residue, 3-O-sulfation of the α-D-glucosamine residue, and 6-O-sulfation of the α-D-glucosamine residue as described herein.

In one embodiment, the heparosan compound may be N-sulfated heparosan. N-Sulfated heparosan can be obtained by, for example, subjecting heparosan to the N-deacetylation, such as partial N-deacetylation, and the N-sulfation described herein.

In another embodiment, the heparosan compound may be a small molecular heparosan compound. The small molecule heparosan compound can be obtained by, for example, subjecting heparosan to a treatment of low molecularization as described herein.

In some embodiments, the heparosan compound may be N-sulfated small molecule heparosan. The N-sulfated small molecule heparosan can be obtained by, for example, subjecting the heparosan compound to the treatments of N-deacetylation, such as partial N-deacetylation, decomposition into low molecules and N-sulfation as described herein.

The term "hexuronic acid (HexA)" can be used as an inclusive term for a β-D-glucuronic acid (GlcA) and an α-L-iduronic acid (IdoA). The term "hexuronic acid (HexA)", i.e., the terms, "β-D-glucuronic acid (GlcA)" and "α-L-iduronic acid (IdoA)" includes all possible derivatives depending on the embodiments described herein, unless otherwise specified. The term "α-D-glucosamine" includes potentially all derivatives depending on embodiments described herein, unless otherwise specified. In the HexA residue having the double bond between C-4 and C-5, the IdoA residue and the GlcA residue are not distinguished. Thus, when each parameter which identifies the polysaccharide such as the polysaccharide as described herein is calculated, such a HexA residue is addressed as one corresponding to the HexA residue but corresponding to neither the IdoA residue nor the GlcA residue unless otherwise specified.

The "heparosan compound having an isomerized hexuronic acid residue" is a compound having an isomerization of a part of glucuronic acid (GlcA) residue to an iduronic acid (IdoA) residue. The isomerization of the glucuronic acid (GlcA) residue to the iduronic acid (IdoA) residue is referred to as "C5-epimerization". A "D-glucuronyl C5-epimerase activity" is an activity which can catalyze the isomerization of the glucuronic acid (GlcA) residue to the iduronic acid (IdoA) residue (C5-epimerization). Reaction conditions for the C5-epimerization can be appropriately configured by a person skilled in the art. As reaction conditions for the C5-epimerization, the previously reported conditions (Chen J, et al., "Enzymatic redesigning of biologically active heparan sulfate." J. Biol. Chem. 2005 Dec. 30; 280(52): 42817-25) can be referenced. Specifically, the reaction conditions for the C5-epimerization include, for example, the conditions described in the Examples. The degree of the C5-epimerization (i.e., epimerization rate) can be confirmed, for example, by the disaccharide analysis. That is, the epimerization rate can be calculated as a percentage (molar ratio) of the amount of the disaccharide units having the IdoA residue relative to a total amount of the disaccharide units having the IdoA residue or the GlcA residue when the polysaccharide is subjected to the disaccharide analysis.

The amino acid sequence of SEQ ID NO:5 corresponds to a partial amino acid sequence (Gly70 to Asn585) of SEQ ID NO:2, and has a deletion of the amino acid sequence including the membrane anchor site (Met1 to Gly69). The amino acid sequences of SEQ ID NOS:56, 59, 62, 65 and 68 are obtained by modifying the amino acid sequence of SEQ ID NO:5.

In Protein (B) or (E), the homology percentage with an amino acid sequence of SEQ ID NO: 2 or 5 may be 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, or 99% or higher. In Protein (E2), the homology percentage with an amino acid sequence of SEQ ID NOS:59, 62, 65 or 68 may be 95% or higher, 96% or higher, 97% or higher, 98% or higher, 99% or higher, or 99.5% or higher. The homology, that is, identity or similarity, of the amino acid sequence described above and a nucleotide sequence described below can be determined, for example, using the algorithm BLAST (Pro. Natl. Acad. Sci. USA, 90, 5873 (1993)) by Karlin and Altscchul and FASTA (Methods Enzymol., 183, 63(1990)) by Pearson. Based on this algorithm BLAST, programs called BLASTP and BLASTN have been developed (see ncbi.nlm.nih.gov), and the homology may be calculated using these programs by default setting. For the homology, a value when similarity is calculated in terms of percentage with a setting of Unit Size to Compare =2 using full-length polypeptide portion encoded in an ORF using GENETYX Ver. 7.0.9, software by Genetyx Corporation, adopting the Lipman-Pearson method may be used, for example. Alternatively, the homology may be a value (Identity) obtained by using parameters (Gap penalty=10, Extend penalty=0.5, and Matrix=EBLOSUM62) in default setting in a NEEDLE program (J. Mol. Biol. 1970; 48: 443-453) search. Among the values of the homology percentage derived by these calculations, the lowest value may be used. For the homology percentage, identity percentage is one example.

In proteins (C), (F) or (F1), one or several amino acid residues can be modified by one, two, three or four mutations including deletion, substitution, addition and insertion of amino acid residues. The mutations of the amino acid residues may be introduced into one region or multiple different regions in the amino acid sequence. The term "one or several amino acid residues" refers to the number of the amino acid residues which do not greatly impair an activity of the protein. In the proteins (C) and (F), the term "one or several" can indicate, for example 1 to 120, 1 to 110, 1 to 100, 1 to 90, 1 to 80, 1 to 75, 1 to 70, 1 to 60, 1 to 50, 1 to 40, 1 to 30, 1 to 25, 1 to 20, 1 to 10 or 1 to 5 (e.g., 1, 2, 3, 4 or 5). In the protein (F1), the term "one or several" can indicate, for example 1 to 25, 1 to 20, 1 to 10 or 1 to 5 (e.g., 1, 2, 3, 4 or 5).

A protein of (A) to (F) and (E1) to (F1) has the D-glucuronyl C5-epimerase activity, thereby having a property that it can be excellent in specific production of the heparosan compound having the isomerized hexuronic acid residue. When the activity is measured under certain conditions, the proteins (B) and (C) as well as the proteins (E) and (F) as well as the proteins (E2) and (F1) have the activity which is 60% or more, 70% or more, 75% or more, 80% or more, 85% or more, 90% or more, 94% or more, 96% or more, 98% or more, based on the activity of the protein (A) as well as based on the activity of the protein (D) as well as based on the activity of the protein (E1), or have the activity which is equivalent to or more than those of the protein (A) as well as the protein (D) as well as the protein (E1), respectively. Examples of such certain conditions for measurement include the conditions where 30% cell free extraction solution (supernatant obtained after sonication and centrifugation of microbial cells) of a microorganism which expresses an objective protein is added to a reaction solution (2 mg/mL N-sulfated heparosan, 50 mM MES (pH 7.0), 1 mM calcium chloride) and the mixture is reacted at 37° C. for 30 minutes or 12 hours.

Mutation may be introduced to a part within a catalytic domain and a part other than the catalytic domain of the proteins (B), (C), (E), (F), (E2) and (F1) so long as a target characteristic can be maintained. The position of an amino acid residue to which mutation may be introduced which can maintain the target characteristic is evident to those skilled in the art. Specifically, those skilled in the art can 1) compare the amino acid sequences of a plurality of proteins having a similar kind of characteristic, 2) clarify a relatively conserved region and a relatively non-conserved region, and 3) predict a region which can play an important role for functions and a region which cannot play the important role for the functions from the relatively conserved region and the relatively non-conserved region, respectively, and can thus recognize structural and functional correlation. Consequently, those skilled in the art can determine the position of the amino acid residue to which mutation may be introduced in the amino acid sequence of the protein.

When the amino acid residue is mutated by substitution, the substitution of the amino acid residue may be conservative substitution. As used herein, the term "conservative substitution" refers to substituting a certain amino acid residue with an amino acid residue having a similar side chain. Families of the amino acid residue having a similar side chain are well known in the art. Examples of the families include amino acids having a basic side chain (e.g., lysine, arginine, and histidine), amino acids having an acidic side chain (e.g., aspartic acid and glutamic acid), amino acids having a non-charged polar side chain (e.g., asparagine, glutamine, serine, threonine, tyrosine, and cysteine), amino acids having a nonpolar side chain (e.g., glycine, alanine, valine, leucine, isoleucine, proline, phenylalanine, methionine, and tryptophan), amino acids having a β-position branched side chain (e.g., threonine, valine, and isoleucine), amino acids having an aromatic side chain (e.g., tyrosine, phenylalanine, tryptophan, and histidine), amino acids having a hydroxy group (e.g., alcoholic and phenolic)-containing side chain (e.g., serine, threonine, and tyrosine), and amino acids having an sulfur-containing side chain (e.g., cysteine and methionine). The conservative substitution of the amino acid may be a substitution between aspartic acid and glutamic acid, substitution among arginine, lysine, and histidine, substitution between tryptophan and phenylalanine, substitution between phenylalanine and valine, substitution among leucine, isoleucine, and alanine, and substitution between glycine and alanine.

In addition, the protein as described herein may be a fusion protein linked to a heterologous part via a peptide bond. Examples of the heterologous part include peptide components which facilitate the purification of a target protein (e.g., tag parts such as a histidine tag and Strep tag II; proteins such as glutathione-S-transferase, maltose binding proteins and mutants thereof which are used for the purification of target protein), peptide components which improve the solubility of the target protein (e.g., Nus-tag), peptide components working as chaperons (e.g., trigger factors), peptide components having other functions (e.g., a full-length protein or part thereof), and linkers.

Examples of the protein as described herein include a protein derived from zebrafish, a naturally occurring homologue thereof, and an artificially prepared mutant protein. The mutant protein can be obtained by introducing mutation into DNA encoding the target protein and producing the mutant protein using the obtained mutant DNA, for example. Examples of a method for introducing mutation include site-directed mutagenesis and random mutation introduction treatment (e.g., treatment with a mutation agent and ultraviolet irradiation).

In one embodiment, the method as described herein can be carried out using the protein itself. For the protein, natural proteins or recombinant proteins can be used. The recombinant proteins can be obtained, for example, by using a cell-free vector or from the microorganisms producing the protein. The protein can be a non-purified, roughly purified, or purified protein. These proteins may be an immobilized protein which is immobilized to a solid phase in the reaction.

The protein is isolated by a known method and is further purified depending on the circumstances, whereby the target protein is obtained. The microorganisms producing the protein can be a transformed microorganism. When the transformed microorganism is used, the target protein is obtained as an inactive target protein aggregate, that is, a protein inclusion body, which can be activated by an appropriate method. After the activation, the target protein may be obtained by separating and purifying the activated protein by a known method.

A medium for culturing the microorganisms is known; a carbon source, a nitrogen source, a vitamin source, or the like may be added to a nutrient medium such as the LB medium or a minimal medium such as the M9 medium. The transformed microorganism is cultured at usually 16° C. to 42° C., or 25° C. to 37° C. for 5 hours to 168 hours, or 8 hours to 72 hours in accordance with a host. Both shaking culture and stationary culture can be performed depending on the host; stirring and ventilation may be performed as needed. When an actinomycete is used as an expression host, conditions which can be used for producing the target protein can be used as appropriate. When an inducible promoter is used for the expression of the target protein, culture can also be performed with a promoter inducer added to the medium.

The produced target protein can be purified and isolated from an extract of the transformed microorganism by known salting-out, sedimentation such as isoelectric sedimentation and solvent sedimentation, methods using difference in molecular weight such as dialysis, ultrafiltration, and gel filtration, methods using specific affinity such as ion-exchange chromatography, methods using difference in the degree of hydrophobicity such as hydrophobic chromatography and reversed phase chromatography, affinity chromatography, SDS polyacrylamide electrophoresis, isoelectric focusing, or combinations thereof. When the target protein is expressed and secreted, bacteria are removed from a culture solution obtained by culturing the transformed microorganism by centrifugation or the like to obtain a culture supernatant containing the target protein. The target protein can be purified and isolated also from this culture supernatant.

After the end of the culture of the transformed microorganism, the bacteria collected by centrifugation are suspended in a bacteria crushing buffer (20 mM to 100 mM of Tris-HCl (pH 8.0) and 5 mM of EDTA), and ultrasonic crushing is performed for about 10 minutes, whereby the bacteria can be crushed, for example. The bacteria crushing can also be performed with a solvent such as toluene added to the culture solution. This crushing treatment solution is centrifuged at 12,000 rpm for 10 minutes, whereby the purification operation described above can be performed on the supernatant. The sediment after the centrifugation can be solubilized with guanidinium chloride, urea, or the like to be further purified as needed. When the target protein is expressed and secreted, after the end of the culture of the transformed microorganism, the culture solution is centrifuged at 12,000 rpm for 10 minutes, whereby the purification operation described above can be performed on the supernatant.

Specifically, the purification of the target protein can be performed as follows, for example. After the end of the culture of the host, ammonium sulfate (2.8 M) is added to the culture supernatant or a cell extract to perform sedimentation fractionation, and operation such as CM Sephadex C-50 or DEAE-Sephadex A-50 ion-exchange column chromatography or Octyl-Sepharose CL-4B or Phenyl-Sepharose CL-4B column chromatography is further performed, whereby the target protein can be purified to the extent that a single band is shown on a gel when polyacrylamide gel electrophoresis is performed thereon.

The activity of the resulting objective protein can be evaluated by measuring the D-glucuronyl C5-epimerase activity (e.g., see Example).

In another embodiment, the method as described herein can be carried out in the presence of a transformed microorganism which produces the protein as described herein or an extract thereof.

For the extract of the microorganisms producing the protein as described herein, a treatment solution containing the target protein and treated by any method can be used. Examples of the treatment include the methods referred to in the isolation and purification described above and a microbicidal treatment method which enables the killing of microorganisms. For the microbicidal treatment method, any method which enables the killing of microorganisms can be used; examples thereof include heat treatment, acid treatment, alkaline treatment, surfactant treatment, and organic solvent treatment.

The transformed microorganism is a host cell that includes an expression unit that includes a polynucleotide as follows [(a) to (j)] and a promoter operably linked thereto: (a) a polynucleotide including the nucleotide sequence of SEQ ID NO:1; (b) a polynucleotide which includes a nucleotide sequence having 80% or more homology to the nucleotide sequence of SEQ ID NO:1 and encodes a protein having a D-glucuronyl C5-epimerase activity; (c) a polynucleotide which hybridizes with a polynucleotide consisting of the nucleotide sequence complementary to the nucleotide sequence of SEQ ID NO:1 under the stringent conditions and encodes a protein having a D-glucuronyl C5-epimerase activity; (d) a polynucleotide including the nucleotide sequence of SEQ ID NO:3; (e) a polynucleotide which includes a nucleotide sequence having 80% or more homology to the nucleotide sequence of SEQ ID NO:3 and encodes a protein having a D-glucuronyl C5-epimerase activity; (f) a polynucleotide which hybridizes with a polynucleotide consisting of the nucleotide sequence complementary to the nucleotide sequence of SEQ ID NO:3 under the stringent conditions and encodes a protein having a D-glucuronyl C5-epimerase activity; (g) a polynucleotide including the nucleotide sequence of SEQ ID NO:4; (h) a polynucleotide which includes a nucleotide sequence having 80% or more homology to the nucleotide sequence of SEQ ID NO:4 and encodes a protein having a D-glucuronyl C5-epimerase activity; (i) a polynucleotide which hybridizes with a polynucleotide consisting of the nucleotide sequence complementary to the nucleotide sequence of SEQ ID NO:4 under the stringent conditions and encodes a protein having a D-glucuronyl C5-epimerase activity; and (j) a degenerate mutant of a polynucleotide of any of the above (a) to (i).

The polynucleotide may be one of the following (e1) to (j1): (e1) a polynucleotide including a nucleotide sequence of SEQ ID NOS:55, 58, 61, 64 or 67; (e2) a polynucleotide which includes a nucleotide sequence having 95% or more homology to a nucleotide sequence of SEQ ID NOS:58, 61, 64 or 67 and encodes a protein having a D-glucuronyl C5-epimerase activity; and (j1) a degenerate mutant of either of the polynucleotide (e1) or (e2).

The above polynucleotides (a) to (j) and (e1) to (j1) may be DNA or RNA, and can be DNA. The nucleotide sequence of SEQ ID NO:1 encodes the amino acid sequence of SEQ ID NO:2. The nucleotide sequences of SEQ ID NOS:3 and 4 encode the amino acid sequence of SEQ ID NO:5. The nucleotide sequence of SEQ ID NO:1 is the naturally occurring full-length nucleotide sequence encoding D-glucuronyl C5-epimerase derived from zebrafish (GenBank: AY388517.1). SEQ ID NO:3 is a partial sequence of the nucleotide sequence of SEQ ID NO:1 and corresponds to the sequence from Gly70 to Asn585. The nucleotide sequence of SEQ ID NO:4 is a degenerate mutant of the nucleotide sequence of SEQ ID NO:3. The nucleotide sequences of SEQ ID NOS:55, 58, 61, 64 and 67 encode the amino acid sequences of SEQ ID NOS:56, 59, 62, 65 and 68, respectively.

In the above polynucleotide (b), (e) or (h), homology % of the nucleotide sequence to the nucleotide sequence of SEQ ID NO:1, 3 or 4 may be 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more. In the above polynucleotide (e2), the homology % to the nucleotide sequence of SEQ ID NOS:58, 61, 64 or 67 may be 95% or more, 96% or more, 97% or more, 98% or more, 99% or more, or 99.5% or more.

The term "stringent conditions" in polynucleotide (c), (f) or (i) refers to conditions in which what is called a specific hybrid is formed, whereas a non-specific hybrid is not formed. Examples of the stringent conditions include hybridization at about 45° C. in 6×SSC (sodium chloride/sodium citrate) followed by washing once or twice or more at 50° C. to 65° C. in 0.2×SSC and 0.1% SDS.

In polynucleotide (j) and (j1), the term "degenerate variant" refers to a polynucleotide mutant in which at least one codon encoding a certain amino acid residue in a polynucleotide before being varied has been changed into another codon encoding the same amino acid residue. This degenerate variant is a mutant based on silent mutation, and a protein encoded by the degenerate variant is the same as a protein encoded by the polynucleotide before being varied.

The degenerate variant can be a polynucleotide mutant in which the codon has been changed so as to be adapted to the codon usage frequency of a host cell to which the degenerate variant is to be introduced. When a gene is expressed by a heterologous host cell (e.g., microorganisms), due to difference in codon usage frequency, a corresponding tRNA molecular species is not sufficiently supplied, which may cause a reduction in translation efficiency and/or incorrect translation (e.g., the stop of translation). In *Escherichia coli*, for example, low frequency codons listed in Table 1 are known.

TABLE 1

Low frequency codons in *Escherichia coli*

| Amino acid residue | Codon | low frequency codons |
|---|---|---|
| Arg | AGG/AGA/CGG/CGA/CGU/CGC | AGG/AGA/CGG/CGA |
| Gly | GGG/GGA/GGU/GGC | GGA |
| Ile | AUA/AUU/AUC | AUA |
| Leu | UUG/UUA/CUG/CUA/CUU/CUC | CUA |
| Pro | CCG/CCA/CCU/CCC | CCC |

Given these circumstances, the degenerate variant can be adapted to the codon usage frequency of a host cell (e.g., microorganisms) described below. In the degenerate variant as described herein, for example, a codon encoding one or more of an arginine residue, a glycine residue, an isoleucine residue, a leucine residue, and a proline residue may be changed. More specifically, in the degenerate variant, one or more of the low frequency codons (e.g., AGG, AGA, CGG, CGA, GGA, AUA, CUA, and CCC) may be changed. The degenerate variant may contain changes of one or more, e.g., one, two, three, four, or five, of the following codons: i) A change of at least one of the codons AGG, AGA, CGG, and CGA encoding Arg into another of the codons CGU or CGC encoding Arg; ii) A change of one codon GGA encoding Gly into another codon GGG, GGU, or GGC; iii) A change of one codon AUA encoding Ile into another codon AUU or AUC; iv) A change of one codon CUA encoding Leu into another codon UUG, UUA, CUG, CUU, or CUC; and v) A change of one codon CCC encoding Pro into another codon CCG, CCA, or CCU.

When the degenerate variant is RNA, the nucleotide residue "U" should be used as described above, whereas when the degenerate variant is DNA, "T" should be used in place of the nucleotide residue "U." The mutation number of nucleotide residues for being adapted to the codon usage frequency of the host cell, which is not limited to a particular number so long as the same protein is encoded before and after mutation, is, for example, 1 to 400, 1 to 300, 1 to 200, or 1 to 100.

The low frequency codon can be easily identified based on the type and genome sequence information of any host cell by using techniques known in the art. Consequently, the degenerate variant may contain a change of a low frequency codon into a non-low frequency codon (e.g., a high frequency codon). Methods for designing mutants considering factors which are not only the low frequency codon but also adaptability to the genome GC content of a producing strain is known (Alan Villalobos et al., Gene Designer: a synthetic biology tool for constructing artificial DNA segments, BMC Bioinformatics. 2006 Jun. 6; 7: 285.); such a method may be used. Thus, the mutant described above can be prepared as appropriate in accordance with the type of the chosen host cell, for example, microorganisms described herein, to which the mutant can be introduced.

The term "expression unit" refers to a minimum unit which contains a certain polynucleotide to be expressed as a protein and a promoter operably linked thereto and enables the transcription of the polynucleotide and eventually the production of a protein encoded by the polynucleotide. The expression unit may further contain elements such as a terminator, a ribosome binding site, and a drug-resistant gene. The expression unit may be DNA or RNA and is DNA is a particular example.

The expression unit may be homologous or heterologous relative to the host cell and is can be a heterologous expression unit. The term "heterologous expression unit" means that the expression unit is heterologous relative to the host cell. Consequently, at least one element contained in the expression unit is heterologous relative to the host cell. Examples of the element contained in the expression cell heterologous relative to the host cell include the elements described above. Either one or both of the polynucleotide encoding the target protein and the promoter contained in the heterologous expression unit can be heterologous relative to the host cell. Consequently, either one or both of the polynucleotide encoding the target protein and the promoter are derived from a living body other than the host cell, for example, a prokaryote or a eukaryote, a microorganism, an insect, a plant, or an animal such as a mammal; or a virus or are artificially synthesized. Alternatively, the polynucleotide encoding the target protein may be heterologous relative to the host cell. The target protein is can be heterologous relative to the host cell.

The promoter contained in the heterologous expression unit is not limited to a particular promoter so long as it can express the protein encoded by the polynucleotide linked to its downstream in the host cell. The promoter may be homologous or heterologous relative to the host cell, for example. Constitutive or inducible promoters generally used for the production of recombinant proteins can be used, for example. Examples of such a promoter include the PhoA promoter, the PhoC promoter, the T7 promoter, the T5 promoter, the T3 promoter, the lac promoter, the trp promoter, the trc promoter, the tac promoter, the PR promoter, the PL promoter, the SP6 promoter, arabinose-inducible promoters, cold shock promoters, and tetracycline-inducible promoters. A promoter having strong transcription activity in the host cell can be used. Examples of the promoter having strong transcription activity in the host cell include promoters of genes highly expressed in the host cell and promoters derived from viruses.

Examples of the host cell used as the transformed microorganism include various kinds of microorganisms including a bacterium belonging to genus *Escherichia* (e.g., *E. coli*), actinomycetes, and coryneform bacteria. *E. coli* used as the host cell includes strains often used generally for cloning and the expression of heterologous proteins such as HB101, MC1061, JM109, CJ236, and MV1184. The actinomycete used as the host cell includes strains often used generally for the expression of heterologous proteins such as *S. lividans* TK24 and coelicolor A3(2). The coryneform bacterium used as the host cell is an aerobic gram-positive bacillus, which includes bacteria currently consolidated into the genus *Corynebacterium*, although having been conventionally classified into the genus *Brevibacterium* (Int. J. Syst. Bacteriol., 41, 255 (1981)) and also includes bacteria belonging to the genus *Brevibacterium*, which is extremely closely related to the genus *Corynebacterium*. The advantages of using a coryneform bacterium include the capability of simplifying and omitting its purification process when the target protein is produced and secreted because of intrinsically secreting a much smaller amount of the protein extracellularly than mold, yeast, and bacteria belonging to the genus *Bacillus*, which have been considered to be suitable for protein secretion; the capability of reducing impurities and side reactions caused by bacterial components, impure enzymes, and the like because a culture supernatant can be used as an enzyme source when an enzyme reaction is carried out using a produced and secreted enzyme; and being excellent in the cost of the medium, the method of culture, and culture productivity because of its easy growing in a simple medium containing sugars, ammonia, inorganic salts, or the like. Using the Tat-system secretion pathway, industrially useful proteins such as Isomaltodextranase and Protein glutaminase, which are proteins difficult to be produced and secreted by the previously known Sec-system secretion pathway, can also be efficiently secreted (WO 2005/103278). Alternatively, disclosed in WO 01/23491, WO 02/081694, WO 01/23491 and the like can be also used.

The transformed microorganism can be prepared by any method known in the art. Such an expression unit is contained in the host cell in the form of being incorporated into the genome DNA of the host cell or the form of being not incorporated into the genome DNA of the host cell (e.g., the form of an expression vector), for example. The host cell including the expression unit can be obtained by transforming the host cell by the expression vector by any method known in the art (e.g., a competent cell method and an electroporation method). When the expression vector is an integrative vector which causes homologous recombination with the genome DNA of the host cell, the expression unit can be incorporated into the genome DNA of the host cell by transformation. In contrast, when the expression vector is a non-integrative vector which does not cause homologous recombination with the genome DNA of the host cell, the expression vector is not incorporated into the genome DNA of the host cell by transformation and can remain as the expression vector to be present independently of the genome DNA. Alternatively, the expression unit can be incorporated into the genome DNA of the host cell by a genome editing technique (e.g., the CRISPR/Cas system and Transcription Activator-Like Effector Nucleases (TALEN)).

The expression vector may further contain elements such as a terminator functioning in the host cell, a ribosome binding site, and a drug-resistant gene in addition to the minimum unit described above as the expression unit. Examples of the drug-resistant gene include resistant genes against drugs such as tetracycline, ampicillin, kanamycin, hygromycin, and phosphinothricin.

The expression vector may further contain a region which enables homologous recombination with the genome of the host cell for the homologous recombination with the genome DNA of the host cell. The expression vector may be designed such that the expression unit contained therein is positioned between a pair of homologous regions (e.g., a homology arm loxP and FRT homologous to a specific sequence in the genome of the host cell), for example. The genome region (the target of the homologous region) of the host cell to which the expression unit is to be introduced, which is not limited to a particular region, may be a locus of a gene having a large amount of expression in the host cell.

The expression vector may be a plasmid, a virus vector, a phage, or an artificial chromosome. The expression vector may be an integrative vector or a non-integrative vector. The integrative vector may be a vector of a type the entire of which is incorporated into the genome of the host cell. Alternatively, the expression vector may be a vector of a type only part of which (e.g., the expression unit) is incorporated into the genome of the host cell. Furthermore, the expression vector may be a DNA vector or an RNA vector (e.g., a retrovirus). For the expression vector, generally used expression vectors may be used. Examples of such expression vectors include pUC (e.g., pUC19 and pUC18), pSTV, pBR (e.g., pBR322), pHSG (e.g., pHSG299, pHSG298, pHSG399, and pHSG398), RSF (e.g., RSF1010), pACYC (e.g., pACYC177 and pACYC184), pMW (e.g., pMW119, pMW118, pMW219, and pMW218), pQE (e.g., pQE30), and derivatives thereof. When a coryneform bacterium such as *Corynebacterium glutamicum* is selected as the host cell, pPK4 as a high copy vector or the like can be suitably used.

As described above, the method of the present invention can be carried out in a reaction system including the amino acid or a salt thereof and the carboxylic acid or a salt thereof in the presence of the protein itself and/or the microorganisms producing the protein or a treatment solution thereof.

A method for producing a heparan sulfate is also described herein. The method as described herein includes generating heparan sulfate by subjecting a heparosan to the C5-epimerization of a hexuronic acid residue, the 2-O-sulfation of a hexuronic acid residue, the N-sulfation of an α-D-glucosamine residue, the 3-O-sulfation of an α-D-glucosamine residue, and the 6-O-sulfation of an α-D-glucosamine residue.

In the method for producing a heparan sulfate, the C5-epimerization can be performed by the method as described above.

In the method for producing a heparan sulfate, the N-deacetylation of the heparosan compound, the 2-O-sulfation of the hexuronic acid residue, the N-sulfation of the α-D-glucosamine residue, the 3-O-sulfation of the α-D-glucosamine residue, and the 6-O-sulfation of the α-D-glucosamine residue can be performed by methods well-known in the art (e.g., U.S. Pat. No. 8,227,449; US Patent Application Publication No. 2012-322114; Lindahl U. et al. (2005) J. Med. Chem., 48(2): 349-352; Zhang Z. et al. (2008) Journal of the American Chemical Society, 130(39): 12998-13007; Chen J, et al., J. Biol. Chem., 2005 Dec. 30; 280(52): 42817-25). The order of performing these treatments is not particularly limited as long as heparan sulfate is obtained. The order of performing respective treatments can be appropriately set depending on various conditions such as procedures for performing each treatment and substrate specificities of enzymes used for each treatment. The above treatments may be performed simultaneously or separately.

Examples of the representative order of performing the above treatments include the following order:

1. N-deacetylation of a heparosan compound;
2. N-sulfation of an α-D-glucosamine residue;
3. C5-epimerization of a hexuronic acid residue; and
4. 2-O-sulfation of the hexuronic acid residue, 3-O-sulfation of the α-D-glucosamine residue, and 6-O-sulfation of the α-D-glucosamine residue.

Two or more treatments can be also performed in parallel.

The 2-O-sulfation of the hexuronic acid, the 3-O-sulfation of the α-D-glucosamine residue, and the 6-O-sulfation of the α-D-glucosamine residue may be performed in any order. Examples of a representative order include the order of the 2-O-sulfation of the hexuronic acid, the 3-O-sulfation of the α-D-glucosamine residue, and the 6-O-sulfation of the α-D-glucosamine residue as well as the order of the 2-O-sulfation of the hexuronic acid, the 6-O-sulfation of the α-D-glucosamine residue, and the 3-O-sulfation of the α-D-glucosamine residue. Two or more treatments can be also performed in parallel.

The N-deacetylation can be performed chemically using a deacetylation agent. Examples of N-deacetylation agent include basic substances such as alkaline metal salts, alkaline earth metal salts and hydrazine. Examples of alkaline metal salts include sodium hydroxide, potassium hydroxide, lithium hydroxide, rubidium hydroxide and cesium hydroxide. Examples of alkali earth metal salts include beryllium hydroxide, magnesium hydroxide, calcium hydroxide, strontium hydroxide, and barium hydroxide.

The N-deacetylation can be partial N-deacetylation. The N-deacetylation can be performed so that a residual rate of the N-acetyl group becomes the following value. That is, the residual rate of the N-acetyl group may be, for example, 1% or more, 1.5% or more, 3% or more, 5% or more, 7% or more, 9% or more, or 11% or more, 50% or less, 45% or less, 40% or less, 35% or less, 33% or less, 30% or less, 25% or less, 20% or less, or 17% or less, or a combination thereof. Specifically, the residual rate of the N-acetyl group may be for example, 1% to 33%, 7% to 33%, 7% to 30%, or 11% to 17%. For example, the residual rate of the N-acetyl group of 7% to 30% approximately corresponds to a state where the N-acetyl groups are present at a rate of one N-acetyl group per 6 to 28 sugar residues (one per 3 to 14 units as a disaccharide unit). Also, for example, the residual rate of the N-acetyl group of 11% to 17% approximately corresponds to a state where the N-acetyl groups are present at a rate of one N-acetyl group per 12 to 18 sugar residues (one per 6 to 9 units as a disaccharide unit). A degree of N-deacetylation (i.e., residual rate of the N-acetyl groups) can be confirmed, for example, by the disaccharide analysis. That is, the residual rate of the N-acetyl groups can be calculated as a percentage (molar ratio) of an amount of the disaccharide units having the N-acetylated group relative to a total amount of the disaccharide units when the polysaccharide is subjected to the disaccharide analysis.

As conditions for partial N-deacetylation utilizing sodium hydroxide, for example, the previously reported conditions (Kuberan B. et al., (2003) "Chemoenzymatic Synthesis of Classical and Non-classical Anticoagulant Heparan Sulfate Polysaccharides." J. Biol. Chem., 278 (52): 52613-52621. and US2011281820A1) can be referenced. As conditions for partial N-deacetylation utilizing hydrazine, for example, the previously reported conditions (Glycobiology, 10 (2000) 159-171; Carbohydrate Research, 290 (1996) 87-96; Biochem. J. 217 (1984) 187-197) can be referenced.

The 2-O-sulfation is a step of sulfating hydroxy group at position 2 in the hexuronic acid residue in the heparosan compound. The 2-O-sulfation can be performed enzymatically by utilizing a 2-O-sulfation enzyme (2-OST).

The N-sulfation is a step of sulfating an amino group of α-D-glucosamine residue in the heparosan compound. The N-sulfation can be performed chemically using a sulfation reagent. The sulfation reagent includes sulfur trioxide complex such as sulfur trioxide pyridine complex (PySO3) and sulfur trioxide trimethylamine complex ($TMASO_3$).

The 6-O-sulfation is a step of sulfating hydroxy group at position 6 of α-D-glucosamine residue in the heparosan compound. The 6-O-sulfation can be performed enzymatically utilizing, for example, a 6-O-sulfation enzyme (6-OST). Examples of 6-OST include 6-OST-1, 6-OST-2 and 6-OST-3. The 6-O-sulfation can be also performed chemically by utilizing a sulfation reagent. The sulfation reagent includes sulfur trioxide complex such as sulfur trioxide pyridine complex (PySO3) and sulfur trioxide trimethylamine complex ($TMASO_3$).

The 3-O-sulfation is a step of sulfating hydroxy group at position 3 of α-D-glucosamine residue in the heparosan compound. The 3-O-sulfation can be performed enzymatically by utilizing a 3-O-sulfation enzyme (3-OST). Examples of 3-OST include 3-OST-1, 3-OST-2, 3-OST-3, 3-OST-4, and 3-OST-5.

In the method for producing a heparan sulfate, the treatment may further include low-molecularizing the heparosan compound.

The order of the low molecularization is not particularly limited as long as a heparan sulfate is obtained. The order of the low molecularization can be appropriately set depending on various conditions such as procedures for the low molecularization and other treatments and substrate specificities of enzymes used for the treatments. The low molecularization may be performed simultaneously with or separately from the other treatment. Representatively, the low molecularization may be performed after the N-deacetylation of the heparosan compound and before the N-sulfation of the α-D-glucosamine residue.

The low molecularization can be performed enzymatically using heparinase. Examples of heparinase include heparinase I, heparinase II and heparinase III, and heparinase III is a particular example. The low molecularization is not particularly limited as long as heparosan is treated so that a molecular weight of heparosan after the low molecularization is smaller than that before the low molecularization, and can be performed so that the number average molecular weight (Mn) is 1000 to 150000, or 8000 to 60000 and the weight average molecular weight (Mw) is 2000 to 300000, or 10000 to 100000 as measured by GPC using pullulan as a standard.

The low molecularization is performed using heparinase III. "Heparinase III" refers to an enzyme (typically EC 4.2.2.8) which cleaves a site of N-sulfated or N-deacetylated glucosamine residue of glycosaminoglycan such as heparosan. Heparinase III is not particularly limited as long as it can preferentially cleave a site of a glucosamine residue having an N-acetyl group in N-deacetylated heparosan. "Cleaving preferentially the site of the glucosamine residue having the N-acetyl group" refers to cleaving the site of the glucosamine residue having the N-acetyl group more preferentially than the site of the glucosamine residue having no N-acetyl group. "Cleaving preferentially the site of the glucosamine residue having the N-acetyl group" may mean that the site of the glucosamine residue having the N-acetyl group is cleaved but the site of the glucosamine residue having no N-acetyl group is not substantially cleaved. "Cleaving the site of the glucosamine residue refers to cleaving α-1,4-glycoside linkage between the glucosamine residue and a glucuronic acid (GlcA) residue downstream thereof (on a side of the reduced terminus).

The product by each step contained in the reaction solution of each step may directly be subjected to a subsequent step, or may be recovered from the reaction solution and then subjected to the subsequent step. A procedure for recovering each product from the reaction solution is not particularly limited. The procedure for recovering each product includes known techniques used for the separation and purification of the compound, such as a membrane treatment method and a precipitation method. The product in each step may be appropriately subjected to the treatments such as purification, dilution, concentration, drying, dissolution, and inactivation of the enzyme, and then subjected to the subsequent step. The purification may be performed to the desired extent. These treatments may be performed alone or in combination as appropriate.

A protein is also provided such as the following (E1) to (F1):

(E1) a protein including an amino acid sequence of SEQ ID NOS:56, 59, 62, 65 or 68;

(E2) a protein which includes an amino acid sequence having 95% or more homology to an amino acid sequence of SEQ ID NOS:59, 62, 65 or 68, and has a D-glucuronyl C5-epimerase activity; and (F1) a protein which includes an amino acid sequence having 1 to 25 deleted, substituted, added or inserted amino acid residues in an amino acid sequence of SEQ ID NOS:59, 62, 65 or 68, and has a D-glucuronyl C5-epimerase activity.

The protein can be a variant of D-glucuronyl C5-epimerase derived from zebrafish. The D-glucuronyl C5-epimerase derived from zebrafish has a more excellent D-glucuronyl C5-epimerase activity than D-glucuronyl C5-epimerase derived from other organism species when the activity is measured under certain conditions. Also, the protein has the D-glucuronyl C5-epimerase activity which is equivalent or improved compared with wild type D-glucuronyl C5-epimerase derived from zebrafish when the activity is measured under the certain conditions. For example, the protein has the activity which is equivalent to (100%) or higher, 110% or higher, 120% or higher, 130% or higher, 140% or higher, 150% or higher, 160% or higher, 170% or higher, 180% or higher, 190% or higher, or 200% or higher than the activity of the wild type enzyme. Therefore, the protein has extremely excellent D-glucuronyl C5-epimerase activity. Such certain conditions for measurement include, for example, the conditions where 30% cell free extraction solution (supernatant obtained after sonication and centrifugation of microbial cells) of a microorganism which expresses an objective protein is added to a reaction solution (2 mg/mL N-sulfated heparosan, 50 mM MES (pH 7.0), 1 mM calcium chloride) and the mixture is reacted at 37° C. for 30 minutes or 12 hours.

The protein can be used as an enzyme for performing a C5-epimerization reaction with high efficiency because it has the extremely excellent D-glucuronyl C5-epimerase activity. For example, the protein can be used for performing the C5-epimerization reaction with high efficiency in the production of heparan sulfate such as heparin from heparosan.

The protein may be provided in any structure or form described above as long as it has the D-glucuronyl C5-epimerase activity. That is, the protein may be provided in a structure of a fusion protein linked to the heterogenous portion described above through a peptide bond, or may be provided in a structure of a protein which is not linked to the heterogeneous portion described above. Also, the protein may be provided in a form of an unpurified product, a crude product or a purified protein, or may be provided in a form of a solid-phased protein immobilized to a solid phase, and can be provided in the form of the purified protein. The protein can be prepared from a culture medium, a culture supernatant of a microorganism which expresses the protein, a disrupted product by sonication of microbial cells, and a supernatant obtained after the sonication and centrifugation of the microbial cells (cell free extract).

EXAMPLES

The present invention is explained in more detail with reference to examples, however, the present invention is not limited to the following examples.

Example 1: Preparation of N-Sulfated Low-Molecularized Heparosan (1) Heparosan Fermentation A culture solution containing heparosan was obtained using the heparosan-producing bacterium (*Escherichia coli*

BL21 (DE3)/pVK9-kfiABCD strain) and the culture conditions described in Example 1 of WO2015/050184.

(2) Purification of Heparosan

A culture supernatant was collected from the culture solution by centrifugation. In order to remove medium ingredients, 1 mL of the culture supernatant was washed with Milli-Q water using a UF membrane, and concentrated to 250 μL. To 250 μL of the solution concentrated with the UF membrane, 500 μL of 100% ethanol was added, and heparosan was precipitated by centrifugation. The resulting precipitate was dried in air to obtain heparosan. Also from the remaining culture supernatant, heparosan was purified by the same procedure. Total 10 g of heparosan was obtained.

(3) N-Deacetylation of Heparosan

1) To 1.22 g of the heparosan, 61 mL of hydrazine.$H_2O$ and 4.7 mL of 1 N sulfuric acid were added, and after replacing the gas phase with nitrogen, the mixture was heated to 100° C. and reacted for 4.75 hours.

2) After stopping the reaction by ice cooling, 61 mL of 16% NaCl aqueous solution and 610 mL of MeOH were added and the mixture was centrifuged. The supernatant was removed. The resulting precipitate was dissolved in 50 mL of $H_2O$, and was then desalted and concentrated using Amicon UF membrane (3 kDa).

3) To the resulting concentrated solution, the twice volume of $H_2O$ and the equivalent volume of 1 M $NaHCO_3$ were added, and then, 0.2 M $I_2$/0.4 M KI solution was dripped until coloring yellow. Subsequently, hydrazine.$H_2O$ was dripped to reduce the excessive iodine to iodine ion, and then the solution was desalted and concentrated using Amicon UF membrane (3 kDa) again. The concentrated solution was dried under reduced pressure to obtain N-deacetylated heparosan. The residual rate of the acetyl group in the obtained N-deacetylated heparosan was 14.9% (described later).

(4) Low Molecularization of N-Deacetylated Heparosan

1) Preparation of Heparinase III

<Construction of Flavobacterium Heparinum-Derived hepC Gene Expression Plasmid>

The hepC gene encoding heparinase III derived from *Flavobacterium heparinum* was cloned into a pMIV-Pnlp0 vector (US Patent Application publication 20050196846) to construct the hepC gene expression plasmid pMIV-Pnlp0-hepC. The pMIV-Pnlp0-ter includes a potent nlp0 promoter (Pnlp0) and an rrnB terminator, and can function as an expression unit by inserting an objective gene between the promoter and the terminator. "Pnlp0" represents a promoter for the wild type nlpD gene derived from *Escherichia coli* K-12.

Details for the construction of the expression plasmid is shown below. A DNA fragment including about 300 bp of a promoter region (Pnlp0) for the nlpD gene was obtained by PCR with chromosomal DNA from *Escherichia coli* MG1655 as a template using primer P1 (SEQ ID NO:22) and primer P2 (SEQ ID NO:23). Sites for restriction enzymes SalI and PaeI have been designed in each 5'-terminus of these primers. PCR cycles were as follows. First, 95° C. for 3 minutes, then two cycles of 95° C. for 60 seconds, 50° C. for 30 seconds and 72° C. for 40 seconds, subsequently 25 cycles of 94° C. for 20 seconds, 55° C. for 20 seconds and 72° C. for 15 seconds, and finally 72° C. for 5 minutes. A resulting fragment was treated with SalI and PaeI, and inserted into the SalI-PaeI site of pMIV-5JS (Japanese Patent Application Publication No. 2008-099668) to obtain plasmid pMIV-Pnlp0. The nucleotide sequence of the PaeI-SalI fragment of the Pnlp0 promoter inserted into this pMIV-Pnlp0 plasmid is as shown in SEQ ID NO:24.

Subsequently, the DNA fragment (SEQ ID NO:27) including about 300 bp of a terminator region of the rrnB gene was obtained by PCR with chromosomal DNA from MG1655 as a template using primer P3 (SEQID NO:25) and primer P4 (SEQ ID NO:26. Sites of restriction enzymes XbaI and BamHI have been designed at each 5'-terminus of these primers. The PCR cycles were as follows. First, 95° C. for 3 minutes, then two cycles of 95° C. for 60 seconds, 50° C. for 30 seconds and 72° C. for 40 seconds, subsequently 25 cycles of 94° C. for 20 seconds, 59° C. for 20 seconds and 72° C. for 15 seconds, and finally 72° C. for 5 minutes. A resulting fragment was treated with XbaI and BamHI, and inserted into the XbaI-BamHI site of pMIV-Pnlp0 to obtain plasmid pMIV-Pnlp0-ter.

Subsequently, a DNA chain including the ORF of the hepC gene derived from Flavobacterium heparinum (ATCC 13125) (Su H. et. al., Appl. Environ. Microbiol., 1996, 62: 2723-2734) was artificially synthesized. A DNA fragment of the hepC gene was amplified by PCR with this DNA chain as a template using primer P5 (SEQ ID NO:28) and primer P6 (SEQ ID NO:29). The PCR was performed using PrimeStar polymerase (TaKaRa) in the reaction composition described in the protocol. The PCR cycle was as follows. First, 94° C. for 5 minutes, then 30 cycles of 98° C. for 5 seconds, 55° C. for 10 seconds and 72° C. for 8 minutes, and finally keeping at 4° C. Also, a DNA fragment of pMIV-Pnlp0 was obtained by PCR with pMIV-Pnlp0 as a template DNA using oligonucleotides of a primer 7 (SEQ ID NO:30) and a primer 8 (SEQ ID NO:31) as primers. PCR was performed using PrimeStar polymerase (TaKaRa) and the reaction composition described in the protocol. The PCR cycle was as follows. First, 94° C. for 5 minutes, then 30 cycles of 98° C. for 5 seconds, 55° C. for 10 seconds and 72° C. for 6 minutes, and finally keeping at 4° C. Both resulting DNA fragments were ligated using In-Fusion (registered trademark) HD cloning kit (Clontech) to construct the hepC gene expression plasmid pMIV-Pnlp0-hepC. A nucleotide sequence of the cloned hepC gene and an amino acid sequence of heparinase III (HepC) encoded thereby are shown in SEQ ID NOS:32 and 33, respectively.

<Construction of *Escherichia coli* BL21 (DE3) Strain Expressing hepC Gene and Preparation of Heparinase III Enzyme Solution>

The hepC gene expression plasmid pMIV-Pnlp0-hepC was introduced into *Escherichia coli* BL21 (DE3) strain (Life Technologies) by electroporation (Cell: 80 μL, 200Ω, 25 μF, 1.8 kV, cuvette: 0.1 mL) to obtain *Escherichia coli* BL21 (DE3)/pMIV-Pnlp0-hepC strain as a heparinase III-producing strain. This strain was pre-cultured in 25 μg/mL chloramphenicol-added LB medium at 37° C. overnight. Subsequently, the culture solution was inoculated to 300 mL LB medium in a Sakaguchi flask at a final concentration of 2% v/v. The cultivation with shaking was performed at 37° C. for 4 hours, and the cultivation was stopped. After centrifugation, the microbial cells were washed twice with 0.85% NaCl, and suspended in 30 mL of 50 mM HEPES buffer (pH 7.0). The suspension was subjected to sonication disruption to disrupt the microbial cells. The disrupted microbial cell solution was centrifuged to prepare a heparinase III enzyme solution as a supernatant (cell free extract solution)

2) Low Molecularization by Heparinase III Reaction

The 1 g of N-deacetylated heparosan with an N-acetyl group residual rate of 14.9% obtained in above (3) and 2 mL of 31.3 mIU/μL heparinase III solution were dissolved in 100 mL of Tris buffer solution (pH 8.0) containing 100 mM NaCl and 1.5 mM $CaCl_2$, and reacted at 37° C. for 5.3 hours. To the reaction solution, 100 mL of 16% NaCl aqueous solution and 900 mL of EtOH were added and mixed and were centrifuged to remove a supernatant and obtain low-molecularized N-deacetylated heparosan. A molecular weight after the low molecularization by heparinase III was measured by GPC using pullulan as the standard. As a result, the number average molecular weight (Mn) and the weight average molecular weight (Mw) were 9860 and 15430, respectively.

(5) N-Sulfation of Low-Molecularized N-Deacetylated Heparosan

1) The 1 g of the low-molecularized N-deacetylated heparosan obtained in above (4) was dissolved in 50 mL of MilliQ water, and 50 mL of an aqueous solution of 20 mg/mL $NaHCO_3$/20 mg/mL trimethylamine.$SO_3$ was added thereto, and the mixture was reacted at 55° C. overnight.

2) To the mixture, 1 L of EtOH was added, which was then centrifuged to remove a supernatant to obtain N-sulfated low-molecularized heparosan.

3) The obtained N-sulfated low-molecularized heparosan was dissolved in MilliQ water up to 500 µL, and the disaccharide analysis was performed to calculate a yield relative to N-deacetylated heparosan. The procedures are shown below.

<Disaccharide Analysis>

The disaccharide analysis of N-sulfated low-molecularized heparosan was performed according to the conditions previously reported (T. Imanari, et. al., "High-performance liquid chromatographic analysis of glycosaminoglycan-derived oligosaccharides." J. O. Chromato. A, 720, 275-293 (1996)). That is, an amount of each constituent disaccharide was quantified by decomposing N-sulfated low-molecularized heparosan into unsaturated disaccharides using heparinases II and III and analyzing each decomposed product by HPLC.

Likewise, the disaccharide analysis of N-deacetylated heparosan was performed. The disaccharide analysis of N-deacetylated heparosan was performed after N-deacetylated heparosan was N-sulfated. That is, the amount of each constituent disaccharide was quantified by N-sulfating N-deacetylated heparosan, subsequently decomposing it into unsaturated disaccharides using heparinases II and III, and analyzing each decomposed product by HPLC. The N-sulfation of N-deacetylated heparosan was performed as was the case with the N-sulfation of low-molecularized N-deacetylated heparosan.

The disaccharide analysis was specifically performed by the following procedure.

1) The 0.2 U of heparinase II (Sigma), 0.02 to 0.03 mIU of heparinase III, 5 µg of a polysaccharide sample, and 10 µL of buffer for enzymatic digestion (100 mM $CH_3COONa$, 10 mM $(CH_3COO)_2Ca$, pH 7.0) were mixed and diluted with Milli-Q water up to 100 µL of measured volume to use as a reaction solution.

2) The reaction solution was reacted at 37° C. for 16 hours or longer, and subsequently boiled at 100° C. for 2 minutes to stop the reaction.

3) Impurities were removed through 0.45 µm filter to obtain a solution, which was then used as a sample for the disaccharide analysis.

4) The analysis was performed using a column of Inertsil ODS-3 150 mm×2.1 mm with 5 µm particle size under the conditions of temperature at 50° C., a flow date of 0.25 mL/min and a detection wavelength of 230 nm, and using an eluent composition of 4% acetonitrile and 1.2 mM tributylamine as solution A and 4% acetonitrile and 0.1 M CsCl as solution B with a gradient from 1 to 90% of solution B.

The yield was calculated from the sum of the amounts of constituent disaccharides produced from each polysaccharide sample. That is, the yield was calculated as a percentage (molar ratio) of a total amount of disaccharides produced from N-sulfated low-molecularized heparosan relative to a total amount of disaccharides produced from N-deacetylated heparosan. Also, at that time, it was confirmed that 99% or more of amino groups produced by N-acetylation was N-sulfated in the obtained N-sulfated low-molecularized heparosan.

Also, the residual rate of the N-acetyl groups in N-deacetylated heparosan was calculated based on the amount of each constituent disaccharide produced from N-deacetylated heparosan. That is, the residual rate of the acetyl group was calculated as a percentage (molar ratio) of the amount of disaccharides having the acetyl group relative to the total amount of disaccharides. The residual rate of the acetyl groups was 14.9%.

Example 2: Construction of Bacterial Strain Expressing D-Glucuronyl C5-Epimerase (Dlce)

(1) Construction of Bacterial Strain Expressing D-Glucuronyl C5-Epimerase Derived from Human (hspDlce)

The C-terminal region DNA fragment of the mutant maltose binding protein (MBP*) was obtained by PCR with pMAL-c2x (SEQ ID NO:2, New England BioLabs) as a template DNA using SEQ ID NO:34 and SEQ ID NO:35 as primers. In the above PCR, the recognition site for a restriction enzyme BglII was added to the 5'-terminus, and the restriction sites for the restriction enzymes HindIII, BamHI, Sad, XhoI and NotI were added to the 3'-terminus. The pMAL-c2x plasmid DNA and the C-terminal region DNA fragment of MBP* were cleaved with BglII and HindIII and ligated to yield pMAL-MBP* plasmid. The nucleotide sequence of pMAL-MBP* plasmid is shown in SEQ ID NO:21.

A cDNA encoding the full-length protein of D-glucuronyl C5-epimerase derived from human was prepared by artificial gene synthesis (Thermo Fisher Scientific). PCR amplification with 30 cycles of 5 seconds at 98° C., 10 seconds at 55° C. and 2 minutes at 72° C. was performed using this cDNA as a template and PrimeStar polymerase (TaKaRa) as polymerase according to the protocol to yield a DNA fragment including a nucleotide sequence encoding the catalytic site (Gly101 to Asn617) of the D-glucuronyl C5-epimerase derived from human. The combination of SEQ ID NOS:36 and 37 was used as primers. The resulting DNA fragment was digested with NotI and XhoI, and ligated to the pMAL-MBP* plasmid previously digested with NotI and XhoI by a ligation reaction. *Escherichia coli* JM109 strain was transformed with this reaction solution, then applied onto LB agar medium containing 100 µg/mL of ampicillin, and cultured at 30° C. overnight. A plasmid was extracted from a colony of growing transformed microorganisms according to the known method, its nucleotide sequence was confirmed using 3100 Genetic Analyzer (Applied Biosystems), and a plasmid having an objective structure was designated as pMAL-MBP*-hspDlce (G101). *Escherichia coli* Origami B (DE3) was transformed with resulting pMAL-MBP*-hspDlce (G101), then applied onto LB agar medium containing 100 µg/mL of ampicillin, and a transformed microorganism having the objective plasmid was obtained. This transformed microorganism was designated as *Escherichia*

*coli* Origami B (DE3)/pMAL-MBP*-hspDlce (G101), and used as a hspDlce-expressing strain. The nucleotide sequence of the inserted fragment and the amino acid sequence encoded thereby are shown in SEQ ID NO:6 and SEQ ID NO:7, respectively.

(2) Construction Bacterial Strain Expressing D-glucuronyl C5-epimerase Derived from other Organism Species PCR amplification with 30 cycles of 5 seconds at 98° C., 10 seconds at 55° C. and 2 minutes at 72° C. was performed using pMAL-MBP* as template DNA and PrimeStar polymerase (TaKaRa) as polymerase according to the protocol of the manufacturer to yield a DNA fragment of pMAL-MBP*. The combination of SEQ ID NOS:38 and 39 was used as primers.

cDNAs encoding the full-length proteins of D-Glucuronyl C5-epimerase derived from opossum, D-glucuronyl C5-epimerase derived from chicken, D-glucuronyl C5-epimerase derived from frog, D-glucuronyl C5-epimerase derived from zebrafish, D-glucuronyl C5-epimerase derived from sea squirt, and D-glucuronyl C5-epimerase derived from *Drosophila* and D-glucuronyl C5-epimerase derived from *C. elegans* were prepared by the artificial gene synthesis (Thermo Fisher Scientific). DNA fragments including a nucleotide sequence encoding the catalytic site of D-glucuronyl C5-epimerase (Gly100 to Asn617) derived from opossum, the catalytic site of D-glucuronyl C5-epimerase (Gly88 to Asn605) derived from chicken, the catalytic site of D-glucuronyl C5-epimerase (Gly92 to Asn607) derived from frog, the catalytic site of D-glucuronyl C5-epimerase (Gly70 to Asn585) derived from zebrafish, the catalytic site of D-glucuronyl C5-epimerase (Gly92 to Asn637) derived from sea squirt, the catalytic site of D-glucuronyl C5-epimerase (Y66 to Asn614) derived from *Drosophila*, and full-length D-glucuronyl C5-epimerase derived from *C. elegans* were obtained using these cDNA as a template by the same method as in (1). The combinations of SEQ ID NOS:40 and 41, SEQ ID NOS:42 and 43, SEQ ID NOS:44 and 45, SEQ ID NOS:46 and 47, SEQ ID NOS:48 and 49, SEQ ID NOS:50 and 51, and SEQ ID NOS:52 and 53 were used as primers, respectively. The resulting each DNA fragment and the DNA fragment of pMAL-MBP* were ligated using In-Fusion (registered trademark) HD Cloning Kit (Clontech). *Escherichia coli* JM109 strain was transformed with this ligation solution to yield pMAL-MBP*-mdoDlce (G100), pMAL-MBP*-ggaDlce (G88), pMAL-MBP*-xtrDlce (G92), pMAL-MBP*-dreDlce (G70), pMAL-MBP*-cinDlce (K92), pMAL-MBP*-dmeDlce (Y66), and pMAL-MBP*-celDlce by the same method as in (1). *Escherichia coli* Origami B(DE3) was each transformed with the resulting plasmid. The resulting bacterial strains were designated as *Escherichia coli* Origami B(DE3)/pMAL-MBP*-mdoDlce (G100), *Escherichia coli* Origami B(DE3)/pMAL-MBP*-ggaDlce (G88), *Escherichia coli* Origami B(DE3)/pMAL-MBP*-xtrDlce (G92), *Escherichia coli* Origami B(DE3)/pMAL-MBP*-dreDlce (G70), *Escherichia coli* Origami B(DE3)/pMAL-MBP*-cinDlce (K92), *Escherichia coli* Origami B(DE3)/pMAL-MBP*-dmeDlce(Y66), and *Escherichia coli* Origami B(DE3)/pMAL-MBP*-celDlce, respectively, and used as a bacterial strain expressing Dlce derived from each organism species. Nucleotide sequences of the inserted fragments are each shown in SEQ ID NO:8, 10, 12, 14, 16 and 18, and the amino acid sequences encoded thereby are each shown in SEQ ID NO:9, 11, 13, 15, 17 and 19.

Example 3: Expression of D-Glucuronyl C5-Epimerase (Dlce) Derived from each Organism Species

*Escherichia coli* Origami B(DE3)/pMAL-MBP*-hspDlce (G101), *Escherichia coli* Origami B(DE3)/pMAL-MBP*-mdoDlce (G100), *Escherichia coli* Origami B(DE3)/pMAL-MBP*-ggaDlce (G88), *Escherichia coli* Origami B(DE3)/pMAL-MBP*-xtrDlce (G92), *Escherichia coli* Origami B(DE3)/pMAL-MBP*-dreDlce (G70), *Escherichia coli* Origami B(DE3)/pMAL-MBP*-cinDlce (K92), *Escherichia coli* Origami B(DE3)/pMAL-MBP*-dmeDlce (Y66), and *Escherichia coli* Origami B(DE3)/pMAL-MBP*-celDlce were each inoculated to the LB medium (1.0% (w/v) peptone, 0.5% (w/v) yeast extract, 1.0% (w/v) NaCl) containing 100 μg/mL of ampicillin, and precultured at 37° C. overnight. Subsequently, the resulting cultured medium was inoculated at a final concentration of 1% to 3 mL of the LB medium, and cultured at 37° C. with shaking for 3 hours. Then, isopropyl-β-D-thiogalactopyranoside (IPTG) (Nacalai Tesque) was added at a final concentration of 0.5 mM thereto, and the culture was continued at 22° C. overnight to express Dlce derived from each organism species in the microbial cells.

The cultured medium was centrifuged, the microbial cells were collected, washed once with a washing solution (20 mM Tris-HCl, pH 7.5, 200 mM NaCl), and resuspended in the washing solution in an amount which is 1/10 of the cultured medium. Then, the microbial cells were disrupted by sonication using Bioraptor (Sonic Bio) and centrifuged at 14,000 rpm for 20 minutes. The resulting supernatant was used as a cell-free extract containing Dlce derived from each organism species.

Example 4: C5-Epimerization Reaction by Cell-Free Extract Containing Dlce Derived from each Organism Species (1) C5-Epimerization Reaction The cell-free extract containing Dlce derived from each organism species at a concentration of 30% was added to a reaction solution (2 mg/mL N-sulfated low-molecularized heparosan, 50 mM MES, pH 7.0, 1 mM calcium chloride), and the mixture was reacted at 37° C. for 30 minutes or 12 hours. As a negative control, the enzymatic reaction was performed under the conditions where the washing solution in place of the cell-free extract was added to the reaction solution.

(2) Quantification of C5-Epimarization Ratio

A C5-epimerization ratio was quantified by disaccharide composition analysis using nitrous acid degradation.

<Reagents>

$NaNO_2$ (CAS No. 7632-00-0, MW: 69.01)

Citric acid (CAS No. 77-92-9, MW: 192.1)

2,4-dinitrophenylhydradine (CAS No. 119-26-6, MW: 198.1), 50% aqueous product (abbreviated: DNPH)

<Test Solution>

$NaNO_2$ aqueous solution: 49.5 mg of the reagent was dissolved in 0.1 mL of $H_2O$.

Citric acid aqueous solution: 384.2 mg of the reagent was dissolved in 0.1 mL of $H_2O$.

<Analysis Procedure>

To a 1.5 mL microtube (Eppendorf), 10 μL of the reaction solution, 20 μL of citrate buffer, and 10 μL of the $NaNO_2$ aqueous solution were added in this order, and the mixed solution was stirred (1000 rpm) at 65° C. for 2 hours to yield a nitrous acid degradation solution. Then, 20 μL of a DNPH solution was added to 40 μL of the resulting nitrous acid degradation solution, and the mixture was stirred at 45° C. for 2 hours (1000 rpm) to yield a derivatization solution. A composition of the resulting derivatization solution was analyzed by HPLC under the conditions shown below.

<HPLC Analysis Conditions>

Column: ODS Z-CLUE 3 μm, 2.0 mm×250 mm manufactured by Sumika Chemical Analysis Service.

Column compartment temperature: 50° C.

Eluent flow: 0.3 mL/min

Detection: UV 365 nm

Injection amount: 5 μL

Eluent composition: Solution A: 50 mM $NCOONH_4$ (pH 4.5); Solution B: MeCN

TABLE 2

HPLC gradient conditions

| Time (min) | Solution A(%) | Solution B(%) |
|---|---|---|
| 0.0 | 90 | 10 |
| 13.0 | 80 | 20 |
| 27.0 | 20 | 80 |
| 27.1 | 90 | 10 |
| 40.0 | 90 | 10 |

(3) Results

The C5-epimerization ratio was calculated from the ratio of GlcA-GlcN (NS) to IdoA-GlcN (NS) obtained by HPLC analysis, and its result is shown in Table 3. From the comparison in the reaction for 30 minutes, it was demonstrated that the cell-free extract containing MBP*-dreDlce (G70) exhibited the significantly higher C5-epimerization ratio. A symbol (-) in the table denotes that data was not obtained.

TABLE 3

C5-epimerization ratio

| Expressed Dlce | Source of gene | C5-epimerization ratio (%) 30 min | 12 hr |
|---|---|---|---|
| MBP*-hspDlce(G101) | human | 3.2 | 24.8 |
| MBP*-mdoDlce(G100) | opossum | 1.5 | 4.1 |
| MBP*-ggaDlce(G88) | chicken | 1.4 | 5.2 |
| MBP*-xtrDlce(G92) | frog | 1.4 | 3.3 |
| MBP*-dreDlce(G70) | zebrafish | 11.6 | 32.1 |
| MBP*-cinDlce(K92) | sea squirt | 1.2 | 1.9 |
| MBP*-dmeDlce(Y66) | *drosophila* | — | 0.5 |
| MBP*-celDlce | *C. elegans* | — | 0.7 |
| negative control | | 1.1 | 1.2 |

Example 5: Construction of Bacterial Strain Expressing Modified D-Glucuronyl C5-Epimerase (Dlce)

cDNA of catalytic sites (G70 to Asn585) in FcDlce-02, FcDlce-04, FcDlce-05, FcDlce-06 and FcDlce-07 which were variants of the D-glucuronyl C5-epimerase derived from zebrafish (dreDlce) were prepared by the artificial DNA synthesis (Thermo Fisher Scientific). A modification degree (indicates an amino acid sequence homology calculated using ClustalW) between full-length proteins of the wild type and each variant is shown in Table 4.

TABLE 4

Amino acid sequence homologies between full-length proteins of the wild type and each variants (calculated using ClustalW)

| | dreDlce | FcDlce-02 | FcDlce-04 | FcDlce-05 | FcDlce-06 | FcDlce-07 |
|---|---|---|---|---|---|---|
| dreDlce | | 80 | 84 | 90 | 95 | 98 |
| FcDlce-02 | | | 97 | 91 | 86 | 82 |
| FcDlce-04 | | | | 94 | 89 | 86 |
| FcDlce-05 | | | | | 95 | 92 |
| FcDlce-06 | | | | | | 97 |
| FcDlce-07 | | | | | | |

DNA fragments including a nucleotide sequence encoding the catalytic site of FcDlce-02 (G70 to Asn585), the catalytic site of FcDlce-04 (G70 to Asn585), the catalytic site of FcDlce-05 (G70 to Asn585), the catalytic site of FcDlce-06 (G70 to Asn585), and the catalytic site of FcDlce-07 (G70 to Asn585) were obtained in the same method as in Example 2 using these cDNA as a template. The combinations of SEQ ID NOS:69 and 70, SEQ ID NOS:71 and 47, SEQ ID NOS:72 and 47, SEQ ID NOS:46 and 47 or SEQ ID NOS:46 and 47 were used as primers, respectively. Plasmids pMAL-MBP*-FcDlce-02 (G70), pMAL-MBP*-FcDlce-04 (G70), pMAL-MBP*-FcDlce-05 (G70), pMAL-MBP*-FcDlce-06 (G70) and pMAL-MBP*-FcDlce-07 (G70) were obtained in the same method as in Example 2 (2). *Escherichia coli* Origami B(DE3) was transformed with the resulting plasmids. The resulting bacterial strains were designated as *Escherichia coli* Origami B(DE3)/pMAL-MBP*-FcDlce-02 (G70), *Escherichia coli* Origami B(DE3)/pMAL-MBP*-FcDlce-04 (G70), *Escherichia coli* Origami B(DE3)/pMAL-MBP*-FcDlce-05 (G70), *Escherichia coli* Origami B(DE3)/pMAL-MBP*-FcDlce-06 (G70), and *Escherichia coli* Origami B(DE3)/pMAL-MBP*-FcDlce-07 (G70), and used as a bacterial strain expressing modified Dlce. Nucleotide sequences of the inserted fragments are shown in SEQ ID NOS:55, 58, 61, 64 and 67, respectively and amino acid sequences encoded thereby are shown in SEQ ID NOS:56, 59, 62, 65 and 68.

Example 6: Expression of Wild Type and Modified D-Glucuronyl C5-Epimerase (Dlce)

*Escherichia coli* Origami B(DE3)/pMAL-MBP*-dreDlce (G70), *Escherichia coli* Origami B(DE3)/pMAL-MBP*-FcDlce-02 (G70), *Escherichia coli* Origami B(DE3)/pMAL-MBP*-FcDlce-04 (G70), *Escherichia coli* Origami B(DE3)/pMAL-MBP*-FcDlce-05 (G70), *Escherichia coli* Origami B(DE3)/pMAL-MBP*-FcDlce-06 (G70), and *Escherichia coli* Origami B(DE3)/pMAL-MBP*-FcDlce-07 (G70) were used to express the wild type and modified Dlce in the microbial cells by the same method as in Example 3 to yield cell-free extracts containing Dlce.

Example 7: C5-Epimerization Reaction by Cell-Free Extract Containing Wild Type or Modified Dlce A C5-epimerization reaction by cell-free extract containing wild type or modified Dlce, and quantification of a C5-epimeriazation ratio were performed in the same methods as in Example 4. The negative control was the same as in Example 4.

The C5-epimerization ratio was calculated from the ratio of GlcA-GlcN (NS) to IdoA-GlcN (NS) obtained by HPLC analysis and the results are shown in Table 5. It was demonstrated that the cell-free extracts each containing MBP*-FcDlce-02 (G70), MBP*-FcDlce-04 (G70), MBP*-FcDlce-05 (G70), MBP*-FcDlce-06 (G70), and MBP*-FcDlce-07 (G70) exhibited the C5-epimerization ratio which was equivalent to or higher than that of the cell-free extract containing MBP*-dreDlce (G70).

TABLE 5

C5-epimerization ratio

| Expressed Dice | Source of gene | C5-epimerization ratio (%) 30 min |
|---|---|---|
| MBP*-dreDlce(G70) | zebrafish | 15.7 |
| MBP*-FcDlce-02(G70) | — | 22.0 |
| MBP*-FcDlce-04(G70) | — | 23.9 |
| MBP*-FcDlce-05(G70) | — | 25.4 |
| MBP*-FcDlce-06(G70) | — | 29.8 |
| MBP*-FcDlce-07(G70) | — | 17.9 |
| negative control | | 4.0 |

Sequence Listing Free Text

SEQ ID NO:1 represents the naturally occurring full-length nucleotide sequence encoding D-glucuronyl C5-epimerase derived from zebrafish (GenBank Accession No. AY388517.1).

SEQ ID NO:2 represents the naturally occurring full-length amino acid sequence of D-glucuronyl C5-epimerase derived from zebrafish (GenBank Accession No. AY388517.1).

SEQ ID NO:3 represents a naturally occurring nucleotide sequence encoding the partial amino acid sequence (GLY70 to Asn585 in SEQ ID NO:2) of the D-glucuronyl C5-epimerase derived from zebrafish.

SEQ ID NO:4 represents a codon-optimized nucleotide sequence encoding the partial amino acid sequence (GLY70 to Asn585 in SEQ ID NO:2) of the D-glucuronyl C5-epimerase derived from zebrafish.

SEQ ID NO:5 represents the partial amino acid sequence (GLY70 to Asn585 in SEQ ID NO:2) of the D-glucuronyl C5-epimerase derived from zebrafish.

SEQ ID NO:6 represents a nucleotide sequence encoding the partial amino acid sequence (Gly101 to Asn617) of the D-glucuronyl C5-epimerase derived from zebrafish.

SEQ ID NO:7 represents the partial amino acid sequence (Gly101 to Asn617) of the D-glucuronyl C5-epimerase derived from zebrafish.

SEQ ID NO:8 represents a nucleotide sequence encoding the partial amino acid sequence (Gly100 to Asn617) of D-glucuronyl C5-epimerase derived from opossum.

SEQ ID NO:9 represents the partial amino acid sequence (Gly100 to Asn617) of the D-glucuronyl C5-epimerase derived from opossum.

SEQ ID NO:10 represents a nucleotide sequence encoding the partial amino acid sequence (Gly88 to Asn605) of D-glucuronyl C5-epimerase derived from chicken.

SEQ ID NO:11 represents the partial amino acid sequence (Gly88 to Asn605) of the D-glucuronyl C5-epimerase derived from chicken.

SEQ ID NO:12 represents a nucleotide sequence encoding the partial amino acid sequence (Gly92 to Asn607) of D-glucuronyl C5-epimerase derived from frog.

SEQ ID NO:13 represents the partial amino acid sequence (Gly92 to Asn607) of the D-glucuronyl C5-epimerase derived from frog.

SEQ ID NO:14 represents a nucleotide sequence encoding the partial amino acid sequence (K92 to Asn637) of D-glucuronyl C5-epimerase derived from sea squirt.

SEQ ID NO:15 represents the partial amino acid sequence (K92 to Asn637) of the D-glucuronyl C5-epimerase derived from sea squirt.

SEQ ID NO:16 represents a nucleotide sequence encoding the partial amino acid sequence (Y66 to Asn614) of D-glucuronyl C5-epimerase derived from *Drosophila.*

SEQ ID NO:17 represents the partial amino acid sequence (Y66 to Asn614) of the D-glucuronyl C5-epimerase derived from *Drosophila.*

SEQ ID NO:18 represents a nucleotide sequence encoding the full-length amino acid sequence of D-glucuronyl C5-epimerase derived from *C. elegans.*

SEQ ID NO:19 represents the full-length amino acid sequence of the D-glucuronyl C5-epimerase derived from *C. elegans.*

SEQ ID NO:20 represents the nucleotide sequence of pMAL-c2x plasmid.

SEQ ID NO:21 represents the nucleotide sequence of pMAL-MBP* plasmid.

SEQ IN NOS:22 to 31 represents nucleotide sequences of primers and fragments used for constructing hepC gene expression plasmids in Example 1.

SEQ ID NO:22 represents the nucleotide sequence of primer P1.

SEQ ID NO:23 represents the nucleotide sequence of primer P2.

SEQ ID NO:24 represents the nucleotide sequence of PaeI-SalI fragment of Pnlp0 promoter.

SEQ ID NO:25 represents the nucleotide sequence of primer P3.

SEQ ID NO:26 represents the nucleotide sequence of primer P4.

SEQ ID NO:27 represents the nucleotide sequence of a DNA fragment including about 300 bp of a terminator region in an rrnB gene (SEQ ID NO:6).

SEQ ID NO:28 represents the nucleotide sequence of primer P5.

SEQ ID NO:29 represents the nucleotide sequence of primer P6.

SEQ ID NO:30 represents the nucleotide sequence of primer P7.

SEQ ID NO:31 represents the nucleotide sequence of primer P8.

SEQ ID NO:32 represents the nucleotide sequence of hepC gene cloned in Example 1.

SEQ ID NO:33 represents an amino acid sequence of heparinase III (HepC) encoded by the nucleotide sequence of SEQ ID NO:32.

SEQ ID NOS:34 and 35 represent nucleotide sequences of primers used for preparing MBP* in Example 2.

SEQ ID NOS:36 and 37 represent nucleotide sequences of primers used for acquiring a fragment of D-glucuronyl C5-epimerase derived from human in Example 2.

SEQ ID NOS:38 and 39 represent nucleotide sequences of primers used for acquiring a DNA fragment of pMAL-MBP* in Example 2.

SEQ ID NOS:40 and 41 represent nucleotide sequences of primers used for acquiring a fragment of D-glucuronyl C5-epimerase derived from opossum in Example 2.

SEQ ID NOS:42 and 43 represent nucleotide sequences of primers used for acquiring a fragment of D-glucuronyl C5-epimerase derived from chicken in Example 2.

SEQ ID NOS:44 and 45 represent nucleotide sequences of primers used for acquiring a fragment of D-glucuronyl C5-epimerase derived from frog in Example 2.

SEQ ID NOS:46 and 47 represent nucleotide sequences of primers used for acquiring a fragment of D-glucuronyl C5-epimerase derived from zebrafish in Example 2.

SEQ ID NOS:48 and 49 represent nucleotide sequences of primers used for acquiring a fragment of D-glucuronyl C5-epimerase derived from sea squirt in Example 2.

SEQ ID NOS:50 and 51 represent nucleotide sequences of primers used for acquiring a fragment of D-glucuronyl C5-epimerase derived from *Drosophila* in Example 2.

SEQ ID NOS:52 and 53 represent nucleotide sequences of primers used for acquiring a fragment of D-glucuronyl C5-epimerase derived from *C. elegans* in Example 2.

SEQ ID No:54 represents the full-length amino acid sequence of a variant FcDlce-02.

SEQ ID No:55 represents a nucleotide sequence encoding the partial amino acid sequence Gly70 to Asn585 of the variant FcDlce-02.

SEQ ID No:56 represents the partial amino acid sequence Gly70 to Asn585 of the variant FcDlce-02.

SEQ ID No:57 represents the full-length amino acid sequence of a variant FcDlce-04.

SEQ ID No:58 represents a nucleotide sequence encoding the partial amino acid sequence Gly70 to Asn585 of the variant FcDlce-04.

SEQ ID No:59 represents the partial amino acid sequence Gly70 to Asn585 of the variant FcDlce-04.

SEQ ID No:60 represents the full-length amino acid sequence of a variant FcDlce-05.

SEQ ID No:61 represents a nucleotide sequence encoding the partial amino acid sequence Gly70 to Asn585 of the variant FcDlce-05.

SEQ ID No:62 represents the partial amino acid sequence Gly70 to Asn585 of the variant FcDlce-05.

SEQ ID No:63 represents the full-length amino acid sequence of a variant FcDlce-06.

SEQ ID No:64 represents a nucleotide sequence encoding the partial amino acid sequence Gly70 to Asn585 of the variant FcDlce-06.

SEQ ID No:65 represents the partial amino acid sequence Gly70 to Asn585 of the variant FcDlce-06.

SEQ ID No:66 represents the full-length amino acid sequence of a variant FcDlce-07.

SEQ ID No:67 represents a nucleotide sequence encoding the partial amino acid sequence Gly70 to Asn585 of the variant FcDlce-07.

SEQ ID No:68 represents the partial amino acid sequence Gly70 to Asn585 of the variant FcDlce-07.

SEQ ID NOS:69 and 70 represent nucleotide sequences of primers used for acquiring a fragment of the variant FcDlce-02 in Example 5.

SEQ ID No:71 represents the nucleotide sequence of the primer used for obtaining a fragment of the variant FcDlce-04 in Example 5.

SEQ ID No:72 represents the nucleotide sequence of the primer used for obtaining a fragment of the variant FcDlce-05 in Example 5.

The invention claimed is:

1. A protein selected from the group consisting of:

(1) a protein comprising the amino acid sequence of SEQ ID NO. 56;

(2) a protein which comprises an amino acid sequence having 97% or more identity to the amino acid sequence of SEQ ID NO. 56 and has a D-glucuronyl C5-epimerase activity; and (3) a protein which comprises an amino acid sequence having 1 to 10 deleted, substituted, added or inserted amino acid residues in the amino acid sequence of SEQ ID NO. 56 and has a D-glucuronyl C5-epimerase activity;

(4) a protein comprising the amino acid sequence of SEQ ID 59;

(5) a protein which comprises an amino acid sequence having 97% or more identity to the amino acid sequence of SEQ ID 59 and has a D-glucuronyl C5-epimerase activity;

(6) a protein which comprises an amino acid sequence having I to 10 deleted, substituted, added or inserted amino acid residues in the amino acid sequence of SEQ ID 59 and has a D-glucuronyl C5-epimerase activity;

(7) a protein comprising the amino acid sequence of SEQ ID 62;

(8) a protein which comprises an amino acid sequence having 95% or more identity to the amino acid sequence of SEQ ID 62 and has a D-glucuronyl C5-epimerase activity;

(9) a protein which comprises an amino acid sequence having 1 to 25 deleted substituted, added or inserted amino acid residues in the amino acid sequence of SEQ ID 62 and has a D-glucuronyl C5-epimerase activity;

(10) a protein comprising the amino acid sequence of SEQ ID 65;

(11) a protein which comprises an amino acid sequence having 97% or more identity to the amino acid sequence of SEQ ID 65 and has a D-glucuronyl C5-epimerase activity;

(12) a protein which comprises an amino acid sequence having 1 to 10 deleted, substituted, added or inserted amino acid residues in the amino acid sequence of SEQ ID 65 and has a D-glucuronyl C5-epimerase activity;

(13) a protein comprising the amino acid sequence of SEQ ID 68;

(14) a protein which comprises an amino acid sequence having 99% or more identity to the amino acid sequence of SEQ ID 68 and has a D-glucuronyl C5-epimerase activity; and

(15) a protein which comprises an amino acid sequence having 1 to 5 deleted, substituted, added or inserted amino acid residues in the amino acid sequence of SEQ ID 68 and has a D-glucuronvl C5-epimerase activity.

2. The protein according to claim 1, wherein the protein is selected from the group consisting of (1), (2), and (3).

3. The protein according to claim 1, wherein the protein is selected from the group consisting of (4), (5), and (6).

4. The protein according to claim 1, wherein the protein is selected from the group consisting of (7), (8), and (9).

5. The protein according to claim 1, wherein the protein is selected from the group consisting of (10), (11), and (12).

6. The protein according to claim 1, wherein the protein is selected from the group consisting of (13), (14), and (15).

7. A method for producing a heparosan compound having an isomerized hexuronicacid residue, said method comprising producing the heparosan compound having the isomerized hexuronicacid residue from a heparosan compound wherein isomerization of the hexuronic acid residue is catalyzed by the protein according to claim 1.

8. The method according to claim 7, wherein the heparosan compound having the isomerized hexuronic acid residue is produced in the presence of a transformed microorganism producing said protein or an extract thereof.

9. The method according to claim 8, wherein said transformed microorganism is a bacterium belonging to genus *Escherichia*.

10. The method according to claim 9, wherein said transformed microorganism is *Escherichia coli*.

11. The method according to claim 7, wherein said heparosan compound is an N-sulfated heparosan.

12. The method according to claim 7, wherein said heparosan compound is a low-molecularized heparosan.

13. A method for producing a heparan sulfate, said method comprising subjecting a heparosan to a treatment comprising C5-epimerization of a hexuronicacid residue, 2-O-sulfation of a hexuronicacid residue, N-deacetylation of an α-D-glucosamine residue, N-sulfation of an α-D-glucosamine residue, 3-O-sulfation of an a-D-glucosamine residue, and 6-O-sulfation of an α-D-glucosamine residue to produce the heparan sulfate, wherein the C5-epimerization is catalyzed by the protein according to claim 1.

14. The method according to claim 13, wherein the treatment further comprises decomposition of a heparosan.

* * * * *